United States Patent
Schoenfeld et al.

(10) Patent No.: US 11,807,667 B2
(45) Date of Patent: Nov. 7, 2023

(54) THERMOSTABLE VIRAL REVERSE TRANSCRIPTASE

(71) Applicant: QIAGEN BEVERLY, LLC, Beverly, MA (US)

(72) Inventors: Thomas William Schoenfeld, Topsfield, MA (US); Ryan Charles Heller, Amesbury, MA (US); Katarzyna Crissy, Windham, NH (US); Suhman Chung, South Hamilton, MA (US)

(73) Assignee: QIAGEN BEVERLY, LLC., Beverly, MA (US)

( * ) Notice: Subject to any disclaimer, the term of this patent is extended or adjusted under 35 U.S.C. 154(b) by 0 days.

(21) Appl. No.: 17/052,237

(22) PCT Filed: Apr. 30, 2019

(86) PCT No.: PCT/IB2019/053537
§ 371 (c)(1),
(2) Date: Nov. 2, 2020

(87) PCT Pub. No.: WO2019/211749
PCT Pub. Date: Nov. 7, 2019

(65) Prior Publication Data
US 2021/0171580 A1 Jun. 10, 2021

Related U.S. Application Data

(60) Provisional application No. 62/665,560, filed on May 2, 2018, provisional application No. 62/790,483, filed on Jan. 10, 2019, provisional application No. 62/835,521, filed on Apr. 18, 2019.

(30) Foreign Application Priority Data

May 18, 2018 (EP) .................................... 18173195

(51) Int. Cl.
*C12N 9/12* (2006.01)
*C07K 14/00* (2006.01)
*C12Q 1/6844* (2018.01)

(52) U.S. Cl.
CPC ............ *C07K 14/00* (2013.01); *C12N 9/1276* (2013.01); *C12Q 1/6844* (2013.01); *C12Q 2531/113* (2013.01)

(58) Field of Classification Search
None
See application file for complete search history.

(56) References Cited

FOREIGN PATENT DOCUMENTS

WO    WO 2007/044671    4/2007

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Schoenfield et al. (Lateral Gene Transfer of Family A DNA Polymerases between Thermophilic Viruses, Aquificae, and Apicomplexa, Mol. Biol. Evol. 30(7) pp. 1653-1664, Apr. 2013).*
U.S. Appl. No. 62/835,521, filed Apr. 18, 2019, Schoenfeld (Qiagen).
U.S. Appl. No. 62/790,483, filed Jan. 10, 2019, Schoenfeld (Qiagen).
U.S. Appl. No. 62/665,560, filed May 2, 2018, Schoenfeld (Qiagen).
PCT, PCT/IB2019/05353, Apr. 30, 2019, Schoenfeld (Qiagen).
International Preliminary Report on Patentability dated Nov. 3, 2020 by the IB in PCT/IB2019/053537, filed Apr. 30, 2019. (6 pages).
Written Opinion and International Search Report dated Jun. 2, 2019 by the EPO in PCT/IB2019/053537, filed Apr. 30, 2019. (9 pages).

* cited by examiner

*Primary Examiner* — Richard G Hutson
(74) *Attorney, Agent, or Firm* — BALLARD SPAHR LLP

(57) ABSTRACT

The present invention provides novel engineered polypeptides that support both reverse transcription and DNA amplification in manganese-independent reactions. The present invention also provides methods for amplifying template nucleic acids using such polypeptides. This invention addresses deficiencies in the current state of the art in nucleic acid amplification-based detection of template nucleic acids, especially RNA targets, including deficiencies in detection sensitivity, specificity, enzyme stability, inhibitor tolerance and time to result compared with manganese-dependent thermostable reverse transcriptases and two-enzyme solutions.

15 Claims, 20 Drawing Sheets

Specification includes a Sequence Listing.

```
Parent 1              400  QIGKSANFGLIYGIAPKGFAEYCIANGINMTEEQAYEIVRKWKKYYTKIAEQHQVAYERFKYNEYVDNETWLN  472
Parent 2              400  QIGKSANFGLIYGISPKGFAEYCISNGINITEEMAIEIVKKWKKFYRKIAEQHQLAYERFKYAEFVDNETWLN  472
Parent 3              400  QIGKSANFGLIYGIAPKGFAEYCITNGINMTEEQAYEIVKKWKRYYTKITEQHQVAYERFKYNEYVDNETWLA  472
M180_PRT              400  QIGKSANFGLIYGISPKGFAEYCISNGINITEEMAIEIVKKWKKFYRKIAEQHQLAYERFKYAEFVDNETWLN  472
M384_PRT              400  QIGKSANFGLIYGISPKGFAEYCISNGINITEEMAIEIVKKWKKFYRKIAEQHQLAYERFKYAEFVDNETWLN  472
M392_PRT              400  QIGKSANFGLIYGISPKGFAEYCISNGINITEEMAIEIVKKWKKFYRKIAEQHQLAYERFKYAEFVDNETWLN  472
M295_PRT              400  QIGKSANFGLIYGISPKGFAEYCISNGINITEEMAIEIVKKWKKFYRKIAEQHQLAYERFKYAEFVDNETWLN  472
M66_PRT               400  QIGKSANFGLIYGISPKGFAEYCISNGINITEEMAIEIVKKWKKFYRKIAEQHQLAYERFKYAEFVDNETWLN  472
M160_PRT              400  QIGKSANFGLIYGISPKGFAEYCISNGINITEEMAIEIVKKWKKFYRKIAEQHQLAYERFKYAEFVDNETWLN  472
Conserved P2 residues       *           *   *  * *       ** *   *      * *          *
                           ----Motif B----
                        ----O Helix----------------------- ---P Helix----- -Beta Sheets 10,11-
```

B

```
Parent 1              231  QLRSEMQKQIPFNYNSPKQTAKFFGVNSSS  260
Parent 2              231  QLRNQMQKEIPFNYNSPKQTAKLFGIDSSS  260
Parent 3              231  QLRSEMQRQIPFNYNSPKQTAKFFGVDSSS  260
M180_PRT              231  QLRSEMQRQIPFNYNSPKQTAKFFGVDSSS  260
M384_PRT              231  QLRSEMQKQIPFNYNSPKQTAKFFGVDSSS  260
M392_PRT              231  QLRSEMQRQIPFNYNSPKQTAKFFGVDSSS  260
M295_PRT              231  QLRSEMQRQIPFNYNSPKQTAKFFGVDSSS  260
M66_PRT               231  QLRSEMQKQIPFNYNSPKQTAKFFGVNSSS  260
M160_PRT              231  QLRSEMQKQIPFNYNSPKQTAKFFGVNSSS  260
Conserved P1/3             **  *                  *  *
                           -----H Helix---------------
```

FIG. 5:
A
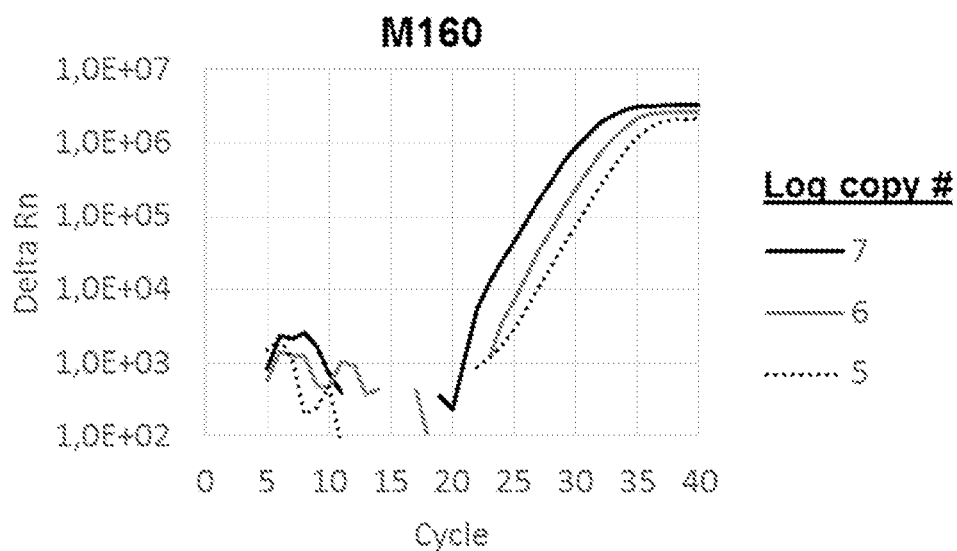
B
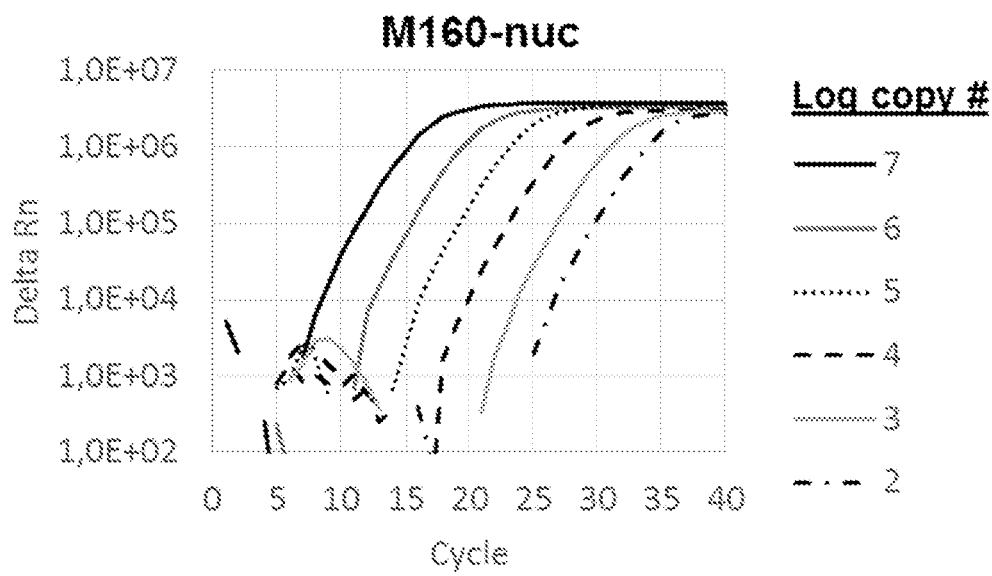

FIG. 7:
A
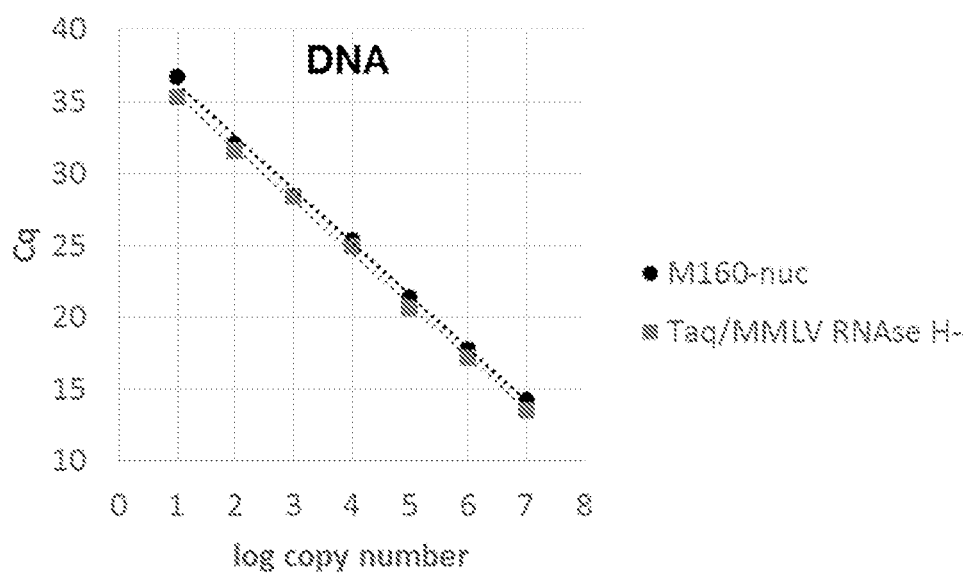
B
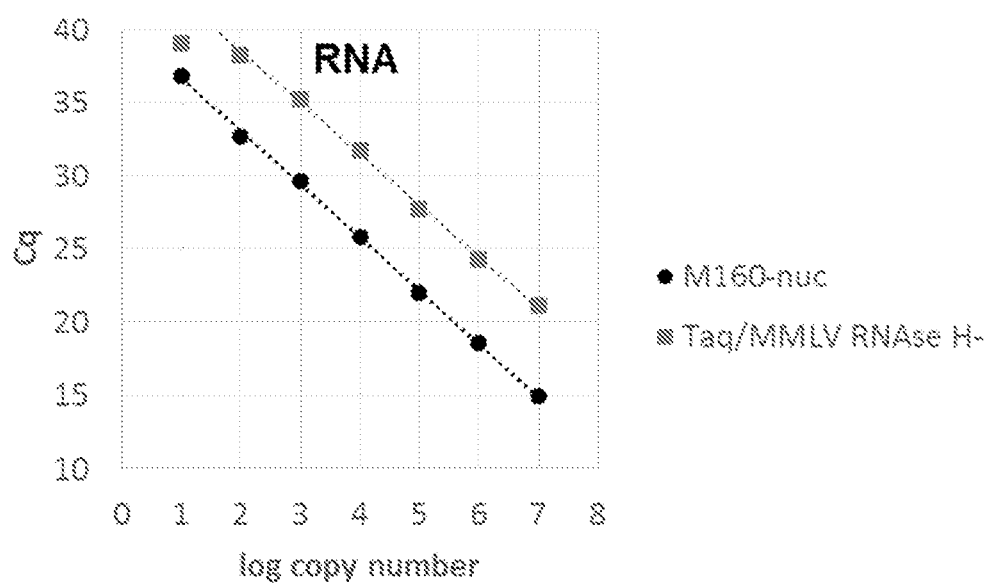

FIG. 10:
A
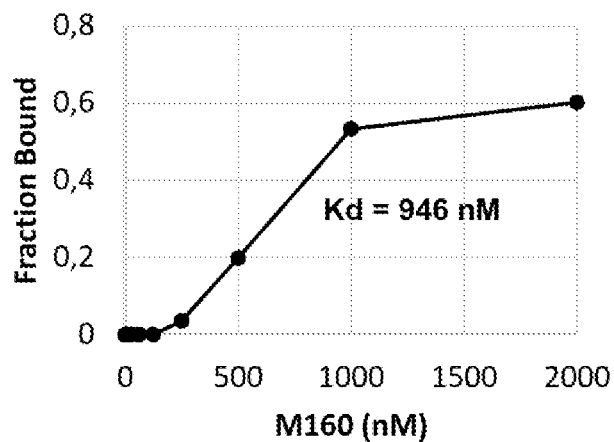
B
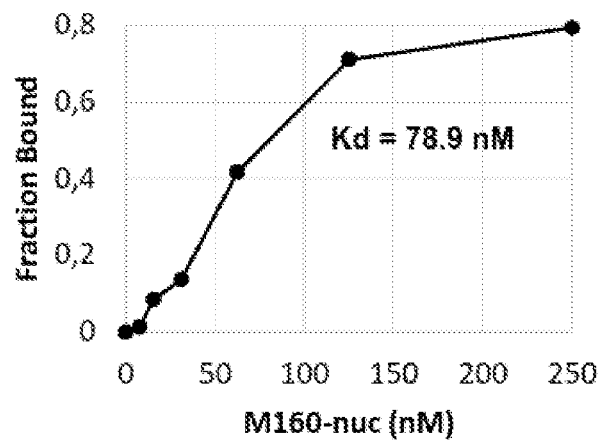
C
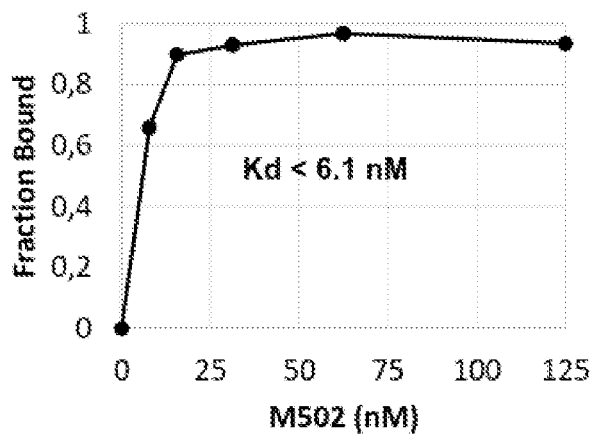

FIG. 11:
A
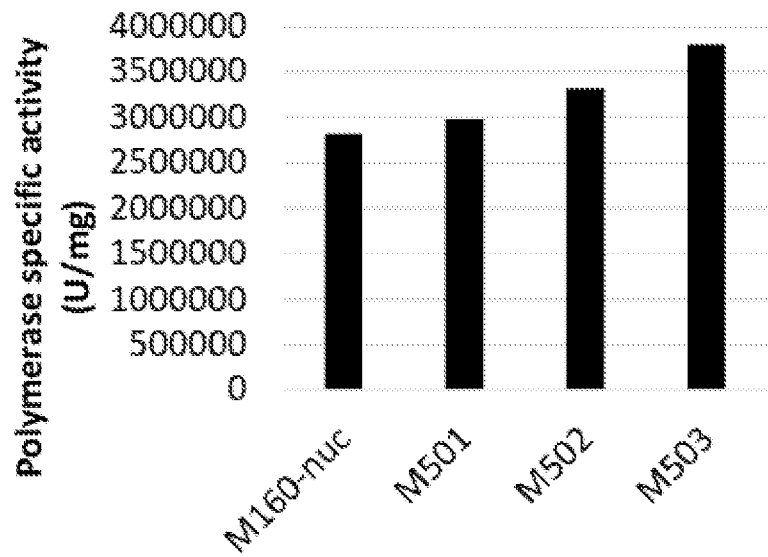
B
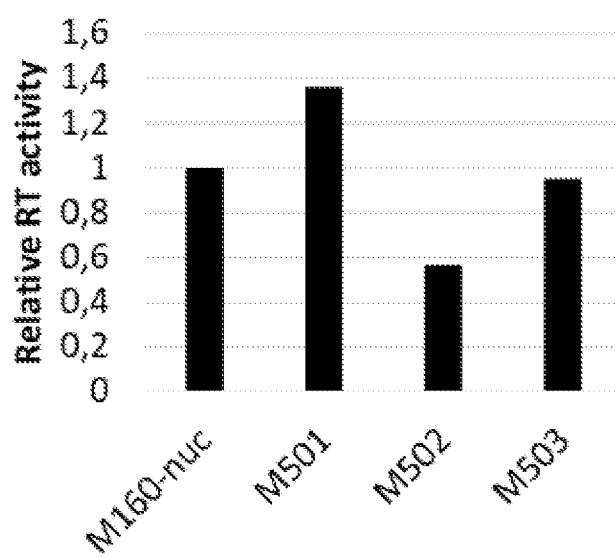

FIG. 13:
A
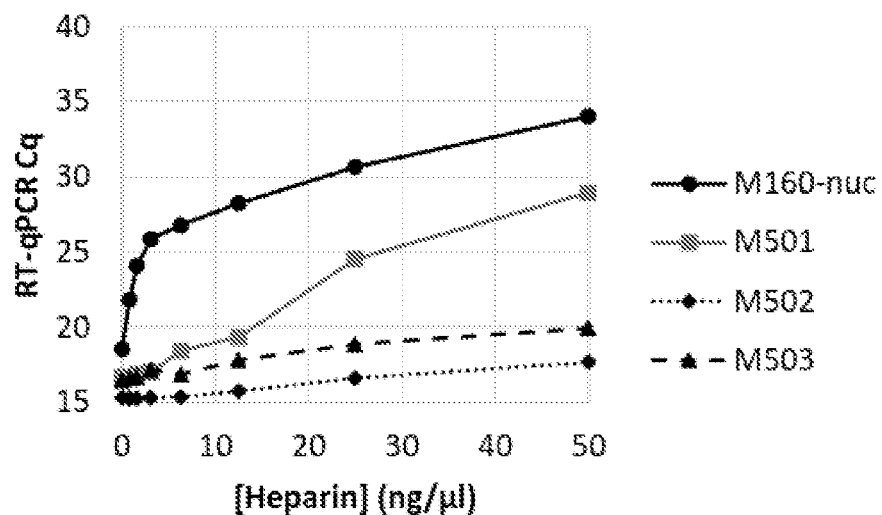
B
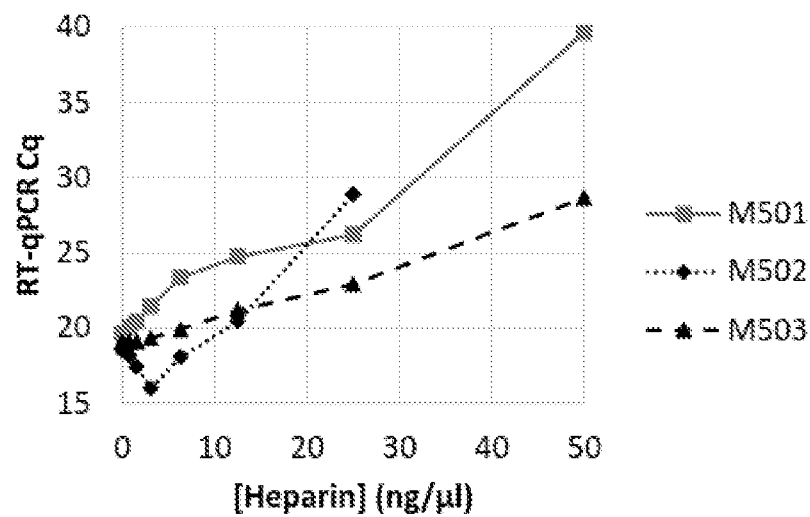

FIG. 14:
A
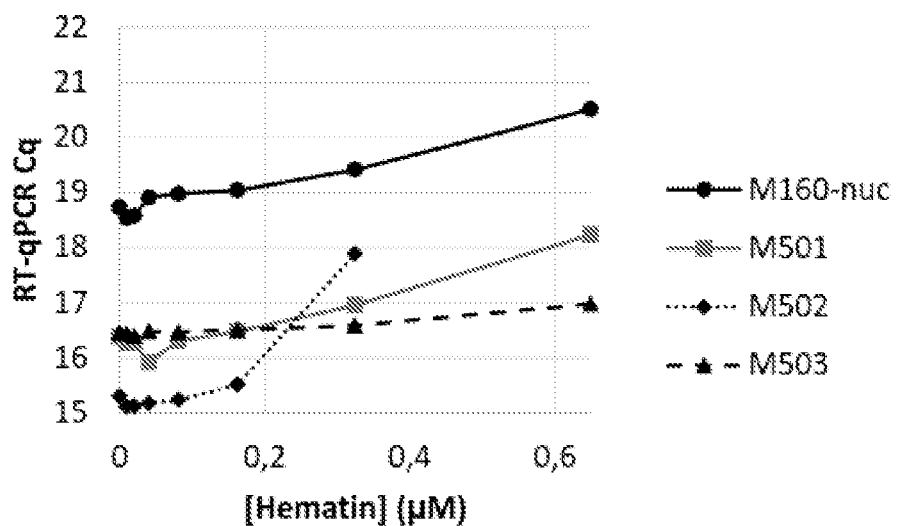
B
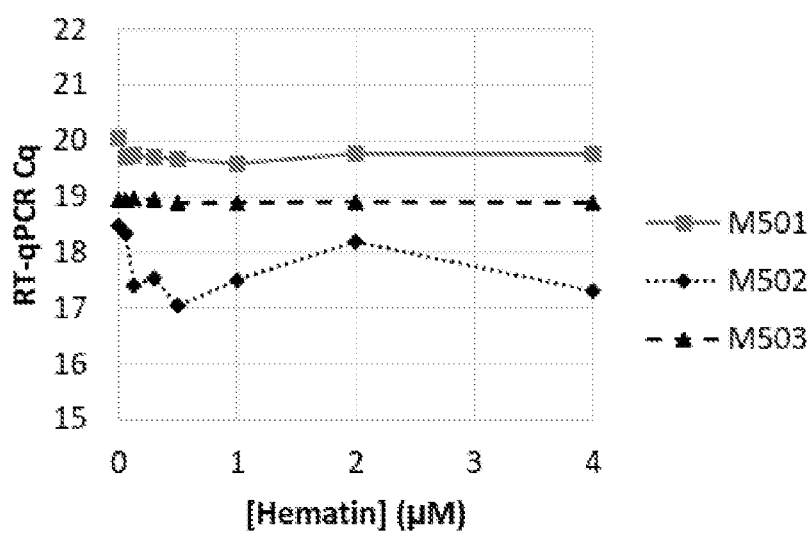

FIG. 15:
A
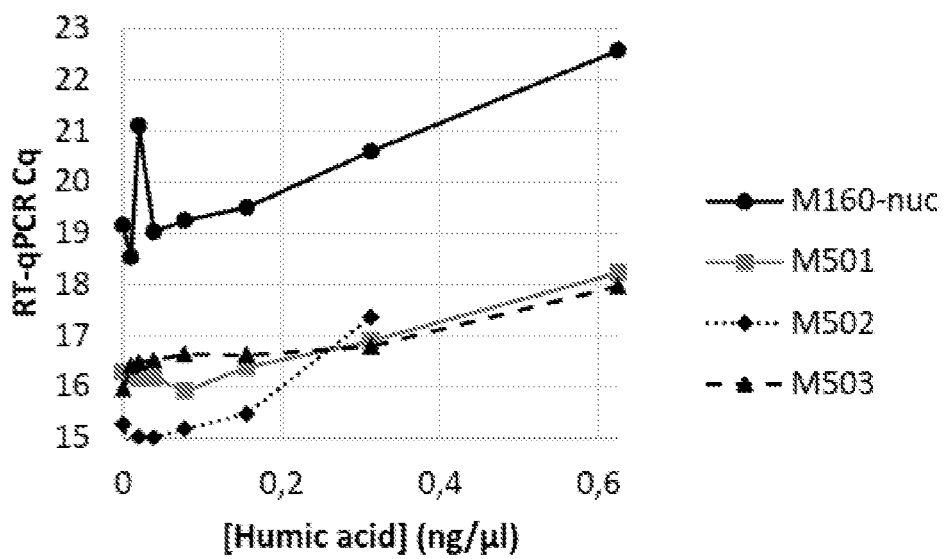
B
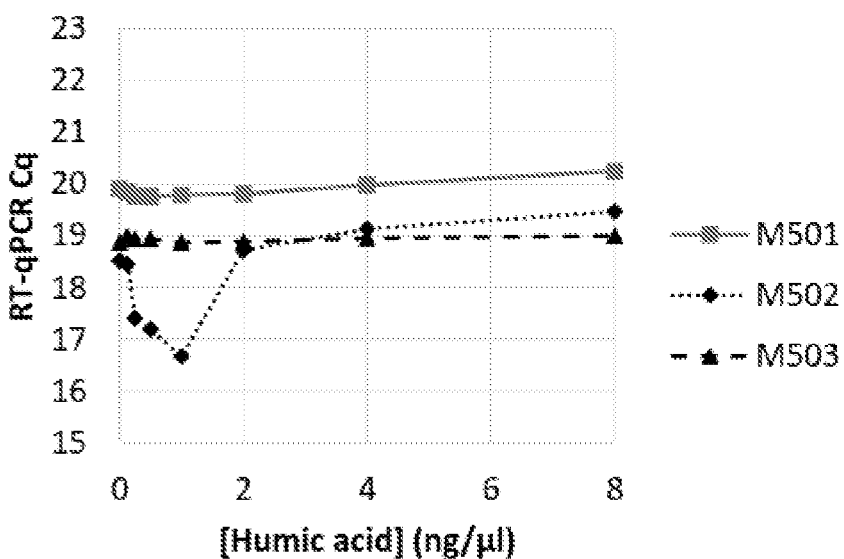

FIG. 16:
A
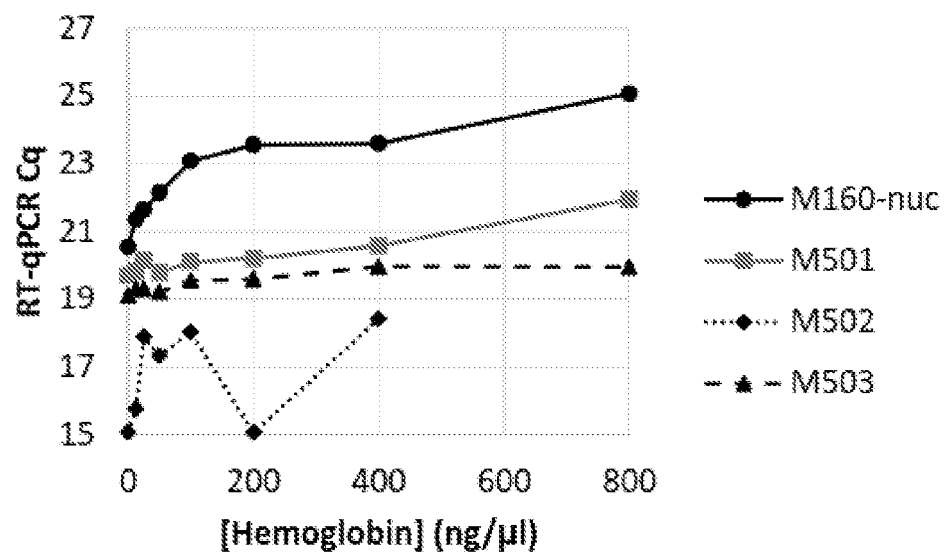
B
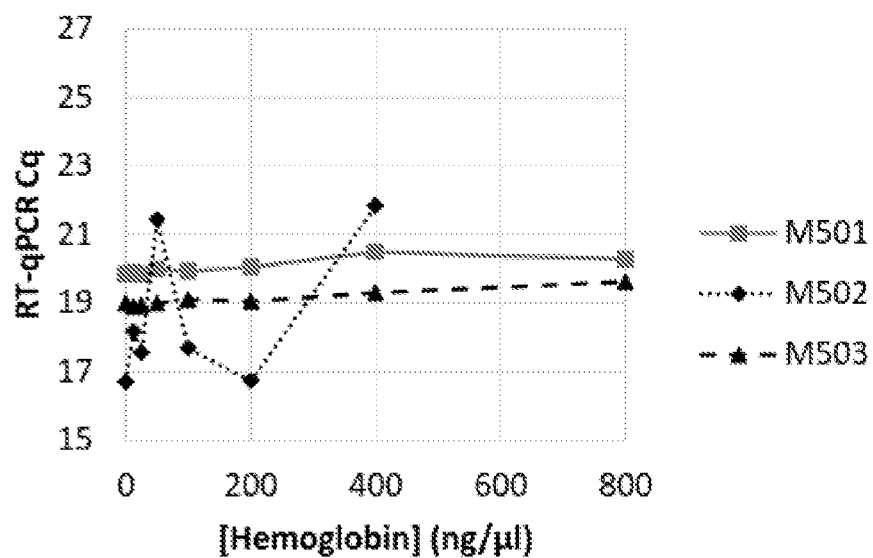

FIG. 17:
A
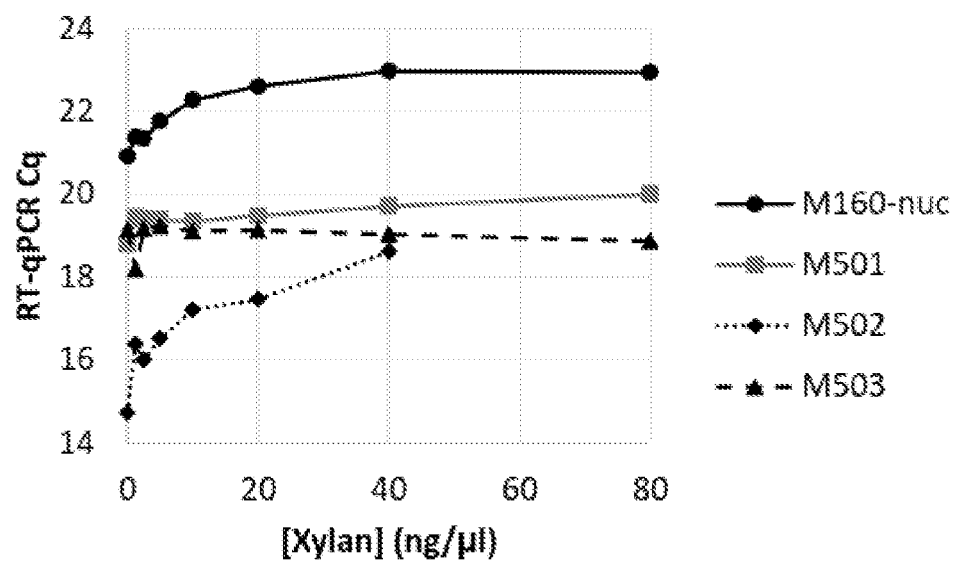
B
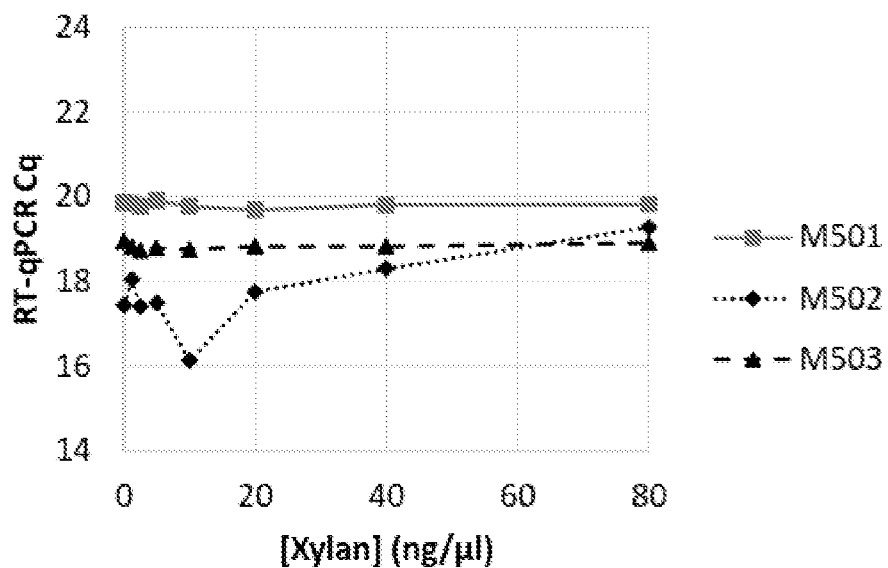

FIG. 18:
A
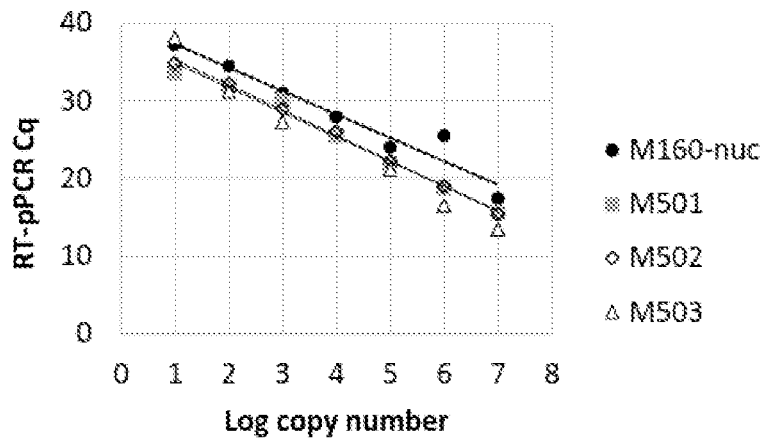
B
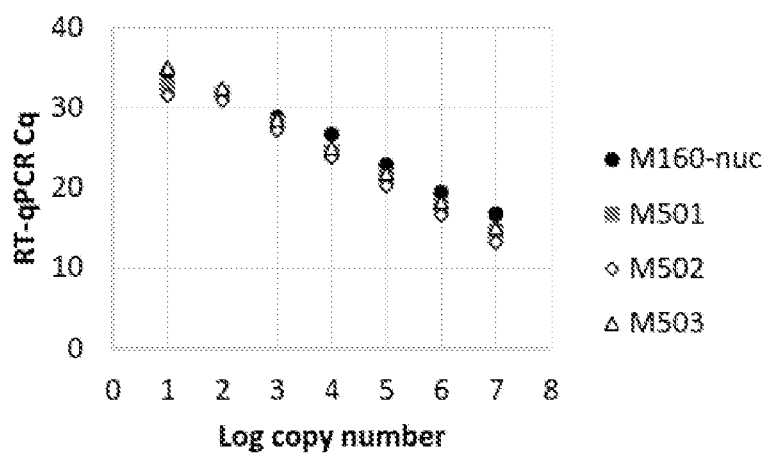
C
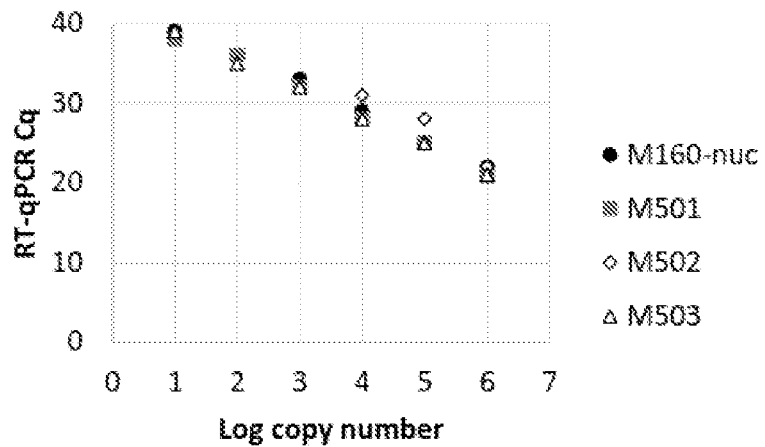

FIG. 19:
A
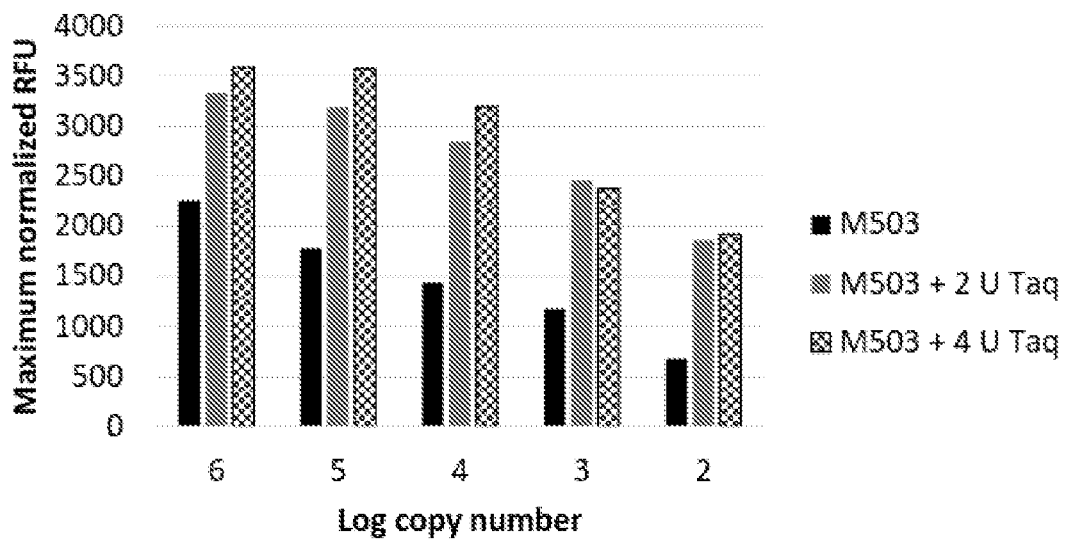
B
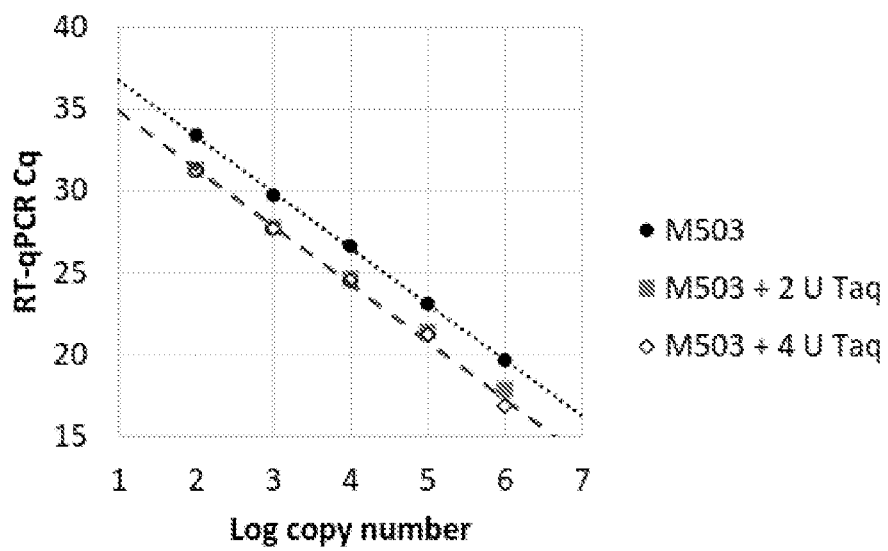

FIG. 21:
A
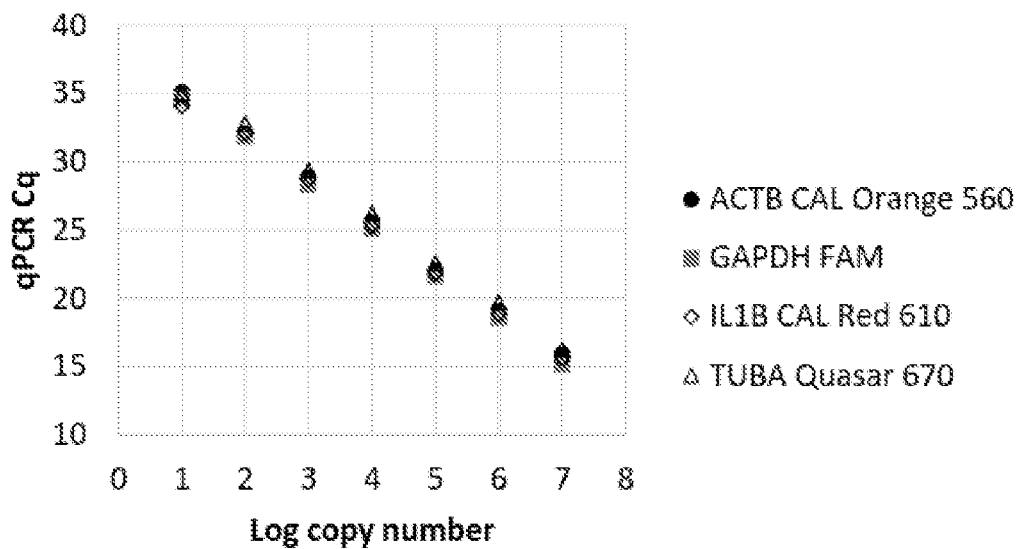
B
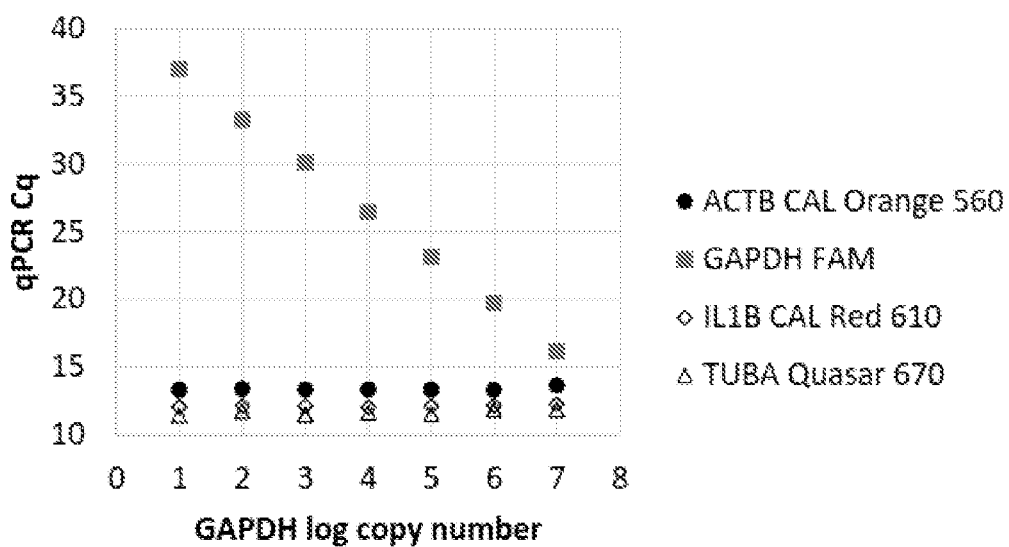

SEQUENCE LISTING

```
<160> NUMBER OF SEQ ID NOS: 88

<210> SEQ ID NO 1
<211> LENGTH: 1734
<212> TYPE: DNA
<213> ORGANISM: Artificial Sequence
<220> FEATURE:
<223> OTHER INFORMATION: M66 DNA

<400> SEQUENCE: 1
atgaataccc cgaaaccgat tctgaaaccg cagagcaaag cactggttga accggtgctg      60
tgtaatagca ttgatgaaat tccggcaaaa tacaacgagc cgatctattt tgatctggca     120
accgatgaag atcgtccggt tctggcaagc atttatcagc cgcattttga acgtaaagtg     180
tattgtctga atctgctgaa agaaaacccg gaacgtttta aagaatggct gctgaaattt     240
agcgaaattc gtggttgggg cttagatttc gatctgcgtg ttctgggtta tacctatgaa     300
cagctgcgta acaaaaaaat cattgatgtt cagctggccc tgaaagtgca gcattatgaa     360
cgctttaaac agaatggtgc caaaggtgaa ggttttcgtc tggatgatgt tgcacgtgat     420
ctgctgggta ttgaatatcc gatgaacaaa acgaaaatcc gcaccacctt caagtataac     480
atgtatagca gcttttcgta cgagcaactg ctgtatgcaa gcctggatgc atatattccg     540
catctgctgt acgaacgtct gagcagcgat accctgaata gcctggttta tcagattgat     600
caagaggttc agaaagtggt gattgaaacc agccagcatg gtatgccggt taaactgaaa     660
gcactggaag aagaattca tcgtctgacc cagctgcgta gcgaaatgca gaaacaaatt     720
```

```
ccgtttaact ataatagccc gaaacagacc gccaaattct ttggtgttaa tagcagcagc   780
aaagatgttc tgatggatct ggcactgcgt ggtaatgaag ttgccaaaaa agttctggaa   840
gcacgccaga ttgaaaaaag tctggcattc gccaaagatc tgtatgatat cgccaaaaaa   900
aacggtggtc gcatctatgg taacttttt accaccaccg caccgagcgg tcgtatgagc   960
tgtagcgata ttaacctgca gcaaattccg cgtcgtctgc gtccgtttat tggttttgaa  1020
accgaagata aaaagctgat caccgcagat tttccgcaga ttgaactgcg tctggcaggc  1080
gttatttggg atgaaccgaa atttatcgaa gcatttcgtc agggtatcga tctgcataaa  1140
ctgaccgcaa gcattctgtt cgataaaaac attgaagagg tgagcaaaga agaacgccag  1200
attggtaaaa gcgcaaattt tggtctgatt tatggtatca gcccgaaagg ttttgccgaa  1260
tattgtatta gcaacggcat taacatcacc gaagaaatgg caatcgagat cgtgaaaaaa  1320
tggaagaagt tctatcgcaa aatcgccgaa cagcatcagc tggcatatga acgttttcaaa  1380
tatgccgaat cgtggataa tgaaacctgg ctgaatcgta cctatcgtgc atggaaaccg  1440
caagatctgc tgaattatca gattcaaggt agcggtgcag aactgttcaa aaagcaatt  1500
atcctgctta agaagccaa accggatctg aaaattgtga atctggtgca tgatgaaatt  1560
gtggttgaag ccgatagcaa agaagcacag atctggcaa aactgattaa agaaaaatg  1620
gaagaagcct gggattggtg tctggaaaaa gccgaagaat ttggtaatcg tgtggccaaa  1680
atcaaactgg aagttgagga gccgcatgtt ggtaatacct gggaaaaacc gtaa        1734
```

<210> SEQ ID NO 2
<211> LENGTH: 577
<212> TYPE: PRT
<213> ORGANISM: Artificial Sequence
<220> FEATURE:
<223> OTHER INFORMATION: M66 PRT

<400> SEQUENCE: 2

```
Met Asn Thr Pro Lys Pro Ile Leu Lys Pro Gln Ser Lys Ala Leu Val
1               5                   10                  15

Glu Pro Val Leu Cys Asn Ser Ile Asp Glu Ile Pro Ala Lys Tyr Asn
            20                  25                  30

Glu Pro Ile Tyr Phe Asp Leu Ala Thr Asp Glu Asp Arg Pro Val Leu
        35                  40                  45

Ala Ser Ile Tyr Gln Pro His Phe Glu Arg Lys Val Tyr Cys Leu Asn
    50                  55                  60

Leu Leu Lys Glu Asn Pro Glu Arg Phe Lys Glu Trp Leu Leu Lys Phe
65                  70                  75                  80

Ser Glu Ile Arg Gly Trp Gly Leu Asp Phe Asp Leu Arg Val Leu Gly
                85                  90                  95

Tyr Thr Tyr Glu Gln Leu Arg Asn Lys Lys Ile Ile Asp Val Gln Leu
            100                 105                 110

Ala Leu Lys Val Gln His Tyr Glu Arg Phe Lys Gln Asn Gly Ala Lys
        115                 120                 125

Gly Glu Gly Phe Arg Leu Asp Asp Val Ala Arg Asp Leu Leu Gly Ile
    130                 135                 140

Glu Tyr Pro Met Asn Lys Thr Lys Ile Arg Thr Thr Phe Lys Tyr Asn
145                 150                 155                 160

Met Tyr Ser Ser Phe Ser Tyr Glu Gln Leu Leu Tyr Ala Ser Leu Asp
                165                 170                 175

Ala Tyr Ile Pro His Leu Leu Tyr Glu Arg Leu Ser Ser Asp Thr Leu
            180                 185                 190
```

Asn Ser Leu Val Tyr Gln Ile Asp Gln Glu Val Gln Lys Val Val Ile
            195                 200                 205

Glu Thr Ser Gln His Gly Met Pro Val Lys Leu Lys Ala Leu Glu Glu
210                 215                 220

Glu Ile His Arg Leu Thr Gln Leu Arg Ser Glu Met Gln Lys Gln Ile
225                 230                 235                 240

Pro Phe Asn Tyr Asn Ser Pro Lys Gln Thr Ala Lys Phe Phe Gly Val
            245                 250                 255

Asn Ser Ser Ser Lys Asp Val Leu Met Asp Leu Ala Leu Arg Gly Asn
        260                 265                 270

Glu Val Ala Lys Lys Val Leu Glu Ala Arg Gln Ile Glu Lys Ser Leu
    275                 280                 285

Ala Phe Ala Lys Asp Leu Tyr Asp Ile Ala Lys Lys Asn Gly Gly Arg
290                 295                 300

Ile Tyr Gly Asn Phe Phe Thr Thr Thr Ala Pro Ser Gly Arg Met Ser
305                 310                 315                 320

Cys Ser Asp Ile Asn Leu Gln Gln Ile Pro Arg Arg Leu Arg Pro Phe
            325                 330                 335

Ile Gly Phe Glu Thr Glu Asp Lys Lys Leu Ile Thr Ala Asp Phe Pro
        340                 345                 350

Gln Ile Glu Leu Arg Leu Ala Gly Val Ile Trp Asp Glu Pro Lys Phe
    355                 360                 365

Ile Glu Ala Phe Arg Gln Gly Ile Asp Leu His Lys Leu Thr Ala Ser
370                 375                 380

Ile Leu Phe Asp Lys Asn Ile Glu Glu Val Ser Lys Glu Glu Arg Gln
385                 390                 395                 400

Ile Gly Lys Ser Ala Asn Phe Gly Leu Ile Tyr Gly Ile Ser Pro Lys
            405                 410                 415

Gly Phe Ala Glu Tyr Cys Ile Ser Asn Gly Ile Asn Ile Thr Glu Glu
        420                 425                 430

Met Ala Ile Glu Ile Val Lys Lys Trp Lys Lys Phe Tyr Arg Lys Ile
    435                 440                 445

Ala Glu Gln His Gln Leu Ala Tyr Glu Arg Phe Lys Tyr Ala Glu Phe
450                 455                 460

Val Asp Asn Glu Thr Trp Leu Asn Arg Thr Tyr Arg Ala Trp Lys Pro
465                 470                 475                 480

Gln Asp Leu Leu Asn Tyr Gln Ile Gln Gly Ser Gly Ala Glu Leu Phe
            485                 490                 495

Lys Lys Ala Ile Ile Leu Leu Lys Glu Ala Lys Pro Asp Leu Lys Ile
        500                 505                 510

Val Asn Leu Val His Asp Glu Ile Val Val Glu Ala Asp Ser Lys Glu
    515                 520                 525

Ala Gln Asp Leu Ala Lys Leu Ile Lys Glu Lys Met Glu Glu Ala Trp
530                 535                 540

Asp Trp Cys Leu Glu Lys Ala Glu Glu Phe Gly Asn Arg Val Ala Lys
545                 550                 555                 560

Ile Lys Leu Glu Val Glu Glu Pro His Val Gly Asn Thr Trp Glu Lys
            565                 570                 575

Pro

<210> SEQ ID NO 3
<211> LENGTH: 1734
<212> TYPE: DNA

<213> ORGANISM: Artificial Sequence
<220> FEATURE:
<223> OTHER INFORMATION: M160 DNA

<400> SEQUENCE: 3

```
atgaataccc cgaaaccgat tctgaaaccg cagagcaaag cactggttga acctgttctg      60
tgtgatagca ttgatgaaat tccggcaaaa tacaatgaac ctgtgtattt tgatctggca     120
accgatgaag atcgtccggt tctggcaagc atttatcagc gcatttttga acgtaaagtg     180
tattgtctga atctgctgcg tgaaaaactg gcacgtttta agaatggct gctgaaattt      240
agcgaaattc gtggttgggg cttagatttc gatctgcgtg ttctgggtta tacctatgaa     300
cagctgcgca acaaaaaaat cgttgacgtc cagctggcca ttaaagtgca gcattatgaa     360
cgctttaaac aaggtggcac caaaggtgaa ggttttcgtc tggatgatgt tgcacgtgat     420
ctgctgggta ttgaatatcc gatgaacaaa acgaaaatcc gcaccacctt caagtataac     480
atgtatagca gctttcgta cgagcaactg ctgtatgcaa gcctggatgc atatattccg      540
catctgctgt acgaacgtct gagcagcgat accctgaata gcctggttta tcagattgat     600
caagaggttc agaaagtggg gattgaaacc agccagcatg gtatgccggt taaactgaaa     660
gcactggaag aagaaattca tcgtctgacc cagctgcgta gcgaaatgca gaaacaaatt     720
ccgtttaact ataatagccc gaaacagacc gccaaattct ttggtgttaa tagcagcagc     780
aaagatgttc tgatggatct ggcactgcgt ggtaatgaag ttgccaaaaa agttctggaa     840
gcacgccaga ttgaaaaaag tctggcattc gccaaagatc tgtatgatat cgccaaaaaa     900
aacggtggtc gcatctatgg taacttttttt accaccaccg caccgagcgg tcgtatgagc     960
tgtagcgata ttaacctgca gcaaattccg cgtcgtctgc gtccgtttat tggttttgaa    1020
accgaggaca aaaaactgat caccgcagat tttccgcaga ttgaactgcg tctggcaggc    1080
gttatgtgga atgaacctga atttctgaaa gcctttcgtg atggcattga tctgcacaaa    1140
ctgaccgcaa gtattctgtt cgataaaaag attaacgaag tgagcaaaga ggaacgccag    1200
atcggtaaaa gcgcaaattt tggtctgatt tatggtatca gcccgaaagg ttttgccgaa    1260
tattgtatta gcaacggcat taacatcacc gaagaaatgg caatcgagat cgtgaaaaaa    1320
tggaagaagt tctatcgcaa aatcgccgaa cagcatcagc tggcatatga acgtttcaaa    1380
tatgccgaat cgtggataa tgaaacctgg ctgaatcgtc cgtatcgtgc atggaaaccg    1440
caagatctgc tgaactatca gattcaaggt agcggtgcag aactgttcaa aaaagcaatt    1500
gttctgctga agaagccaa accggatctg aaaattgtga atctggttca cgatgaaatt    1560
gtggtggaaa ccagtaccga agaagcagaa gatattgcac tgctggtgaa acaaaagatg    1620
gaagaggcat gggattattg cctggaaaaa gcaaaagaat ttggcaataa cgtggccgac    1680
attaaactgg aagttgaaaa accgaatatt agcagcgtgt gggaaaaaga ataa          1734
```

<210> SEQ ID NO 4
<211> LENGTH: 577
<212> TYPE: PRT
<213> ORGANISM: Artificial Sequence
<220> FEATURE:
<223> OTHER INFORMATION: M160 PRT

<400> SEQUENCE: 4

```
Met Asn Thr Pro Lys Pro Ile Leu Lys Pro Gln Ser Lys Ala Leu Val
1               5                   10                  15

Glu Pro Val Leu Cys Asp Ser Ile Asp Glu Ile Pro Ala Lys Tyr Asn
            20                  25                  30
```

-continued

Glu Pro Val Tyr Phe Asp Leu Ala Thr Asp Glu Asp Arg Pro Val Leu
             35                  40                  45

Ala Ser Ile Tyr Gln Pro His Phe Glu Arg Lys Val Tyr Cys Leu Asn
 50                  55                  60

Leu Leu Arg Glu Lys Leu Ala Arg Phe Lys Glu Trp Leu Leu Lys Phe
 65                  70                  75                  80

Ser Glu Ile Arg Gly Trp Gly Leu Asp Phe Asp Leu Arg Val Leu Gly
                     85                  90                  95

Tyr Thr Tyr Glu Gln Leu Arg Asn Lys Lys Ile Val Asp Val Gln Leu
                 100                 105                 110

Ala Ile Lys Val Gln His Tyr Glu Arg Phe Lys Gln Gly Gly Thr Lys
             115                 120                 125

Gly Glu Gly Phe Arg Leu Asp Asp Val Ala Arg Asp Leu Leu Gly Ile
 130                 135                 140

Glu Tyr Pro Met Asn Lys Thr Lys Ile Arg Thr Thr Phe Lys Tyr Asn
145                 150                 155                 160

Met Tyr Ser Ser Phe Ser Tyr Glu Gln Leu Leu Tyr Ala Ser Leu Asp
                 165                 170                 175

Ala Tyr Ile Pro His Leu Leu Tyr Glu Arg Leu Ser Ser Asp Thr Leu
             180                 185                 190

Asn Ser Leu Val Tyr Gln Ile Asp Gln Glu Val Gln Lys Val Val Ile
         195                 200                 205

Glu Thr Ser Gln His Gly Met Pro Val Lys Leu Lys Ala Leu Glu Glu
 210                 215                 220

Glu Ile His Arg Leu Thr Gln Leu Arg Ser Glu Met Gln Lys Gln Ile
225                 230                 235                 240

Pro Phe Asn Tyr Asn Ser Pro Lys Gln Thr Ala Lys Phe Phe Gly Val
                 245                 250                 255

Asn Ser Ser Ser Lys Asp Val Leu Met Asp Leu Ala Leu Arg Gly Asn
             260                 265                 270

Glu Val Ala Lys Lys Val Leu Glu Ala Arg Gln Ile Glu Lys Ser Leu
         275                 280                 285

Ala Phe Ala Lys Asp Leu Tyr Asp Ile Ala Lys Lys Asn Gly Gly Arg
 290                 295                 300

Ile Tyr Gly Asn Phe Phe Thr Thr Thr Ala Pro Ser Gly Arg Met Ser
305                 310                 315                 320

Cys Ser Asp Ile Asn Leu Gln Gln Ile Pro Arg Arg Leu Arg Pro Phe
                 325                 330                 335

Ile Gly Phe Glu Thr Glu Asp Lys Lys Leu Ile Thr Ala Asp Phe Pro
             340                 345                 350

Gln Ile Glu Leu Arg Leu Ala Gly Val Met Trp Asn Glu Pro Glu Phe
         355                 360                 365

Leu Lys Ala Phe Arg Asp Gly Ile Asp Leu His Lys Leu Thr Ala Ser
 370                 375                 380

Ile Leu Phe Asp Lys Lys Ile Asn Glu Val Ser Lys Glu Glu Arg Gln
385                 390                 395                 400

Ile Gly Lys Ser Ala Asn Phe Gly Leu Ile Tyr Gly Ile Ser Pro Lys
                 405                 410                 415

Gly Phe Ala Glu Tyr Cys Ile Ser Asn Gly Ile Asn Ile Thr Glu Glu
             420                 425                 430

Met Ala Ile Glu Ile Val Lys Lys Trp Lys Lys Phe Tyr Arg Lys Ile
         435                 440                 445

```
Ala Glu Gln His Gln Leu Ala Tyr Glu Arg Phe Lys Tyr Ala Glu Phe
            450                 455                 460

Val Asp Asn Glu Thr Trp Leu Asn Arg Pro Tyr Arg Ala Trp Lys Pro
465                 470                 475                 480

Gln Asp Leu Leu Asn Tyr Gln Ile Gln Gly Ser Gly Ala Glu Leu Phe
                485                 490                 495

Lys Lys Ala Ile Val Leu Leu Lys Glu Ala Lys Pro Asp Leu Lys Ile
                500                 505                 510

Val Asn Leu Val His Asp Glu Ile Val Val Glu Thr Ser Thr Glu Glu
            515                 520                 525

Ala Glu Asp Ile Ala Leu Leu Val Lys Gln Lys Met Glu Glu Ala Trp
530                 535                 540

Asp Tyr Cys Leu Glu Lys Ala Lys Glu Phe Gly Asn Asn Val Ala Asp
545                 550                 555                 560

Ile Lys Leu Glu Val Glu Lys Pro Asn Ile Ser Ser Val Trp Glu Lys
                565                 570                 575

Glu
```

<210> SEQ ID NO 5
<211> LENGTH: 1734
<212> TYPE: DNA
<213> ORGANISM: Artificial Sequence
<220> FEATURE:
<223> OTHER INFORMATION: M180 DNA

<400> SEQUENCE: 5

```
atgaataccc cgaaaccgat tctgaaaccg cagccgaagg ccttggttga acctgttctg      60
tgtgatagca ttgatgaaat tccggcacgc tttgatgagg tgatctattt tgatctggca     120
accgatgaag atcgtccggt tctggcaagc atttatcagc gcatttttga acgtaaagtg     180
tattgtctga atctgctgcg tgaaaaactg gcacgttttta agaatggct gctgaaattt     240 agcgaaattc gtggttgggg cttagatttc gatctgcgtg ttctgggttt tacctatgaa     300
cagctgaaga caaaaaaat cattgatgtt cagctggccc tgaaagtgca gcattatgaa     360
cgctttaaac aaggtggcac caaaggtgaa ggttttcgtc tggatgatgt tgcacgtgat     420
ctgctgggta ttgaatatcc gatgaacaaa accaaaatcc gcgaaacctt caaaacaac     480 atgtttcaca gctttagcaa cgagcaactg ctgtatgcaa gctttgatgc atatattccg     540
catctgctgt acgaacagct gaccagcagc accctgaata gcctggttta tcagctggat     600
cagcaggcac agaaaattgt tattgaaacc agccagcatg gtatgccggt taaactgaaa     660
gccctggaag aagaaattca tcgtctgacc cagctgcgtt cagaaatgca gcgtcagatt     720
ccgtttaact ataatagccc gaaacagacc gcaaaattct tggtgttga tagcagcagc     780 aaagatgttc tgatggatct ggcactgcag ggtaatgaaa tggcaaaaaa agtactggaa     840
gcccgtcaga ttgaaaaaag cctggcattt gcaaagacc tgtatgatat tgcaaaacgt     900
agcggtggtc gcatttatgg caactttttc accaccaccg caccgagcgg tcgtatgagc     960
tgtagcgata ttaatctgca gcaaattccg cgtcgtctgc gtagctttat tggttttgat    1020
accgaagata aaaaactgat taccgcagat tttccgcaga ttgaactgcg tctggcaggc    1080
gttatgtgga atgaacctga atttctgaaa gcctttcgtg atggcattga tctgcacaaa    1140
ctgaccgcaa gcattctgtt cgataaaag attaacgaag tgagcaaaga ggaacgccag    1200
atcggtaaaa gcgcaaattt tggtctgatt tatggtatca gcccgaaagg ttttgccgaa    1260
tattgtatta gcaacggcat taacatcacc gaagaaatgg caatcgagat cgtgaaaaaa    1320
```

```
tggaagaagt tctatcgcaa aatcgccgaa cagcatcagc tggcatatga acgtttcaaa    1380
tatgccgaat tcgtggataa tgaaacctgg ctgaatcgtc cgtatcgtgc atataaaccg    1440
caggacctgc tgaactatca gattcaaggt agcggtgcag aactgttcaa aaaagcaatt    1500
gtgctgctga agaaaccaa accggatctg aaaattgtga atctggtgca tgatgaaatt    1560
gtggttgaag ccgatagcaa agaagcacag atctggcaa aactgattaa agaaaaaatg    1620
gaagaagcct gggattggtg tctggaaaaa gccgaagaat ttggtaatcg tgtggccaaa    1680
atcaaactgg aagttgagga ccgcatgtt ggtaataccct gggaaaaaacc gtaa         1734
```

<210> SEQ ID NO 6
<211> LENGTH: 577
<212> TYPE: PRT
<213> ORGANISM: Artificial Sequence
<220> FEATURE:
<223> OTHER INFORMATION: M180 PRT

<400> SEQUENCE: 6

```
Met Asn Thr Pro Lys Pro Ile Leu Lys Pro Gln Pro Lys Ala Leu Val
1               5                   10                  15

Glu Pro Val Leu Cys Asp Ser Ile Asp Glu Ile Pro Ala Arg Phe Asp
            20                  25                  30

Glu Val Ile Tyr Phe Asp Leu Ala Thr Asp Glu Asp Arg Pro Val Leu
        35                  40                  45

Ala Ser Ile Tyr Gln Pro His Phe Glu Arg Lys Val Tyr Cys Leu Asn
    50                  55                  60

Leu Leu Arg Glu Lys Leu Ala Arg Phe Lys Glu Trp Leu Leu Lys Phe
65                  70                  75                  80

Ser Glu Ile Arg Gly Trp Gly Leu Asp Phe Asp Leu Arg Val Leu Gly
                85                  90                  95

Phe Thr Tyr Glu Gln Leu Lys Asn Lys Lys Ile Ile Asp Val Gln Leu
            100                 105                 110

Ala Leu Lys Val Gln His Tyr Glu Arg Phe Lys Gln Gly Gly Thr Lys
        115                 120                 125

Gly Glu Gly Phe Arg Leu Asp Asp Val Ala Arg Asp Leu Leu Gly Ile
    130                 135                 140

Glu Tyr Pro Met Asn Lys Thr Lys Ile Arg Glu Thr Phe Lys Asn Asn
145                 150                 155                 160

Met Phe His Ser Phe Ser Asn Glu Gln Leu Leu Tyr Ala Ser Phe Asp
                165                 170                 175

Ala Tyr Ile Pro His Leu Leu Tyr Glu Leu Thr Ser Ser Thr Leu
            180                 185                 190

Asn Ser Leu Val Tyr Gln Leu Asp Gln Gln Ala Gln Lys Ile Val Ile
        195                 200                 205

Glu Thr Ser Gln His Gly Met Pro Val Lys Leu Lys Ala Leu Glu Glu
    210                 215                 220

Glu Ile His Arg Leu Thr Gln Leu Arg Ser Glu Met Gln Arg Gln Ile
225                 230                 235                 240

Pro Phe Asn Tyr Asn Ser Pro Lys Gln Thr Ala Lys Phe Phe Gly Val
                245                 250                 255

Asp Ser Ser Lys Asp Val Leu Met Asp Leu Ala Leu Gln Gly Asn
            260                 265                 270

Glu Met Ala Lys Lys Val Leu Glu Ala Arg Gln Ile Glu Lys Ser Leu
        275                 280                 285
```

```
Ala Phe Ala Lys Asp Leu Tyr Asp Ile Ala Lys Arg Ser Gly Gly Arg
    290                 295                 300
Ile Tyr Gly Asn Phe Phe Thr Thr Thr Ala Pro Ser Gly Arg Met Ser
305                 310                 315                 320
Cys Ser Asp Ile Asn Leu Gln Gln Ile Pro Arg Arg Leu Arg Ser Phe
                325                 330                 335
Ile Gly Phe Asp Thr Glu Asp Lys Lys Leu Ile Thr Ala Asp Phe Pro
            340                 345                 350
Gln Ile Glu Leu Arg Leu Ala Gly Val Met Trp Asn Glu Pro Glu Phe
        355                 360                 365
Leu Lys Ala Phe Arg Asp Gly Ile Asp Leu His Lys Leu Thr Ala Ser
    370                 375                 380
Ile Leu Phe Asp Lys Lys Ile Asn Glu Val Ser Lys Glu Glu Arg Gln
385                 390                 395                 400
Ile Gly Lys Ser Ala Asn Phe Gly Leu Ile Tyr Gly Ile Ser Pro Lys
                405                 410                 415
Gly Phe Ala Glu Tyr Cys Ile Ser Asn Gly Ile Asn Ile Thr Glu Glu
            420                 425                 430
Met Ala Ile Glu Ile Val Lys Lys Trp Lys Lys Phe Tyr Arg Lys Ile
        435                 440                 445
Ala Glu Gln His Gln Leu Ala Tyr Glu Arg Phe Lys Tyr Ala Glu Phe
    450                 455                 460
Val Asp Asn Glu Thr Trp Leu Asn Arg Pro Tyr Arg Ala Tyr Lys Pro
465                 470                 475                 480
Gln Asp Leu Leu Asn Tyr Gln Ile Gln Gly Ser Gly Ala Glu Leu Phe
                485                 490                 495
Lys Lys Ala Ile Val Leu Leu Lys Glu Thr Lys Pro Asp Leu Lys Ile
            500                 505                 510
Val Asn Leu Val His Asp Glu Ile Val Val Glu Ala Asp Ser Lys Glu
        515                 520                 525
Ala Gln Asp Leu Ala Lys Leu Ile Lys Glu Lys Met Glu Glu Ala Trp
    530                 535                 540
Asp Trp Cys Leu Glu Lys Ala Glu Glu Phe Gly Asn Arg Val Ala Lys
545                 550                 555                 560
Ile Lys Leu Glu Val Glu Glu Pro His Val Gly Asn Thr Trp Glu Lys
                565                 570                 575
Pro

<210> SEQ ID NO 7
<211> LENGTH: 1734
<212> TYPE: DNA
<213> ORGANISM: Artificial Sequence
<220> FEATURE:
<223> OTHER INFORMATION: M295 DNA

<400> SEQUENCE: 7
atgaataccc cgaaaccgat tctgaaaccg cagccgaagg ccttggttga acctgttctg      60
tgtgatagca ttgatgaaat tccggcaaaa tacaatgaac ctgtgtattt tgatctggca     120
accgatgaag atagaccggt tctggcaagc atttatcagc gcatttttga acgtaaagtg     180
tattgtctga atctgctgaa agaaaaagtg gcacgcttta agattggct gctgaaattt      240 agcgaaattc gtggttgggg cttagatttc gatctgcgtg ttctgggtta tacctatgaa     300
cagctgcgca caaaaaaaat cgttgacgtc cagctggcca ttaaagtgca gcattatgaa     360
cgttttaaac agggtggcac caaaggtgaa ggttttcgtc tggatgatgt tgcacgtgat     420
```

-continued

```
ctgctgggta ttgaatatcc gatgaacaaa acgaaaatcc gcaccacctt caagtataac      480
atgtatagca gcttttcgta cgagcaactg ctgtatgcaa gcctggatgc atatattccg      540
catctgctgt acgaacgtct gagcagcgat accctgaata gcctggttta tcagattgat      600
caagaggttc agaaagtggt gattgaaacc agccagcatg gtatgccggt taaactgcag      660
gcactggaag aagaaattca tcgtctgatt cagctgcgtt cagaaatgca gcgtcagatt      720
ccgtttaact ataatagccc gaaacagacc gcaaaattct tggtgttgta gcagcagc        780 aaagatgttc tgatggatct ggcactgcgt ggtaatgaag ttgccaaaaa agttctggaa      840
gcacgccaga ttgaaaaaag tctggcattc gccaaagatc tgtatgatat cgccaaaaaa      900
aacggtggtc gcatctatgg taacttttt accaccaccg caccgagcgg tcgtatgagc       960
tgtagcgata ttaacctgca gcaaattccg cgtcgtctgc gtagctttat tggttttgat      1020
accgaagata aaaactgat taccgcagat tttccgcaga ttgaactgcg tctggcaggc       1080
gttatttgga tgaaccgaa attcattgaa gcctttcgcc agggtattga tctgcataaa       1140
ctgaccgcta gcattctgtt tgataaaaac attgaagaag tgagcaaaga agaacgccag      1200
attggtaaaa gcgcaaattt tggtctgatt tatggtatca gcccgaaagg ttttgccgaa      1260
tattgtatta gcaacggcat taacatcacc gaagaaatgg caatcgagat cgtgaaaaaa      1320
tggaagaagt tctatcgcaa aatcgccgaa cagcatcagc tggcatatga acgtttcaaa      1380
tatgccgaat tcgtggataa tgaaacctgg ctgaatcgtc cgtatcgtgc atataaaccg      1440
caggacctgc tgaactatca gattcagggt agcggtgcag aactgttcaa aaaagcaatt      1500
gttctgctga agaagccaa accggatctg aaaattgtga atctggttca cgatgaaatt       1560
gtggtggaag cagatagtaa agaagcacag gatctggcca aactgatcaa agaaaagatg      1620
gaagaggcat gggattggtg tctggaaaaa gccgaagaat ttggtaatcg tgtggccaaa      1680
atcaaactgg aagttgaaga accgaatgtg ggtaatacct gggaaaaacc gtaa           1734
```

<210> SEQ ID NO 8
<211> LENGTH: 577
<212> TYPE: PRT
<213> ORGANISM: Artificial Sequence
<220> FEATURE:
<223> OTHER INFORMATION: M295 PRT

<400> SEQUENCE: 8

```
Met Asn Thr Pro Lys Pro Ile Leu Lys Pro Gln Pro Lys Ala Leu Val
1               5                   10                  15

Glu Pro Val Leu Cys Asp Ser Ile Asp Glu Ile Pro Ala Lys Tyr Asn
            20                  25                  30

Glu Pro Val Tyr Phe Asp Leu Ala Thr Asp Glu Asp Arg Pro Val Leu
        35                  40                  45

Ala Ser Ile Tyr Gln Pro His Phe Glu Arg Lys Val Tyr Cys Leu Asn
    50                  55                  60

Leu Leu Lys Glu Lys Val Ala Arg Phe Lys Asp Trp Leu Leu Lys Phe
65                  70                  75                  80

Ser Glu Ile Arg Gly Trp Gly Leu Asp Phe Asp Leu Arg Val Leu Gly
                85                  90                  95

Tyr Thr Tyr Glu Gln Leu Arg Asn Lys Lys Ile Val Asp Val Gln Leu
            100                 105                 110

Ala Ile Lys Val Gln His Tyr Glu Arg Phe Lys Gln Gly Gly Thr Lys
        115                 120                 125
```

-continued

Gly Glu Gly Phe Arg Leu Asp Asp Val Ala Arg Asp Leu Leu Gly Ile
130                 135                 140

Glu Tyr Pro Met Asn Lys Thr Lys Ile Arg Thr Thr Phe Lys Tyr Asn
145                 150                 155                 160

Met Tyr Ser Ser Phe Ser Tyr Glu Gln Leu Leu Tyr Ala Ser Leu Asp
                165                 170                 175

Ala Tyr Ile Pro His Leu Leu Tyr Glu Arg Leu Ser Ser Asp Thr Leu
            180                 185                 190

Asn Ser Leu Val Tyr Gln Ile Asp Gln Glu Val Gln Lys Val Val Ile
        195                 200                 205

Glu Thr Ser Gln His Gly Met Pro Val Lys Leu Gln Ala Leu Glu Glu
210                 215                 220

Glu Ile His Arg Leu Ile Gln Leu Arg Ser Glu Met Gln Arg Gln Ile
225                 230                 235                 240

Pro Phe Asn Tyr Asn Ser Pro Lys Gln Thr Ala Lys Phe Phe Gly Val
                245                 250                 255

Asp Ser Ser Lys Asp Val Leu Met Asp Leu Ala Leu Arg Gly Asn
            260                 265                 270

Glu Val Ala Lys Lys Val Leu Glu Ala Arg Gln Ile Glu Lys Ser Leu
        275                 280                 285

Ala Phe Ala Lys Asp Leu Tyr Asp Ile Ala Lys Lys Asn Gly Gly Arg
290                 295                 300

Ile Tyr Gly Asn Phe Phe Thr Thr Thr Ala Pro Ser Gly Arg Met Ser
305                 310                 315                 320

Cys Ser Asp Ile Asn Leu Gln Gln Ile Pro Arg Arg Leu Arg Ser Phe
                325                 330                 335

Ile Gly Phe Asp Thr Glu Asp Lys Lys Leu Ile Thr Ala Asp Phe Pro
            340                 345                 350

Gln Ile Glu Leu Arg Leu Ala Gly Val Ile Trp Asn Glu Pro Lys Phe
        355                 360                 365

Ile Glu Ala Phe Arg Gln Gly Ile Asp Leu His Lys Leu Thr Ala Ser
370                 375                 380

Ile Leu Phe Asp Lys Asn Ile Glu Glu Val Ser Lys Glu Glu Arg Gln
385                 390                 395                 400

Ile Gly Lys Ser Ala Asn Phe Gly Leu Ile Tyr Gly Ile Ser Pro Lys
                405                 410                 415

Gly Phe Ala Glu Tyr Cys Ile Ser Asn Gly Ile Asn Ile Thr Glu Glu
            420                 425                 430

Met Ala Ile Glu Ile Val Lys Lys Trp Lys Lys Phe Tyr Arg Lys Ile
        435                 440                 445

Ala Glu Gln His Gln Leu Ala Tyr Glu Arg Phe Lys Tyr Ala Glu Phe
450                 455                 460

Val Asp Asn Glu Thr Trp Leu Asn Arg Pro Tyr Arg Ala Tyr Lys Pro
465                 470                 475                 480

Gln Asp Leu Leu Asn Tyr Gln Ile Gln Gly Ser Gly Ala Glu Leu Phe
                485                 490                 495

Lys Lys Ala Ile Val Leu Leu Lys Glu Ala Lys Pro Asp Leu Lys Ile
            500                 505                 510

Val Asn Leu Val His Asp Glu Ile Val Glu Ala Asp Ser Lys Glu
        515                 520                 525

Ala Gln Asp Leu Ala Lys Leu Ile Lys Glu Lys Met Glu Glu Ala Trp
530                 535                 540

Asp Trp Cys Leu Glu Lys Ala Glu Glu Phe Gly Asn Arg Val Ala Lys 545              550              555              560

Ile Lys Leu Glu Val Glu Glu Pro Asn Val Gly Asn Thr Trp Glu Lys
            565              570              575

Pro

<210> SEQ ID NO 9
<211> LENGTH: 1734
<212> TYPE: DNA
<213> ORGANISM: Artificial Sequence
<220> FEATURE:
<223> OTHER INFORMATION: M384 DNA

<400> SEQUENCE: 9

```
atgaatgccc cgaaaccgat tctgaaaccg cagccgaagg ccttggttga acctgttctg     60
tgtaatagca ttaatgaaat tccggcaaaa tacaacgagc cgatctattt tgatctggta    120
accgatgaaa atcgtccgac actggcaagc ctgtatcagc cgggctttgg tcgtaaagtt    180
tattgtctga atctgctgcg tgaaaaactg gcacgtttta agaatggctg ctgaaatttt    240
agcgaaattc gtggttgggg cttagatttc gatctgcgtg ttctggggtta acctatgaa    300
cagctgcgta caaaaaaaat cattgatgtt cagctggccc tgaaagtgca gcattatgaa    360
cgctttaaac aaggtggcac caaaggtgaa ggttttcgtc tggatgatgt tgcacgtgat    420
ctgctgggta ttgaatatcc gatgaacaaa accaaaatcc gcgaaacctt caaaaacaac    480
atgtttcaca gctttagcaa cgagcaactg ctgtatgcaa gctttgatgc atatattccg    540
catctgctgt acgaacagct gaccagcagc accctgaata gcctggtttta tcagctggat    600
cagcaggcac agaaaattgt tattgaaacc agccagcatg gtatgccggt taaactgaaa    660
gcactggaag aagaaattca tcgtctgacc cagctgcgta gcgaaatgca gaaacaaatt    720
ccgtttaact ataatagccc gaaacagacc gccaaattct ttggtgttaa tagcagcagc    780
aaagatgtgc tgatggatct ggcactgcag ggtaatgaaa tggcaaaaaa agtactggaa    840
gcccgtcaga ttgaaaaaag cctggcattt gcaaagacc  tgtatgatat tgcaaaacgt    900
agcggtggtc gcatttatgg caactttttt accaccaccg caccaagtgg ccgtatgagc    960
tgtagcgata ttaatctgca gcaaattccg cgtcgtctgc gtagctttat tggttttgat   1020
accgaagata aaaaactgat taccgcagat tttccgcaga ttgaactgcg tctggcaggc   1080
gttattttgga atgaaccgaa attcattgaa gcctttcgcc agggtattga tctgcataaa   1140
ctgaccgcta gcattctgtt tgataaaaac attgaagaag tgagcaaaga gaacgccag    1200
attggtaaaa gcgcaaattt tggtctgatt tatggtatca gcccgaaagg ttttgccgaa   1260
tattgtatta gcaacggcat taacatcacc gaagaaatgg caatcgagat cgtgaaaaaa   1320
tggaagaagt tctatcgcaa aatcgccgaa agcatcagc  tggcatatga acgtttcaaa   1380
tatgccgaat tcgtggataa tgaaacctgg ctgaatcgtc cgtatcgtgc atataaaccg   1440
caggacctgc tgaactatca gattcaaggt agcggtgcag aactgttcaa aaaagcaatt   1500
gttctgctga agaagccaa  accggatctg aaaattgtga atctggttca cgatgaaatt   1560
gtggtggaag cagatagtaa agaagcacag gatctggcca aactgatcaa agaaaagatg   1620
gaagaggcat gggattggtg tctggaaaaa gccgaagaat tggtaatcg tgtggccaaa   1680
atcaaactgg aagttgagga ccgcatgttt ggtaatacct gggaaaaacc gtaa          1734
```

<210> SEQ ID NO 10
<211> LENGTH: 577
<212> TYPE: PRT

<213> ORGANISM: Artificial Sequence
<220> FEATURE:
<223> OTHER INFORMATION: M384 PRT

<400> SEQUENCE: 10

| | | | | | | | | | | | | | | | |
|---|---|---|---|---|---|---|---|---|---|---|---|---|---|---|---|
| Met | Asn | Ala | Pro | Lys | Pro | Ile | Leu | Lys | Pro | Gln | Pro | Lys | Ala | Leu | Val |
| 1 | | | | 5 | | | | | 10 | | | | | 15 | |
| Glu | Pro | Val | Leu | Cys | Asn | Ser | Ile | Asn | Glu | Ile | Pro | Ala | Lys | Tyr | Asn |
| | | | 20 | | | | | 25 | | | | | 30 | | |
| Glu | Pro | Ile | Tyr | Phe | Asp | Leu | Val | Thr | Asp | Glu | Asn | Arg | Pro | Thr | Leu |
| | | | 35 | | | | 40 | | | | | 45 | | | |
| Ala | Ser | Leu | Tyr | Gln | Pro | Gly | Phe | Gly | Arg | Lys | Val | Tyr | Cys | Leu | Asn |
| | 50 | | | | | 55 | | | | | 60 | | | | |
| Leu | Leu | Arg | Glu | Lys | Leu | Ala | Arg | Phe | Lys | Glu | Trp | Leu | Leu | Lys | Phe |
| 65 | | | | | 70 | | | | | 75 | | | | | 80 |
| Ser | Glu | Ile | Arg | Gly | Trp | Gly | Leu | Asp | Phe | Asp | Leu | Arg | Val | Leu | Gly |
| | | | | 85 | | | | | 90 | | | | | 95 | |
| Tyr | Thr | Tyr | Glu | Gln | Leu | Arg | Asn | Lys | Lys | Ile | Ile | Asp | Val | Gln | Leu |
| | | | 100 | | | | | 105 | | | | | 110 | | |
| Ala | Leu | Lys | Val | Gln | His | Tyr | Glu | Arg | Phe | Lys | Gln | Gly | Gly | Thr | Lys |
| | | 115 | | | | | 120 | | | | | 125 | | | |
| Gly | Glu | Gly | Phe | Arg | Leu | Asp | Asp | Val | Ala | Arg | Asp | Leu | Leu | Gly | Ile |
| | 130 | | | | | 135 | | | | | 140 | | | | |
| Glu | Tyr | Pro | Met | Asn | Lys | Thr | Lys | Ile | Arg | Glu | Thr | Phe | Lys | Asn | Asn |
| 145 | | | | | 150 | | | | | 155 | | | | | 160 |
| Met | Phe | His | Ser | Phe | Ser | Asn | Glu | Gln | Leu | Leu | Tyr | Ala | Ser | Phe | Asp |
| | | | | 165 | | | | | 170 | | | | | 175 | |
| Ala | Tyr | Ile | Pro | His | Leu | Leu | Tyr | Glu | Gln | Leu | Thr | Ser | Ser | Thr | Leu |
| | | | 180 | | | | | 185 | | | | | 190 | | |
| Asn | Ser | Leu | Val | Tyr | Gln | Leu | Asp | Gln | Gln | Ala | Gln | Lys | Ile | Val | Ile |
| | | | 195 | | | | | 200 | | | | | 205 | | |
| Glu | Thr | Ser | Gln | His | Gly | Met | Pro | Val | Lys | Leu | Lys | Ala | Leu | Glu | Glu |
| | 210 | | | | | 215 | | | | | 220 | | | | |
| Glu | Ile | His | Arg | Leu | Thr | Gln | Leu | Arg | Ser | Glu | Met | Gln | Lys | Gln | Ile |
| 225 | | | | | 230 | | | | | 235 | | | | | 240 |
| Pro | Phe | Asn | Tyr | Asn | Ser | Pro | Lys | Gln | Thr | Ala | Lys | Phe | Phe | Gly | Val |
| | | | | 245 | | | | | 250 | | | | | 255 | |
| Asn | Ser | Ser | Ser | Lys | Asp | Val | Leu | Met | Asp | Leu | Ala | Leu | Gln | Gly | Asn |
| | | | 260 | | | | | 265 | | | | | 270 | | |
| Glu | Met | Ala | Lys | Lys | Val | Leu | Glu | Ala | Arg | Gln | Ile | Glu | Lys | Ser | Leu |
| | | 275 | | | | | 280 | | | | | 285 | | | |
| Ala | Phe | Ala | Lys | Asp | Leu | Tyr | Asp | Ile | Ala | Lys | Arg | Ser | Gly | Gly | Arg |
| | 290 | | | | | 295 | | | | | 300 | | | | |
| Ile | Tyr | Gly | Asn | Phe | Phe | Thr | Thr | Thr | Ala | Pro | Ser | Gly | Arg | Met | Ser |
| 305 | | | | | 310 | | | | | 315 | | | | | 320 |
| Cys | Ser | Asp | Ile | Asn | Leu | Gln | Gln | Ile | Pro | Arg | Arg | Leu | Arg | Ser | Phe |
| | | | | 325 | | | | | 330 | | | | | 335 | |
| Ile | Gly | Phe | Asp | Thr | Glu | Asp | Lys | Lys | Leu | Ile | Thr | Ala | Asp | Phe | Pro |
| | | | 340 | | | | | 345 | | | | | 350 | | |
| Gln | Ile | Glu | Leu | Arg | Leu | Ala | Gly | Val | Ile | Trp | Asn | Glu | Pro | Lys | Phe |
| | | 355 | | | | | 360 | | | | | 365 | | | |
| Ile | Glu | Ala | Phe | Arg | Gln | Gly | Ile | Asp | Leu | His | Lys | Leu | Thr | Ala | Ser |
| | 370 | | | | | 375 | | | | | 380 | | | | |
| Ile | Leu | Phe | Asp | Lys | Asn | Ile | Glu | Glu | Val | Ser | Lys | Glu | Glu | Arg | Gln |

Ile Gly Lys Ser Ala Asn Phe Gly Leu Ile Tyr Gly Ile Ser Pro Lys
385                 390                 395                 400
            405                 410                 415

Gly Phe Ala Glu Tyr Cys Ile Ser Asn Gly Ile Asn Ile Thr Glu Glu
            420                 425                 430

Met Ala Ile Glu Ile Val Lys Lys Trp Lys Lys Phe Tyr Arg Lys Ile
            435                 440                 445

Ala Glu Gln His Gln Leu Ala Tyr Glu Arg Phe Lys Tyr Ala Glu Phe
            450                 455                 460

Val Asp Asn Glu Thr Trp Leu Asn Arg Pro Tyr Arg Ala Tyr Lys Pro
465                 470                 475                 480

Gln Asp Leu Leu Asn Tyr Gln Ile Gln Gly Ser Gly Ala Glu Leu Phe
            485                 490                 495

Lys Lys Ala Ile Val Leu Leu Lys Glu Ala Lys Pro Asp Leu Lys Ile
            500                 505                 510

Val Asn Leu Val His Asp Glu Ile Val Val Glu Ala Asp Ser Lys Glu
            515                 520                 525

Ala Gln Asp Leu Ala Lys Leu Ile Lys Glu Lys Met Glu Glu Ala Trp
            530                 535                 540

Asp Trp Cys Leu Glu Lys Ala Glu Glu Phe Gly Asn Arg Val Ala Lys
545                 550                 555                 560

Ile Lys Leu Glu Val Glu Glu Pro His Val Gly Asn Thr Trp Glu Lys
            565                 570                 575

Pro

<210> SEQ ID NO 11
<211> LENGTH: 1734
<212> TYPE: DNA
<213> ORGANISM: Artificial Sequence
<220> FEATURE:
<223> OTHER INFORMATION: M392 DNA

<400> SEQUENCE: 11

```
atgaataccc cgaaaccgat tctgaaaccg caaccgaagg ccttggttga acctgttctg    60
tgtgatagca ttgatgaaat tccggcaaaa tacaatgaac ctgtgtattt tgatctggca   120
accgatgaag atagaccggt tctggcaagc atttatcagc cgcattttga acgtaaagtg   180
tattgtctga atctgctgaa agaaaaagtg gcacgcttta agattggct gctgaaattt    240
agcgaaattc gtggttgggg cttagatttc gatctgcgtg ttctgggtta tcctatgaa    300
cagctgcgta caaaaaaat cattgatgtt cagctggccc tgaaagtgca gcattatgaa    360
cgctttaaac aaggtggcac caaaggtgaa ggttttcgtc tggatgatgt tgcacgtgat   420
ctgctgggta ttgaatatcc gatgaataaa accaaaattc gcgaaacctt taaaaacaat   480
atgtttcata gctttagcaa tgaacagctg ctgtatgcaa gcctggatgc atacattccg   540
catctgctgt atgaacagct gaccagcagc accctgaata gcctggttta tcagctggat   600
cagcaggcac agaaagttgt tattgaaact agtcagcatg gtatgtcggt taaactgaaa   660
gccctggaag aagaaattca tcgtctgacc cagctgcgtt cagaaatgca gcgtcagatt   720
ccgtttaact ataatagccc gaaacagacc gcaaaattct tggtgttga tagcagcagc    780
aaagatgttc tgatggatct ggcactgcgt ggtaatgaag ttgccaaaaa agttctggaa   840
gcacgccaga ttgaaaaaag tctggcattc gccaagatc tgtatgatat cgccaaaaaa    900
aacggtggtc gcatctatgg taactttttt accaccaccg caccgagcgg tcgtatgagc   960
```

```
tgtagcgata ttaacctgca gcaaattccg cgtcgtctgc gtccgtttat ggttttgaa    1020 accgaagata aaaagctgat caccgcagat tttccgcaga ttgaactgcg tctggcaggc    1080
gttatttggg atgaaccgaa atttatcgaa gcatttcgtc agggtatcga tctgcataaa    1140
ctgaccgcaa gcattctgtt cgataaaaac attgaagagg tgagcaaaga gaacgccag    1200 attggtaaaa gcgcaaattt tggtctgatc tatggtatca gcccgaaagg ttttgccgaa    1260
tattgtatta gcaacggcat taacatcacc gaagaaatgg caatcgagat cgtgaaaaaa    1320
tggaagaagt tctatcgcaa aatcgccgaa cagcatcagc tggcatatga acgtttcaaa    1380
tatgccgaat cgtggataaa tgaaacctgg ctgaatcgtc cgtatcgtgc atataaaccg    1440
caggacctgc tgaactatca gattcaaggt agcggtgcag aactgttcaa aaaagcaatt    1500
gtgctgctga agaaaccaa accggatctg aaaattgtga atctggtgca tgatgaaatt    1560
gtggttgaag ccgatagcaa agaagcacag gatctggcaa aactgattaa agaaaaaatg    1620
gaagaagcct gggattggtg tctggaaaaa gccgaagaat ttggtaatcg tgtggccaaa    1680
atcaaactgg aagttgagga gccgcatgtt ggtaatacct gggaaaaacc gtaa         1734
```

<210> SEQ ID NO 12
<211> LENGTH: 577
<212> TYPE: PRT
<213> ORGANISM: Artificial Sequence
<220> FEATURE:
<223> OTHER INFORMATION: M392 PRT

<400> SEQUENCE: 12

```
Met Asn Thr Pro Lys Pro Ile Leu Lys Pro Gln Pro Lys Ala Leu Val
1               5                   10                  15

Glu Pro Val Leu Cys Asp Ser Ile Asp Glu Ile Pro Ala Lys Tyr Asn
            20                  25                  30

Glu Pro Val Tyr Phe Asp Leu Ala Thr Asp Glu Asp Arg Pro Val Leu
        35                  40                  45

Ala Ser Ile Tyr Gln Pro His Phe Glu Arg Lys Val Tyr Cys Leu Asn
    50                  55                  60

Leu Leu Lys Glu Lys Val Ala Arg Phe Lys Asp Trp Leu Leu Lys Phe
65                  70                  75                  80

Ser Glu Ile Arg Gly Trp Gly Leu Asp Phe Asp Leu Arg Val Leu Gly
                85                  90                  95

Tyr Thr Tyr Glu Gln Leu Arg Asn Lys Lys Ile Ile Asp Val Gln Leu
            100                 105                 110

Ala Leu Lys Val Gln His Tyr Glu Arg Phe Lys Gln Gly Gly Thr Lys
        115                 120                 125

Gly Glu Gly Phe Arg Leu Asp Asp Val Ala Arg Asp Leu Leu Gly Ile
    130                 135                 140

Glu Tyr Pro Met Asn Lys Thr Lys Ile Arg Glu Thr Phe Lys Asn Asn
145                 150                 155                 160

Met Phe His Ser Phe Ser Asn Glu Gln Leu Leu Tyr Ala Ser Leu Asp
                165                 170                 175

Ala Tyr Ile Pro His Leu Leu Tyr Glu Gln Leu Thr Ser Ser Thr Leu
            180                 185                 190

Asn Ser Leu Val Tyr Gln Leu Asp Gln Gln Ala Gln Lys Val Val Ile
        195                 200                 205

Glu Thr Ser Gln His Gly Met Ser Val Lys Leu Lys Ala Leu Glu Glu
    210                 215                 220

Glu Ile His Arg Leu Thr Gln Leu Arg Ser Glu Met Gln Arg Gln Ile
```

225                 230                 235                 240

Pro Phe Asn Tyr Asn Ser Pro Lys Gln Thr Ala Lys Phe Phe Gly Val
                245                 250                 255

Asp Ser Ser Lys Asp Val Leu Met Asp Leu Ala Leu Arg Gly Asn
            260                 265                 270

Glu Val Ala Lys Lys Val Leu Glu Ala Arg Gln Ile Glu Lys Ser Leu
            275                 280                 285

Ala Phe Ala Lys Asp Leu Tyr Asp Ile Ala Lys Lys Asn Gly Gly Arg
290                 295                 300

Ile Tyr Gly Asn Phe Phe Thr Thr Ala Pro Ser Gly Arg Met Ser
305                 310                 315                 320

Cys Ser Asp Ile Asn Leu Gln Gln Ile Pro Arg Arg Leu Arg Pro Phe
                325                 330                 335

Ile Gly Phe Glu Thr Glu Asp Lys Lys Leu Ile Thr Ala Asp Phe Pro
            340                 345                 350

Gln Ile Glu Leu Arg Leu Ala Gly Val Ile Trp Asp Glu Pro Lys Phe
            355                 360                 365

Ile Glu Ala Phe Arg Gln Gly Ile Asp Leu His Lys Leu Thr Ala Ser
370                 375                 380

Ile Leu Phe Asp Lys Asn Ile Glu Glu Val Ser Lys Glu Glu Arg Gln
385                 390                 395                 400

Ile Gly Lys Ser Ala Asn Phe Gly Leu Ile Tyr Gly Ile Ser Pro Lys
                405                 410                 415

Gly Phe Ala Glu Tyr Cys Ile Ser Asn Gly Ile Asn Ile Thr Glu Glu
            420                 425                 430

Met Ala Ile Glu Ile Val Lys Lys Trp Lys Phe Tyr Arg Lys Ile
            435                 440                 445

Ala Glu Gln His Gln Leu Ala Tyr Glu Arg Phe Lys Tyr Ala Glu Phe
            450                 455                 460

Val Asp Asn Glu Thr Trp Leu Asn Arg Pro Tyr Arg Ala Tyr Lys Pro
465                 470                 475                 480

Gln Asp Leu Leu Asn Tyr Gln Ile Gln Gly Ser Gly Ala Glu Leu Phe
                485                 490                 495

Lys Lys Ala Ile Val Leu Leu Lys Glu Thr Lys Pro Asp Leu Lys Ile
            500                 505                 510

Val Asn Leu Val His Asp Glu Ile Val Val Glu Ala Asp Ser Lys Glu
            515                 520                 525

Ala Gln Asp Leu Ala Lys Leu Ile Lys Glu Lys Met Glu Glu Ala Trp
530                 535                 540

Asp Trp Cys Leu Glu Lys Ala Glu Glu Phe Gly Asn Arg Val Ala Lys
545                 550                 555                 560

Ile Lys Leu Glu Val Glu Glu Pro His Val Gly Asn Thr Trp Glu Lys
                565                 570                 575

Pro

<210> SEQ ID NO 13
<211> LENGTH: 2631
<212> TYPE: DNA
<213> ORGANISM: Artificial Sequence
<220> FEATURE:
<223> OTHER INFORMATION: M160-nuc DNA

<400> SEQUENCE: 13
atgcgtggta tgcttccact gtttgaaccg aaaggccgtg tgctgctggt tgatggccac         60

```
catctggcct atcgtacctt ccatgcgctg aaaggcctga cgaccagccg cggcgaaccg    120
gtgcaggcgg tgtatggctt tgcgaaaagc ctgctgaaag cgctgaaaga agatggcgat    180
gcggttattg tggtgtttga tgcgaaagcg ccgagctttc gtcatgaagc gtatggcggc    240
tataaagcgg tcgtgcgcc gaccccggaa gattttccgc gtcagctggc cctgattaaa     300
gaactggtgg atctgctggg cctggcgcgt ctggaagtgc cgggctatga agcggatgat    360
gtgctggcca gcctggccaa aaaagcggaa aaagaaggct acgaagttcg tattctgacc    420
gccgataaag acctgtatca gctgctgtct gatcgtattc atgtgctgca tcctgagggt    480
tatctgatta ccccggcgtg gctgtgggaa aaatatggcc tgcgtccgga tcagtgggcg    540
gattatcgtg cgctgaccgg cgatgaaagc gataacctgc cgggcgtgaa aggcattggc    600
gaaaaaaccg cgcgtaaact gctggaagaa tggggcagcc tggaagcgct gctgaaaaac    660
ctggatcgtc tgaaaccggc gattcgtgaa aagatcttag cgcacatgga tgatctgaaa    720
ctgagctggg atctggccaa agtgcgtacc gatctgccgc tggaagtgga ttttgcgaaa    780
cgtcgtgaac cggatcgtga acgtctgcgt gcgtttctgg aacgtctgga atttggcagc    840
ctgctgcatg aatttggcct gctggaaagc ggtggcggcg ttctggcgg tggtggcagc    900 aatacccga aaccgattct gaaaccgcag agcaaagcac tggttgaacc tgttctgtgt    960
gatagcattg atgaaattcc ggcaaaatac aatgaacctg tgtattttga tctggcaacc    1020
gatgaagatc gtccggttct ggcaagcatt tatcagccgc attttgaacg taaagtgtat    1080
tgtctgaatc tgctgcgtga aaaactggca cgttttaaag aatggctgct gaaatttagc    1140
gaaattcgtg gttggggctt agatttcgat ctgcgtgttc tgggttatac ctatgaacag    1200
ctgcgcaaca aaaaaatcgt tgacgtccag ctggccatta agtgcagca ttatgaacgc     1260 tttaaacaag gtggcaccaa aggtgaaggt tttcgtctgg atgatgttgc acgtgatctg    1320
ctgggtattg aatatccgat gaacaaaacg aaaatccgca ccaccttcaa gtataacatg    1380
tatagcagct tttcgtacga gcaactgctg tatgcaagcc tggatgcata tattccgcat    1440
ctgctgtacg aacgtctgag cagcgatacc ctgaatagcc tggtttatca gattgatcaa    1500
gaggttcaga agtggtgat tgaaaccagc cagcatggta tgccggttaa actgaaagca     1560
ctggaagaag aaattcatcg tctgacccag ctgcgtagcg aaatgcagaa acaaattccg    1620
tttaactata atagcccgaa acagaccgcc aaattctttg gtgttaatag cagcagcaaa    1680
gatgttctga tggatctggc actgcgtggt aatgaagttg ccaaaaaagt tctggaagca    1740
cgccagattg aaaaaagtct ggcattcgcc aaagatctgt atgatatcgc caaaaaaaac    1800
ggtggtcgca tctatggtaa cttttttacc accaccgcac cgagcggtcg tatgagctgt    1860
agcgatatta acctgcagca aattccgcgt cgtctgcgtc cgtttattgg ttttgaaacc    1920
gaggacaaaa aactgatcac cgcagatttt ccgcagattg aactgcgtct ggcaggcgtt    1980
atgtggaatg aacctgaatt tctgaaagcc tttcgtgatg cattgatct gcacaaactg     2040 accgcaagta ttctgttcga taaaaagatt aacgaagtga gcaaagagga acgccagatc    2100
ggtaaaagcg caaattttgg tctgattat ggtatcagcc cgaaaggttt tgccgaatat    2160
tgtattagca acggcattaa catcaccgaa gaaatggcaa tcgagatcgt gaaaaatgg    2220 aagaagttct atcgcaaaat cgccgaacag catcagctgg catatgaacg tttcaaatat    2280
gccgaattcg tggataatga aacctggctg atcgtccgt atcgtgcatg gaaaccgcaa    2340
gatctgctga actatcagat tcaaggtagc ggtgcagaac tgttcaaaaa agcaattgtt    2400
ctgctgaaag aagccaaacc ggatctgaaa attgtgaatc tggttcacga tgaaattgtg    2460
```

```
gtggaaaacca gtaccgaaga agcagaagat attgcactgc tggtgaaaca aaagatggaa    2520
gaggcatggg attattgcct ggaaaaagca aaagaatttg gcaataacgt ggccgacatt    2580
aaactggaag ttgaaaaacc gaatattagc agcgtgtggg aaaaagaata a              2631
```

<210> SEQ ID NO 14
<211> LENGTH: 876
<212> TYPE: PRT
<213> ORGANISM: Artificial Sequence
<220> FEATURE:
<223> OTHER INFORMATION: M160-nuc PRT

<400> SEQUENCE: 14

| | | | | | | | | | | | | | | | |
|---|---|---|---|---|---|---|---|---|---|---|---|---|---|---|---|
| Met | Arg | Gly | Met | Leu | Pro | Leu | Phe | Glu | Pro | Lys | Gly | Arg | Val | Leu | Leu |
| 1 | | | | 5 | | | | | 10 | | | | | 15 | |
| Val | Asp | Gly | His | His | Leu | Ala | Tyr | Arg | Thr | Phe | His | Ala | Leu | Lys | Gly |
| | | | 20 | | | | | 25 | | | | | 30 | | |
| Leu | Thr | Thr | Ser | Arg | Gly | Glu | Pro | Val | Gln | Ala | Val | Tyr | Gly | Phe | Ala |
| | | 35 | | | | | 40 | | | | | 45 | | | |
| Lys | Ser | Leu | Leu | Lys | Ala | Leu | Lys | Glu | Asp | Gly | Asp | Ala | Val | Ile | Val |
| | 50 | | | | | 55 | | | | | 60 | | | | |
| Val | Phe | Asp | Ala | Lys | Ala | Pro | Ser | Phe | Arg | His | Glu | Ala | Tyr | Gly | Gly |
| 65 | | | | | 70 | | | | | 75 | | | | | 80 |
| Tyr | Lys | Ala | Gly | Arg | Ala | Pro | Thr | Pro | Glu | Asp | Phe | Pro | Arg | Gln | Leu |
| | | | | 85 | | | | | 90 | | | | | 95 | |
| Ala | Leu | Ile | Lys | Glu | Leu | Val | Asp | Leu | Leu | Gly | Leu | Ala | Arg | Leu | Glu |
| | | | 100 | | | | | 105 | | | | | 110 | | |
| Val | Pro | Gly | Tyr | Glu | Ala | Asp | Asp | Val | Leu | Ala | Ser | Leu | Ala | Lys | Lys |
| | | 115 | | | | | 120 | | | | | 125 | | | |
| Ala | Glu | Lys | Glu | Gly | Tyr | Glu | Val | Arg | Ile | Leu | Thr | Ala | Asp | Lys | Asp |
| | 130 | | | | | 135 | | | | | 140 | | | | |
| Leu | Tyr | Gln | Leu | Leu | Ser | Asp | Arg | Ile | His | Val | Leu | His | Pro | Glu | Gly |
| 145 | | | | | 150 | | | | | 155 | | | | | 160 |
| Tyr | Leu | Ile | Thr | Pro | Ala | Trp | Leu | Trp | Glu | Lys | Tyr | Gly | Leu | Arg | Pro |
| | | | | 165 | | | | | 170 | | | | | 175 | |
| Asp | Gln | Trp | Ala | Asp | Tyr | Arg | Ala | Leu | Thr | Gly | Asp | Glu | Ser | Asp | Asn |
| | | | 180 | | | | | 185 | | | | | 190 | | |
| Leu | Pro | Gly | Val | Lys | Gly | Ile | Gly | Glu | Lys | Thr | Ala | Arg | Lys | Leu | Leu |
| | | 195 | | | | | 200 | | | | | 205 | | | |
| Glu | Glu | Trp | Gly | Ser | Leu | Glu | Ala | Leu | Leu | Lys | Asn | Leu | Asp | Arg | Leu |
| | 210 | | | | | 215 | | | | | 220 | | | | |
| Lys | Pro | Ala | Ile | Arg | Glu | Lys | Ile | Leu | Ala | His | Met | Asp | Asp | Leu | Lys |
| 225 | | | | | 230 | | | | | 235 | | | | | 240 |
| Leu | Ser | Trp | Asp | Leu | Ala | Lys | Val | Arg | Thr | Asp | Leu | Pro | Leu | Glu | Val |
| | | | | 245 | | | | | 250 | | | | | 255 | |
| Asp | Phe | Ala | Lys | Arg | Arg | Glu | Pro | Asp | Arg | Glu | Arg | Leu | Arg | Ala | Phe |
| | | | 260 | | | | | 265 | | | | | 270 | | |
| Leu | Glu | Arg | Leu | Glu | Phe | Gly | Ser | Leu | Leu | His | Glu | Phe | Gly | Leu | Leu |
| | | 275 | | | | | 280 | | | | | 285 | | | |
| Glu | Ser | Gly | Gly | Gly | Gly | Ser | Gly | Gly | Gly | Gly | Ser | Asn | Thr | Pro | Lys |
| | 290 | | | | | 295 | | | | | 300 | | | | |
| Pro | Ile | Leu | Lys | Pro | Gln | Ser | Lys | Ala | Leu | Val | Glu | Pro | Val | Leu | Cys |
| 305 | | | | | 310 | | | | | 315 | | | | | 320 |
| Asp | Ser | Ile | Asp | Glu | Ile | Pro | Ala | Lys | Tyr | Asn | Glu | Pro | Val | Tyr | Phe |
| | | | | 325 | | | | | 330 | | | | | 335 | |

```
Asp Leu Ala Thr Asp Glu Asp Arg Pro Val Leu Ala Ser Ile Tyr Gln
             340                 345                 350

Pro His Phe Glu Arg Lys Val Tyr Cys Leu Asn Leu Leu Arg Glu Lys
             355                 360                 365

Leu Ala Arg Phe Lys Glu Trp Leu Leu Lys Phe Ser Glu Ile Arg Gly
    370                 375                 380

Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
                405                 410                 415

His Tyr Glu Arg Phe Lys Gln Gly Gly Thr Lys Gly Glu Gly Phe Arg
        420                 425                 430

Leu Asp Asp Val Ala Arg Asp Leu Leu Gly Ile Glu Tyr Pro Met Asn
        435                 440                 445

Lys Thr Lys Ile Arg Thr Thr Phe Lys Tyr Asn Met Tyr Ser Ser Phe
    450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
                485                 490                 495

Gln Ile Asp Gln Glu Val Gln Lys Val Val Ile Glu Thr Ser Gln His
        500                 505                 510

Gly Met Pro Val Lys Leu Lys Ala Leu Glu Glu Ile His Arg Leu
        515                 520                 525

Thr Gln Leu Arg Ser Glu Met Gln Lys Gln Ile Pro Phe Asn Tyr Asn
    530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
        580                 585                 590

Leu Tyr Asp Ile Ala Lys Lys Asn Gly Gly Arg Ile Tyr Gly Asn Phe
    595                 600                 605

Phe Thr Thr Thr Ala Pro Ser Gly Arg Met Ser Cys Ser Asp Ile Asn
610                 615                 620

Leu Gln Gln Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
        660                 665                 670

Asp Gly Ile Asp Leu His Lys Leu Thr Ala Ser Ile Leu Phe Asp Lys
    675                 680                 685

Lys Ile Asn Glu Val Ser Lys Glu Glu Arg Gln Ile Gly Lys Ser Ala
    690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735

Val Lys Lys Trp Lys Lys Phe Tyr Arg Lys Ile Ala Glu Gln His Gln
        740                 745                 750
```

Leu Ala Tyr Glu Arg Phe Lys Tyr Ala Glu Phe Val Asp Asn Glu Thr
755                 760                 765

Trp Leu Asn Arg Pro Tyr Arg Ala Trp Lys Pro Gln Asp Leu Leu Asn
770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Ala Glu Asp Ile Ala
                820                 825                 830

Leu Leu Val Lys Gln Lys Met Glu Glu Ala Trp Asp Tyr Cys Leu Glu
                835                 840                 845

Lys Ala Lys Glu Phe Gly Asn Asn Val Ala Asp Ile Lys Leu Glu Val
                850                 855                 860

Glu Lys Pro Asn Ile Ser Ser Val Trp Glu Lys Glu
865                 870                 875

<210> SEQ ID NO 15
<211> LENGTH: 588
<212> TYPE: PRT
<213> ORGANISM: Artificial Sequence
<220> FEATURE:
<223> OTHER INFORMATION: Sequence of GenBank AFN99405.1

<400> SEQUENCE: 15

Met Gly Glu Asp Gly Leu Ser Leu Pro Lys Met Met Asn Thr Pro Lys
1               5                   10                  15

Pro Ile Leu Lys Pro Gln Pro Lys Ala Leu Val Glu Pro Val Leu Cys
                20                  25                  30

Asp Ser Ile Asp Glu Ile Pro Ala Lys Tyr Asn Glu Pro Val Tyr Phe
            35                  40                  45

Asp Leu Ala Thr Asp Glu Asp Arg Pro Val Leu Ala Ser Ile Tyr Gln
50                  55                  60

Pro His Phe Glu Arg Lys Val Tyr Cys Leu Asn Leu Leu Lys Glu Lys
65                  70                  75                  80

Val Ala Arg Phe Lys Asp Trp Leu Leu Lys Phe Ser Glu Ile Arg Gly
                85                  90                  95

Trp Gly Leu Asp Phe Asp Leu Arg Val Leu Gly Tyr Thr Tyr Glu Gln
                100                 105                 110

Leu Arg Asn Lys Lys Ile Val Asp Val Gln Leu Ala Ile Lys Val Gln
            115                 120                 125

His Tyr Glu Arg Phe Lys Gln Gly Gly Thr Lys Gly Glu Gly Phe Arg
130                 135                 140

Leu Asp Asp Val Ala Arg Asp Leu Leu Gly Ile Glu Tyr Pro Met Asn
145                 150                 155                 160

Lys Thr Lys Ile Arg Glu Thr Phe Lys Asn Asn Met Phe His Ser Phe
                165                 170                 175

Ser Asn Glu Gln Leu Leu Tyr Ala Ser Leu Asp Ala Tyr Ile Pro His
            180                 185                 190

Leu Leu Tyr Glu Gln Leu Thr Ser Ser Thr Leu Asn Ser Leu Val Tyr
        195                 200                 205

Gln Leu Asp Gln Gln Ala Gln Lys Val Val Ile Glu Thr Ser Gln His
210                 215                 220

Gly Met Pro Val Lys Leu Lys Ala Leu Glu Glu Glu Ile His Arg Leu
225                 230                 235                 240

```
Thr Gln Leu Arg Ser Glu Met Gln Lys Gln Ile Pro Phe Asn Tyr Asn
            245                 250                 255
Ser Pro Lys Gln Thr Ala Lys Phe Phe Gly Val Asn Ser Ser Ser Lys
        260                 265                 270
Asp Val Leu Met Asp Leu Ala Leu Gln Gly Asn Glu Met Ala Lys Lys
    275                 280                 285
Val Leu Glu Ala Arg Gln Ile Glu Lys Ser Leu Ala Phe Ala Lys Asp
290                 295                 300
Leu Tyr Asp Ile Ala Lys Arg Ser Gly Gly Arg Ile Tyr Gly Asn Phe
305                 310                 315                 320
Phe Thr Thr Thr Ala Pro Ser Gly Arg Met Ser Cys Ser Asp Ile Asn
                325                 330                 335
Leu Gln Gln Ile Pro Arg Arg Leu Arg Ser Phe Ile Gly Phe Asp Thr
            340                 345                 350
Glu Asp Lys Lys Leu Ile Thr Ala Asp Phe Pro Gln Ile Glu Leu Arg
        355                 360                 365
Leu Ala Gly Val Ile Trp Asn Glu Pro Lys Phe Ile Glu Ala Phe Arg
    370                 375                 380
Gln Gly Ile Asp Leu His Lys Leu Thr Ala Ser Ile Leu Phe Asp Lys
385                 390                 395                 400
Asn Ile Glu Glu Val Ser Lys Glu Arg Gln Ile Gly Lys Ser Ala
                405                 410                 415
Asn Phe Gly Leu Ile Tyr Gly Ile Ala Pro Lys Gly Phe Ala Glu Tyr
            420                 425                 430
Cys Ile Ala Asn Gly Ile Asn Met Thr Glu Glu Gln Ala Tyr Glu Ile
        435                 440                 445
Val Arg Lys Trp Lys Lys Tyr Tyr Thr Lys Ile Ala Glu Gln His Gln
    450                 455                 460
Val Ala Tyr Glu Arg Phe Lys Tyr Asn Glu Tyr Val Asp Asn Glu Thr
465                 470                 475                 480
Trp Leu Asn Arg Thr Tyr Arg Ala Trp Lys Pro Gln Asp Leu Leu Asn
                485                 490                 495
Tyr Gln Ile Gln Gly Ser Gly Ala Glu Leu Phe Lys Lys Ala Ile Val
            500                 505                 510
Leu Leu Lys Glu Thr Lys Pro Asp Leu Lys Ile Val Asn Leu Val His
        515                 520                 525
Asp Glu Ile Val Val Glu Ala Asp Ser Lys Glu Ala Gln Asp Leu Ala
    530                 535                 540
Lys Leu Ile Lys Glu Lys Met Glu Glu Ala Trp Asp Trp Cys Leu Glu
545                 550                 555                 560
Lys Ala Glu Glu Phe Gly Asn Arg Val Ala Lys Ile Lys Leu Glu Val
                565                 570                 575
Glu Glu Pro His Val Gly Asn Thr Trp Glu Lys Pro
            580                 585

<210> SEQ ID NO 16
<211> LENGTH: 30
<212> TYPE: PRT
<213> ORGANISM: Artificial Sequence
<220> FEATURE:
<223> OTHER INFORMATION: 231-260 region

<400> SEQUENCE: 16

Gln Leu Arg Ser Glu Met Gln Lys Gln Ile Pro Phe Asn Tyr Asn Ser
1               5                   10                  15
```

```
Pro Lys Gln Thr Ala Lys Phe Phe Gly Val Asn Ser Ser
            20                  25                  30
```

<210> SEQ ID NO 17
<211> LENGTH: 73
<212> TYPE: PRT
<213> ORGANISM: Artificial Sequence
<220> FEATURE:
<223> OTHER INFORMATION: 400-472 region

<400> SEQUENCE: 17

```
Gln Ile Gly Lys Ser Ala Asn Phe Gly Leu Ile Tyr Gly Ile Ser Pro
1               5                   10                  15
Lys Gly Phe Ala Glu Tyr Cys Ile Ser Asn Gly Ile Asn Ile Thr Glu
            20                  25                  30
Glu Met Ala Ile Glu Ile Val Lys Lys Trp Lys Lys Phe Tyr Arg Lys
        35                  40                  45
Ile Ala Glu Gln His Gln Leu Ala Tyr Glu Arg Phe Lys Tyr Ala Glu
    50                  55                  60
Phe Val Asp Asn Glu Thr Trp Leu Asn
65                  70
```

<210> SEQ ID NO 18
<211> LENGTH: 577
<212> TYPE: PRT
<213> ORGANISM: Artificial Sequence
<220> FEATURE:
<223> OTHER INFORMATION: Parent 1

<400> SEQUENCE: 18

```
Met Asn Thr Pro Lys Pro Ile Leu Lys Pro Gln Pro Lys Ala Leu Val
1               5                   10                  15
Glu Pro Val Leu Cys Asp Ser Ile Asp Glu Ile Pro Ala Lys Tyr Asn
            20                  25                  30
Glu Pro Val Tyr Phe Asp Leu Ala Thr Asp Glu Asp Arg Pro Val Leu
        35                  40                  45
Ala Ser Ile Tyr Gln Pro His Phe Glu Arg Lys Val Tyr Cys Leu Asn
    50                  55                  60
Leu Leu Lys Glu Lys Val Ala Arg Phe Lys Asp Trp Leu Leu Lys Phe
65                  70                  75                  80
Ser Glu Ile Arg Gly Trp Gly Leu Asp Phe Asp Leu Arg Val Leu Gly
                85                  90                  95
Tyr Thr Tyr Glu Gln Leu Arg Asn Lys Lys Ile Val Asp Val Gln Leu
            100                 105                 110
Ala Ile Lys Val Gln His Tyr Glu Arg Phe Lys Gln Gly Gly Thr Lys
        115                 120                 125
Gly Glu Gly Phe Arg Leu Asp Asp Val Ala Arg Asp Leu Leu Gly Ile
    130                 135                 140
Glu Tyr Pro Met Asn Lys Thr Lys Ile Arg Glu Thr Phe Lys Asn Asn
145                 150                 155                 160
Met Phe His Ser Phe Ser Asn Glu Gln Leu Leu Tyr Ala Ser Leu Asp
                165                 170                 175
Ala Tyr Ile Pro His Leu Leu Tyr Glu Gln Leu Thr Ser Ser Thr Leu
            180                 185                 190
Asn Ser Leu Val Tyr Gln Leu Asp Gln Gln Ala Gln Lys Val Val Ile
        195                 200                 205
Glu Thr Ser Gln His Gly Met Pro Val Lys Leu Lys Ala Leu Glu Glu
    210                 215                 220
```

```
Glu Ile His Arg Leu Thr Gln Leu Arg Ser Glu Met Gln Lys Gln Ile
225                 230                 235                 240

Pro Phe Asn Tyr Asn Ser Pro Lys Gln Thr Ala Lys Phe Phe Gly Val
            245                 250                 255

Asn Ser Ser Lys Asp Val Leu Met Asp Leu Ala Leu Gln Gly Asn
        260                 265                 270

Glu Met Ala Lys Lys Val Leu Glu Ala Arg Gln Ile Glu Lys Ser Leu
        275                 280                 285

Ala Phe Ala Lys Asp Leu Tyr Asp Ile Ala Lys Arg Ser Gly Gly Arg
290                 295                 300

Ile Tyr Gly Asn Phe Phe Thr Thr Thr Ala Pro Ser Gly Arg Met Ser
305                 310                 315                 320

Cys Ser Asp Ile Asn Leu Gln Gln Ile Pro Arg Arg Leu Arg Ser Phe
                325                 330                 335

Ile Gly Phe Asp Thr Glu Asp Lys Lys Leu Ile Thr Ala Asp Phe Pro
                340                 345                 350

Gln Ile Glu Leu Arg Leu Ala Gly Val Ile Trp Asn Glu Pro Lys Phe
                355                 360                 365

Ile Glu Ala Phe Arg Gln Gly Ile Asp Leu His Lys Leu Thr Ala Ser
        370                 375                 380

Ile Leu Phe Asp Lys Asn Ile Glu Val Ser Lys Glu Arg Gln
385                 390                 395                 400

Ile Gly Lys Ser Ala Asn Phe Gly Leu Ile Tyr Gly Ile Ala Pro Lys
                405                 410                 415

Gly Phe Ala Glu Tyr Cys Ile Ala Asn Gly Ile Asn Met Thr Glu Glu
                420                 425                 430

Gln Ala Tyr Glu Ile Val Arg Lys Trp Lys Lys Tyr Tyr Thr Lys Ile
            435                 440                 445

Ala Glu Gln His Gln Val Ala Tyr Glu Arg Phe Lys Tyr Asn Glu Tyr
        450                 455                 460

Val Asp Asn Glu Thr Trp Leu Asn Arg Thr Tyr Arg Ala Trp Lys Pro
465                 470                 475                 480

Gln Asp Leu Leu Asn Tyr Gln Ile Gln Gly Ser Gly Ala Glu Leu Phe
                485                 490                 495

Lys Lys Ala Ile Val Leu Leu Lys Glu Thr Lys Pro Asp Leu Lys Ile
                500                 505                 510

Val Asn Leu Val His Asp Glu Ile Val Val Glu Ala Asp Ser Lys Glu
            515                 520                 525

Ala Gln Asp Leu Ala Lys Leu Ile Lys Glu Lys Met Glu Glu Ala Trp
        530                 535                 540

Asp Trp Cys Leu Glu Lys Ala Glu Glu Phe Gly Asn Arg Val Ala Lys
545                 550                 555                 560

Ile Lys Leu Glu Val Glu Glu Pro His Val Gly Asn Thr Trp Glu Lys
                565                 570                 575

Pro

<210> SEQ ID NO 19
<211> LENGTH: 577
<212> TYPE: PRT
<213> ORGANISM: Artificial Sequence
<220> FEATURE:
<223> OTHER INFORMATION: Parent 2

<400> SEQUENCE: 19
```

-continued

```
Met Asn Thr Phe Ser Val Lys Thr Lys Ser Glu Pro Lys Ser Leu Val
1               5                   10                  15

Glu Pro Val Leu Cys Asn Ser Ile Asn Glu Ile Pro Ala Arg Phe Asp
            20                  25                  30

Glu Val Ile Tyr Phe Asp Leu Ala Thr Asp Glu Asn Arg Pro Thr Leu
            35                  40                  45

Ala Ser Leu Tyr Gln Pro Ser Phe Gly Arg Lys Val Tyr Cys Leu Asn
    50                  55                  60

Leu Leu Lys Glu Asn Pro Glu Arg Phe Lys Glu Trp Leu Leu Lys Phe
65                  70                  75                  80

Pro Glu Ile Arg Gly Trp Gly Leu Asp Phe Asp Leu Arg Val Leu Gly
                85                  90                  95

Phe Thr Tyr Glu Gln Leu Lys Asn Lys Lys Ile Val Asp Val Gln Leu
            100                 105                 110

Ala Ile Lys Val Gln Tyr Tyr Glu Arg Phe Lys Gln Asn Gly Ala Lys
        115                 120                 125

Gly Glu Gly Phe Arg Leu Asp Asp Val Ala Lys Asp Leu Leu Gly Ile
    130                 135                 140

Glu Tyr Pro Met Asn Lys Thr Lys Ile Arg Thr Thr Phe Lys Tyr Asn
145                 150                 155                 160

Met Tyr Ser Ser Phe Ser Tyr Glu Gln Leu Leu Tyr Ala Ser Leu Asp
                165                 170                 175

Ala Tyr Ile Pro His Leu Leu Tyr Glu Arg Leu Ser Ser Asp Thr Leu
            180                 185                 190

Asn Ser Leu Val Tyr Gln Ile Asp Gln Glu Val Gln Lys Val Val Ile
        195                 200                 205

Glu Thr Ser Gln His Gly Met Pro Val Lys Leu Gln Ala Leu Glu Glu
    210                 215                 220

Glu Ile His Arg Leu Ile Gln Leu Arg Asn Gln Met Gln Lys Glu Ile
225                 230                 235                 240

Pro Phe Asn Tyr Asn Ser Pro Lys Gln Thr Ala Lys Leu Phe Gly Ile
                245                 250                 255

Asp Ser Ser Ser Lys Asp Val Leu Met Asp Leu Ala Leu Arg Gly Asn
            260                 265                 270

Glu Val Ala Lys Lys Val Leu Glu Ala Arg Gln Ile Glu Lys Ser Leu
        275                 280                 285

Ala Phe Ala Lys Asp Leu Tyr Asp Ile Ala Lys Lys Asn Gly Gly Arg
    290                 295                 300

Ile Tyr Gly Asn Phe Phe Thr Thr Ala Pro Ser Gly Arg Met Ser
305                 310                 315                 320

Cys Ser Asp Ile Asn Leu Gln Gln Ile Pro Arg Arg Leu Arg Gln Phe
                325                 330                 335

Ile Gly Phe Glu Thr Glu Asp Lys Lys Leu Ile Thr Ala Asp Phe Pro
            340                 345                 350

Gln Ile Glu Leu Arg Leu Ala Gly Val Met Trp Asn Glu Pro Glu Phe
        355                 360                 365

Leu Lys Ala Phe Arg Asp Gly Ile Asp Leu His Lys Leu Thr Ala Ser
    370                 375                 380

Ile Leu Phe Asp Lys Lys Ile Asn Glu Val Ser Lys Glu Glu Arg Gln
385                 390                 395                 400

Ile Gly Lys Ser Ala Asn Phe Gly Leu Ile Tyr Gly Ile Ser Pro Lys
                405                 410                 415

Gly Phe Ala Glu Tyr Cys Ile Ser Asn Gly Ile Asn Ile Thr Glu Glu
```

```
                        420                 425                 430
Met Ala Ile Glu Ile Val Lys Lys Trp Lys Lys Phe Tyr Arg Lys Ile
                    435                 440                 445
Ala Glu Gln His Gln Leu Ala Tyr Glu Arg Phe Lys Tyr Ala Glu Phe
                450                 455                 460
Val Asp Asn Glu Thr Trp Leu Asn Arg Pro Tyr Arg Ala Tyr Lys Pro
465                 470                 475                 480
Gln Asp Leu Leu Asn Tyr Gln Ile Gln Gly Ser Gly Ala Glu Leu Phe
                485                 490                 495
Lys Lys Ala Ile Ile Leu Leu Lys Glu Thr Lys Pro Asp Leu Lys Leu
            500                 505                 510
Val Asn Leu Val His Asp Glu Ile Val Val Glu Thr Ser Thr Glu Glu
            515                 520                 525
Ala Glu Asp Ile Ala Leu Leu Val Lys Gln Lys Met Glu Glu Ala Trp
            530                 535                 540
Asp Tyr Cys Leu Glu Lys Ala Lys Glu Phe Gly Asn Asn Val Ala Asp
545                 550                 555                 560
Ile Lys Leu Glu Val Glu Lys Pro Asn Ile Ser Ser Val Trp Glu Lys
                565                 570                 575
Glu

<210> SEQ ID NO 20
<211> LENGTH: 576
<212> TYPE: PRT
<213> ORGANISM: Artificial Sequence
<220> FEATURE:
<223> OTHER INFORMATION: Parent 3

<400> SEQUENCE: 20

Met Asn Thr Pro Lys Pro Ile Leu Lys Pro Gln Ser Lys Ala Leu Val
1               5                   10                  15
Glu Pro Val Leu Cys Asn Ser Ile Asp Glu Ile Pro Ala Lys Tyr Asn
                20                  25                  30
Glu Pro Ile Tyr Phe Asp Leu Ala Thr Asp Glu Asp Arg Pro Val Leu
            35                  40                  45
Ala Ser Ile Tyr Gln Pro His Phe Glu Arg Lys Val Tyr Cys Leu Asn
50                  55                  60
Leu Leu Arg Glu Lys Leu Ala Arg Phe Lys Glu Trp Leu Leu Lys Phe
65                  70                  75                  80
Ser Glu Ile Arg Gly Trp Gly Leu Asp Phe Asp Leu Arg Val Leu Gly
                85                  90                  95
Tyr Thr Tyr Glu Gln Leu Arg Asn Lys Lys Ile Ile Asp Val Gln Leu
            100                 105                 110
Ala Leu Lys Val Gln His Tyr Glu Arg Phe Lys Gln Gly Gly Thr Lys
            115                 120                 125
Gly Glu Gly Phe Arg Leu Asp Asp Val Ala Arg Asp Leu Leu Gly Ile
        130                 135                 140
Glu Tyr Pro Met Asn Lys Thr Lys Ile Arg Glu Thr Phe Lys Asn Asn
145                 150                 155                 160
Met Phe His Ser Phe Ser Asn Glu Gln Leu Tyr Ala Ser Phe Asp
                165                 170                 175
Ala Tyr Ile Pro His Leu Leu Tyr Glu Gln Leu Thr Ser Ser Thr Leu
            180                 185                 190
Asn Ser Leu Val Tyr Gln Leu Asp Gln Gln Ala Gln Lys Ile Val Ile
            195                 200                 205
```

Glu Thr Ser Gln His Gly Met Pro Val Lys Leu Lys Ala Leu Glu Glu
              210                 215                 220
Glu Ile His Arg Leu Thr Gln Leu Arg Ser Glu Met Gln Arg Gln Ile
225                 230                 235                 240
Pro Phe Asn Tyr Asn Ser Pro Lys Gln Thr Ala Lys Phe Phe Gly Val
                245                 250                 255
Asp Ser Ser Ser Lys Asp Val Leu Met Asp Leu Ala Leu Gln Gly Asn
            260                 265                 270
Glu Met Ala Lys Lys Val Leu Glu Ala Arg Gln Ile Glu Lys Ser Leu
        275                 280                 285
Thr Phe Ala Lys Glu Leu Tyr Asp Leu Ala Lys Asn Gly Arg Ile
290                 295                 300
Tyr Gly Asn Phe Phe Thr Thr Thr Ala Pro Ser Gly Arg Met Ser Cys
305                 310                 315                 320
Ser Asp Ile Asn Leu Gln Gln Ile Pro Arg Arg Leu Arg Pro Phe Ile
                325                 330                 335
Gly Phe Glu Thr Glu Asp Lys Lys Leu Ile Thr Ala Asp Phe Pro Gln
            340                 345                 350
Ile Glu Leu Arg Leu Ala Gly Val Ile Trp Asp Glu Pro Lys Phe Ile
        355                 360                 365
Glu Ala Phe Arg Gln Gly Ile Asp Leu His Lys Leu Thr Ala Ser Ile
370                 375                 380
Leu Phe Asp Lys Asn Ile Glu Val Ser Lys Glu Arg Gln Ile
385                 390                 395                 400
Gly Lys Ser Ala Asn Phe Gly Leu Ile Tyr Gly Ile Ala Pro Lys Gly
                405                 410                 415
Phe Ala Glu Tyr Cys Ile Thr Asn Gly Ile Asn Met Thr Glu Glu Gln
            420                 425                 430
Ala Tyr Glu Ile Val Lys Lys Trp Lys Arg Tyr Tyr Thr Lys Ile Thr
        435                 440                 445
Glu Gln His Gln Val Ala Tyr Glu Arg Phe Lys Tyr Asn Glu Tyr Val
450                 455                 460
Asp Asn Glu Thr Trp Leu Ala Arg Thr Tyr Arg Ala Tyr Lys Pro Gln
465                 470                 475                 480
Asp Leu Leu Asn Tyr Gln Ile Gln Gly Ser Gly Ala Glu Leu Phe Lys
                485                 490                 495
Lys Ala Ile Val Leu Leu Lys Glu Ala Lys Pro Asp Leu Lys Ile Val
            500                 505                 510
Asn Leu Val His Asp Glu Ile Val Val Glu Ala Asp Ser Lys Glu Ala
        515                 520                 525
Gln Asp Leu Ala Lys Leu Ile Lys Glu Lys Met Glu Glu Ala Trp Asp
530                 535                 540
Trp Cys Leu Glu Lys Ala Glu Glu Phe Gly Asn Arg Val Ala Lys Ile
545                 550                 555                 560
Lys Leu Glu Val Glu Glu Pro Asn Val Gly Asn Thr Trp Glu Lys Pro
                565                 570                 575

<210> SEQ ID NO 21
<211> LENGTH: 29
<212> TYPE: PRT
<213> ORGANISM: Artificial Sequence
<220> FEATURE:
<223> OTHER INFORMATION: Amino terminus
<220> FEATURE:
<221> NAME/KEY: VARIANT

```
<222> LOCATION: 3
<223> OTHER INFORMATION: Xaa is Ala or Thr
<220> FEATURE:
<221> NAME/KEY: VARIANT
<222> LOCATION: 12
<223> OTHER INFORMATION: Xaa is Pro or Ser
<220> FEATURE:
<221> NAME/KEY: VARIANT
<222> LOCATION: 22
<223> OTHER INFORMATION: Xaa is Asn or Asp
<220> FEATURE:
<221> NAME/KEY: VARIANT
<222> LOCATION: 25
<223> OTHER INFORMATION: Xaa is Asn or Asp

<400> SEQUENCE: 21

Met Asn Xaa Pro Lys Pro Ile Leu Lys Pro Gln Xaa Lys Ala Leu Val
1               5                   10                  15

Glu Pro Val Leu Cys Xaa Ser Ile Xaa Glu Ile Pro Ala
            20                  25

<210> SEQ ID NO 22
<211> LENGTH: 10
<212> TYPE: PRT
<213> ORGANISM: Artificial Sequence
<220> FEATURE:
<223> OTHER INFORMATION: Linker

<400> SEQUENCE: 22

Gly Gly Gly Gly Ser Gly Gly Gly Gly Ser
1               5                   10

<210> SEQ ID NO 23
<211> LENGTH: 3569
<212> TYPE: DNA
<213> ORGANISM: Artificial Sequence
<220> FEATURE:
<223> OTHER INFORMATION: Sequence of GenBank V00642.1

<400> SEQUENCE: 23
gggtgggacc cctttcgggg tcctgctcaa cttcctgtcg agctaatgcc attttaatg       60 tctttagcga gacgctacca tggctatcgc tgtaggtagc cggaattcca ttcctaggag     120
gtttgacctg tgcgagcttt tagtacccct gatagggaga acgagacctt cgtcccctcc     180
gttcgcgttt acgcggacgg tgagactgaa gataactcat tctctttaaa atatcgttcg    240
aactggactc ccggtcgttt taactcgact ggggccaaaa cgaaacagtg cactacccc     300 tctccgtatt cacgggggc gttaagtgtc acatcgatag atcaaggtgc ctacaagcga     360
agtgggtcat cgtggggtcg cccgtacgag gagaaagccg gtttcggctt ctccctcgac    420
gcacgctcct gctacagcct cttccctgta agccaaaact tgacttacat cgaagtgccg    480
cagaacgttg cgaaccgggc gtcgaccgaa gtcctgcaaa aggtcaccca gggtaatttt    540
aaccttggtg ttgctttagc agaggccagg tcgacagcct cacaactcgc gacgcaaacc    600
attgcgctcg tgaaggcgta cactgccgct cgtcgcggta ttggcgcca ggcgctccgc     660 taccttgccc taaacgaaga tcgaaagttt cgatcaaaac acgtggccgg caggtggttg    720
gagttgcagt tcggttggtt accactaatg agtgatatcc agggtgcata tgagatgctt    780
acgaaggttc accttcaaga gtttcttcct atgagagccg tacgtcaggt cggtactaac    840
atcaagttag atggccgtct gtcgtatcca gctgcaaact tccagacaac gtgcaacata    900
tcgcgacgta tcgtgatatg gttttacata aacgatgcac gtttggcatg ttgtcgtctt    960
ctaggtatct tgaacccact aggtatagtg tgggaaaagg tgcctttctc attcgttgtc   1020
```

```
gactggctcc tacctgtagg taacatgctc gagggcctta cggccccccgt gggatgctcc    1080 tacatgtcag gaacagttac tgacgtaata acgggtgagt ccatcataag cgttgacgct    1140
ccctacgggt ggactgtgga gagacagggc actgctaagg cccaaatctc agccatgcat    1200
cgaggggtac aatccgtatg gccaacaact ggcgcgtacg taaagtctcc tttctcgatg    1260
gtccatacct tagatgcgtt agcattaatc aggcaacggc tctctagata gagccctcaa    1320
ccggagtttg aagcatggct tctaacttta ctcagttcgt tctcgtcgac aatggcggaa    1380
ctggcgacgt gactgtcgcc ccaagcaact tcgctaacgg ggtcgctgaa tggatcagct    1440
ctaactcgcg ttcacaggct tacaaagtaa cctgtagcgt tcgtcagagc tctgcgcaga    1500
atcgcaaata caccatcaaa gtcgaggtgc ctaaagtggc aacccagact gttggtggtg    1560
tagagcttcc tgtagccgca tggcgttcgt acttaaatat ggaactaacc attccaattt    1620
tcgctacgaa ttccgactgc gagcttattg ttaaggcaat gcaaggtctc ctaaaagatg    1680
gaaacccgat tccctcagca atcgcagcaa actccggcat ctactaatag acgccggcca    1740
ttcaaacatg aggattaccc atgtcgaaga caacaaagaa gttcaactct ttatgtattg    1800
atcttcctcg cgatctttct ctcgaaattt accaatcaat tgcttctgtc gctactggaa    1860
gcggtgatcc gcacagtgac gactttacag caattgctta cttaagggac gaattgctca    1920
caaagcatcc gaccttaggt tctggtaatg acgaggcgac ccgtcgtacc ttagctatcg    1980
ctaagctacg ggaggcgaat ggtgatcgcg gtcagataaa tagagaaggt ttcttacatg    2040
acaaatcctt gtcatgggat ccggatgttt tacaaaccag catccgtagc cttattggca    2100
acctcctctc tggctaccga tcgtcgttgt ttgggcaatg cacgttctcc aacggtgctc    2160
ctatggggca caagttgcag gatgcagcgc cttacaagaa gttcgctgaa caagcaaccg    2220 ttacccccccg cgctctgaga gcggctctat tggtccgaga ccaatgtgcg ccgtggatca    2280
gacacgcggt ccgctataac gagtcatatg aatttaggct cgttgtaggg aacggagtgt    2340
ttacagttcc gaagaataat aaaatagatc gggctgcctg taaggagcct gatatgaata    2400
tgtacctcca gaaagggggtc ggtgctttca tcagacgccg gctcaaatcc gttggtatag    2460
acctgaatga tcaatcgatc aaccagcgtc tggctcagca gggcagcgta gatggttcgc    2520
ttgcgacgat agacttatcg tctgcatccg attccatctc cgatcgcctg gtgtggagtt    2580
ttctcccacc agagctatat tcatatctcg atcgtatccg ctcacactac ggaatcgtag    2640
atggcgagac gatacgatgg gaactatttt ccacaatggg aaatgggttc acatttgagc    2700
tagagtccat gatattctgg gcaatagtca aagcgaccca aatccatttt ggtaacgccg    2760
gaaccatagg catctacggg gacgatatta tatgtcccag tgagattgca ccccgtgtgc    2820
tagaggcact tgcctactac ggttttaaac cgaatcttcg taaaacgttc gtgtccgggc    2880
tctttcgcga gagctgcggc gcgcactttt accgtggtgt cgatgtcaaa ccgttttaca    2940
tcaagaaacc tgttgacaat ctcttcgccc tgatgctgat attaaatcgg ctacggggtt    3000
ggggagttgt cggaggtatg tcagatccac gcctctataa ggtgtgggta cggctctcct    3060
cccaggtgcc ttcgatgttc ttcggtggga cggacctcgc tgccgactac tacgtagtca    3120
gcccgcctac ggcagtctcg gtatacacca agactccgta cgggcggctg ctcgcggata    3180
cccgtacctc gggtttccgt cttgctcgta tcgctcgaga acgcaagttc ttcagcgaaa    3240
agcacgacag tggtcgctac atagcgtggt tccatactgg aggtgaaatc accgacagca    3300
tgaagtccgc cggcgtgcgc gttatacgca cttcggagtg gctaacgccg gttcccacat    3360
```

```
tccctcagga gtgtgggcca gcgagctctc ctcggtagct gaccgaggga ccccgtaaa   3420 cggggtgggt gtgctcgaaa gagcacgggt gcgaaagcgg tccggctcca ccgaaaggtg   3480
ggcgggcttc ggcccaggga cctccccta aagagaggac ccgggattct cccgatttgg    3540
taactagctg cttggctagt taccaccca                                     3569
```

<210> SEQ ID NO 24
<211> LENGTH: 2226
<212> TYPE: DNA
<213> ORGANISM: Homo sapiens
<220> FEATURE:
<223> OTHER INFORMATION: Sequence of GenBank NM_005566.3

<400> SEQUENCE: 24

```
gtctgccggt cggttgtctg gctgcgcgcg ccacccgggc ctctccagtg ccccgcctgg    60
ctcggcatcc accccagcc cgactcacac gtgggttccc gcacgtccgc cggcccccc    120 cgctgacgtc agcatagctg ttccacttaa ggcccctccc gcgcccagct cagagtgctg   180
cagccgctgc cgccgattcc ggatctcatt gccacgcgcc cccgacgacc gcccgacgtg   240
cattcccgat tccttttggt tccaagtcca atatggcaac tctaaaggat cagctgattt   300
ataatcttct aaaggaagaa cagaccccc agaataagat tacagttgtt ggggttggtg   360
ctgttggcat ggcctgtgcc atcagtatct taatgaagga cttggcagat gaacttgctc   420
ttgttgatgt catcgaagac aaattgaagg agagatgat ggatcccaa catggcagcc   480 ttttccttag aacaccaaag attgtctctg gcaaagacta taatgtaact gcaaactcca   540
agctggtcat tatcacggct ggggcacgtc agcaagaggg agaaagccgt cttaatttgg   600
tccagcgtaa cgtgaacatc tttaaattca tcattcctaa tgttgtaaaa tacagcccga   660
actgcaagtt gcttattgtt tcaaatccag tggatatctt gacctacgtg gcttggaaga   720
taagtggttt tcccaaaaac cgtgttattg gaagcggttg caatctggat tcagcccgat   780
tccgttacct aatgggggaa aggctgggag ttcacccatt aagctgtcat gggtgggtcc   840
ttggggaaca tggagattcc agtgtgcctg tatggagtgg aatgaatgtt gctggtgtct   900
ctctgaagac tctgcaccca gatttaggga ctgataaaga taaggaacag tggaaagagg   960
ttcacaagca ggtggttgag agtgcttatg aggtgatcaa actcaaaggc tacacatcct  1020
gggctattgg actctctgta gcagatttgg cagagagtat aatgaagaat cttaggcggg  1080
tgcacccagt ttccaccatg attaagggtc tttacggaat aaaggatgat gtcttcctta  1140
gtgttccttg cattttggga cagaatggaa tctcagacct tgtgaaggtg actctgactt  1200
ctgaggaaga ggcccgtttg aagaagagtg cagatacact ttgggggatc caaaaggagc  1260
tgcaatttta aagtcttctg atgtcatatc atttcactgt ctaggctaca acaggattct  1320
aggtggaggt tgtgcatgtt gtccttttta tctgatctgt gattaaagca gtaatatttt  1380
aagatggact gggaaaaaca tcaactcctg aagttagaaa taagaatggt ttgtaaaatc  1440
cacagctata tcctgatgct ggatggtatt aatcttgtgt agtcttcaac tggttagtgt  1500
gaaatagttc tgccacctct gacgcaccac tgccaatgct gtacgtactg catttgcccc  1560
ttgagccagg tggatgttta ccgtgtgtta tataacttcc tggctccttc actgaacatg  1620
cctagtccaa cattttttcc cagtgagtca catcctggga tccagtgtat aaatccaata  1680
tcatgtcttg tgcataattc ttccaaagga tcttatttg tgaactatat cagtagtgta  1740
cattaccata taatgtaaaa agatctacat acaaacaatg caaccaacta tccaagtgtt  1800
ataccaacta aaaccccaa taaaccttga acagtgacta ctttggttaa ttcattatat   1860
```

```
taagatataa agtcataaag ctgctagtta ttatattaat ttggaaatat taggctattc   1920
ttgggcaacc ctgcaacgat tttttctaac agggatatta ttgactaata gcagaggatg   1980
taatagtcaa ctgagttgta ttggtaccac ttccattgta agtcccaaag tattatatat   2040
ttgataataa tgctaatcat aattggaaag taacattcta tatgtaaatg taaaatttat   2100
ttgccaactg aatataggca atgatagtgt gtcactatag ggaacacaga tttttgagat   2160
cttgtcctct ggaagctggt aacaattaaa acaatctta aggcagggaa aaaaaaaaa    2220 aaaaaa                                                              2226
```

<210> SEQ ID NO 25
<211> LENGTH: 1471
<212> TYPE: DNA
<213> ORGANISM: Vibrio natriegens
<220> FEATURE:
<223> OTHER INFORMATION: Sequence of GenBank NR_117890.1

<400> SEQUENCE: 25

```
attgaacgct ggcggcaggc ctaacacatg caagtcgagc ggaaacgagt taactgaacc     60
ttcgggggac gttaacggcg tcgagcggcg gacgggtgag taatgcctag gaaattgccc    120
tgatgtgggg gataaccatt ggaaacgatg gctaataccg catgatgcct acgggccaaa    180
gagggggacc ttcgggcctc tcgcgtcagg atatgcctag gtgggattag ctagttggtg    240
aggtaagggc tcaccaaggc gacgatccct agctggtctg agaggatgat cagccacact    300
ggaactgaga cacggtccag actcctacgg gaggcagcag tggggaatat tgcacaatgg    360
gcgcaagcct gatgcagcca tgccgcgtgt gtgaagaagg ccttcgggtt gtaaagcact    420
ttcagtcgtg aggaaggtag tgtagttaat agctgcatta tttgacgtta gcgacagaag    480
aagcaccggc taactccgtg ccagcagccg cggtaatacg gagggtgcga gcgttaatcg    540
gaattactgg gcgtaaagcg catgcaggtg gtttgttaag tcagatgtga aagcccgggg    600
ctcaacctcg gaatagcatt tgaaactggc agactagagt actgtagagg ggggtagaat    660
ttcaggtgta gcggtgaaat gcgtagagat ctgaaggaat accggtggcg aaggcggccc    720
cctggacaga tactgacact cagatgcgaa agcgtgggga gcaaacagga ttagataccc    780
tggtagtcca cgccgtaaac gatgtctact tggaggttgt ggccttgagc cgtggctttc    840
ggagctaacg cgttaagtag accgcctggg gagtacggtc gcaagattaa aactcaaatg    900
aattgacggg ggcccgcaca agcggtggag catgtggttt aattcgatgc aacgcgaaga    960
accttaccta ctcttgacat ccagagaact ttccagagat ggattggtgc cttcgggaac   1020
tctgagacag gtgctgcatg gctgtcgtca gctcgtgttg tgaaatgttg ggttaagtcc   1080
cgcaacgagc gcaaccctta tccttgtttg ccagcgagta atgtcgggaa ctccaggag    1140 actgccggtg ataaccgga ggaaggtggg gacgacgtca agtcatcatg gcccttacga    1200
gtagggctac acacgtgcta caatggcgca tacagagggc ggccaacttg cgaaagtgag    1260
cgaatcccaa aaagtgcgtc gtagtccgga ttggagtctg caactcgact ccatgaagtc    1320
ggaatcgcta gtaatcgtgg atcagaatgc cacggtgaat acgttcccgg gccttgtaca    1380
caccgcccgt cacaccatgg gagtgggctg caaaagaagt aggtagttta accttcgggg   1440
ggacgcttac cactttgtgg ttcatgactg g                                  1471
```

<210> SEQ ID NO 26
<211> LENGTH: 73
<212> TYPE: PRT

<213> ORGANISM: Artificial Sequence
<220> FEATURE:
<223> OTHER INFORMATION: Parent 1 of Figure 2A

<400> SEQUENCE: 26

Gln Ile Gly Lys Ser Ala Asn Phe Gly Leu Ile Tyr Gly Ile Ala Pro
1               5                   10                  15

Lys Gly Phe Ala Glu Tyr Cys Ile Ala Asn Gly Ile Asn Met Thr Glu
            20                  25                  30

Glu Gln Ala Tyr Glu Ile Val Arg Lys Trp Lys Lys Tyr Tyr Thr Lys
        35                  40                  45

Ile Ala Glu Gln His Gln Val Ala Tyr Glu Arg Phe Lys Tyr Asn Glu
    50                  55                  60

Tyr Val Asp Asn Glu Thr Trp Leu Asn
65                  70

<210> SEQ ID NO 27
<211> LENGTH: 73
<212> TYPE: PRT
<213> ORGANISM: Artificial Sequence
<220> FEATURE:
<223> OTHER INFORMATION: Parent 2 of Figure 2A

<400> SEQUENCE: 27

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Lys Trp Lys Lys Phe Tyr Arg Lys
        35                  40                  45

Ile Ala Glu Gln His Gln Leu Ala Tyr Glu Arg Phe Lys Tyr Ala Glu
    50                  55                  60

Phe Val Asp Asn Glu Thr Trp Leu Asn
65                  70

<210> SEQ ID NO 28
<211> LENGTH: 73
<212> TYPE: PRT
<213> ORGANISM: Artificial Sequence
<220> FEATURE:
<223> OTHER INFORMATION: Parent 3 of Figure 2A

<400> SEQUENCE: 28

Gln Ile Gly Lys Ser Ala Asn Phe Gly Leu Ile Tyr Gly Ile Ala Pro
1               5                   10                  15

Lys Gly Phe Ala Glu Tyr Cys Ile Thr Asn Gly Ile Asn Met Thr Glu
            20                  25                  30

Glu Gln Ala Tyr Glu Ile Val Lys Lys Trp Lys Arg Tyr Tyr Thr Lys
        35                  40                  45

Ile Thr Glu Gln His Gln Val Ala Tyr Glu Arg Phe Lys Tyr Asn Glu
    50                  55                  60

Tyr Val Asp Asn Glu Thr Trp Leu Ala
65                  70

<210> SEQ ID NO 29
<211> LENGTH: 73
<212> TYPE: PRT
<213> ORGANISM: Artificial Sequence
<220> FEATURE:
<223> OTHER INFORMATION: M180_PRT of Figure 2A

<400> SEQUENCE: 29

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Trp Lys Lys Phe Tyr Arg Lys
        35                  40                  45

Ile Ala Glu Gln His Gln Leu Ala Tyr Glu Arg Phe Lys Tyr Ala Glu
    50                  55                  60

Phe Val Asp Asn Glu Thr Trp Leu Asn
65                  70

<210> SEQ ID NO 30
<211> LENGTH: 73
<212> TYPE: PRT
<213> ORGANISM: Artificial Sequence
<220> FEATURE:
<223> OTHER INFORMATION: M384_PRT of Figure 2A

<400> SEQUENCE: 30

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Trp Lys Lys Phe Tyr Arg Lys
        35                  40                  45

Ile Ala Glu Gln His Gln Leu Ala Tyr Glu Arg Phe Lys Tyr Ala Glu
    50                  55                  60

Phe Val Asp Asn Glu Thr Trp Leu Asn
65                  70

<210> SEQ ID NO 31
<211> LENGTH: 73
<212> TYPE: PRT
<213> ORGANISM: Artificial Sequence
<220> FEATURE:
<223> OTHER INFORMATION: M392_PRT of Figure 2A

<400> SEQUENCE: 31

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Trp Lys Lys Phe Tyr Arg Lys
        35                  40                  45

Ile Ala Glu Gln His Gln Leu Ala Tyr Glu Arg Phe Lys Tyr Ala Glu
    50                  55                  60

Phe Val Asp Asn Glu Thr Trp Leu Asn
65                  70

<210> SEQ ID NO 32
<211> LENGTH: 73
<212> TYPE: PRT
<213> ORGANISM: Artificial Sequence
<220> FEATURE:
<223> OTHER INFORMATION: M295_PRT of Figure 2A

<400> SEQUENCE: 32

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Trp Lys Lys Phe Tyr Arg Lys
        35                  40                  45

Ile Ala Glu Gln His Gln Leu Ala Tyr Glu Arg Phe Lys Tyr Ala Glu
    50                  55                  60

Phe Val Asp Asn Glu Thr Trp Leu Asn
65                  70

<210> SEQ ID NO 33
<211> LENGTH: 73
<212> TYPE: PRT
<213> ORGANISM: Artificial Sequence
<220> FEATURE:
<223> OTHER INFORMATION: M66_PRT of Figure 2A

<400> SEQUENCE: 33

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Trp Lys Lys Phe Tyr Arg Lys
        35                  40                  45

Ile Ala Glu Gln His Gln Leu Ala Tyr Glu Arg Phe Lys Tyr Ala Glu
    50                  55                  60

Phe Val Asp Asn Glu Thr Trp Leu Asn
65                  70

<210> SEQ ID NO 34
<211> LENGTH: 73
<212> TYPE: PRT
<213> ORGANISM: Artificial Sequence
<220> FEATURE:
<223> OTHER INFORMATION: M160_PRT of Figure 2A

<400> SEQUENCE: 34

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Trp Lys Lys Phe Tyr Arg Lys
        35                  40                  45

Ile Ala Glu Gln His Gln Leu Ala Tyr Glu Arg Phe Lys Tyr Ala Glu
    50                  55                  60

Phe Val Asp Asn Glu Thr Trp Leu Asn
65                  70

<210> SEQ ID NO 35
<211> LENGTH: 30
<212> TYPE: PRT
<213> ORGANISM: Artificial Sequence
<220> FEATURE:
<223> OTHER INFORMATION: Parent 1 of Figure 2B

<400> SEQUENCE: 35

Gln Leu Arg Ser Glu Met Gln Lys Gln Ile Pro Phe Asn Tyr Asn Ser
1               5                   10                  15

Pro Lys Gln Thr Ala Lys Phe Phe Gly Val Asn Ser Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Parent 2 of Figure 2B

<400> SEQUENCE: 36

Gln Leu Arg Asn Gln Met Gln Lys Glu Ile Pro Phe Asn Tyr Asn Ser
1               5                   10                  15

Pro Lys Gln Thr Ala Lys Leu Phe Gly Ile Asp Ser Ser Ser
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Parent 3 of Figure 2B

<400> SEQUENCE: 37

Gln Leu Arg Ser Glu Met Gln Arg Gln Ile Pro Phe Asn Tyr Asn Ser
1               5                   10                  15

Pro Lys Gln Thr Ala Lys Phe Phe Gly Val Asp Ser Ser Ser
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: M180_PRT of Figure 2B

<400> SEQUENCE: 38

Gln Leu Arg Ser Glu Met Gln Arg Gln Ile Pro Phe Asn Tyr Asn Ser
1               5                   10                  15

Pro Lys Gln Thr Ala Lys Phe Phe Gly Val Asp Ser Ser Ser
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: M384_PRT of Figure 2B

<400> SEQUENCE: 39

Gln Leu Arg Ser Glu Met Gln Lys Gln Ile Pro Phe Asn Tyr Asn Ser
1               5                   10                  15

Pro Lys Gln Thr Ala Lys Phe Phe Gly Val Asn Ser Ser Ser
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: M392_PRT of Figure 2B

<400> SEQUENCE: 40

Gln Leu Arg Ser Glu Met Gln Arg Gln Ile Pro Phe Asn Tyr Asn Ser
1               5                   10                  15

Pro Lys Gln Thr Ala Lys Phe Phe Gly Val Asp Ser Ser Ser
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: M295_PRT of Figure 2B

<400> SEQUENCE: 41

Gln Leu Arg Ser Glu Met Gln Arg Gln Ile Pro Phe Asn Tyr Asn Ser
1               5                   10                  15

Pro Lys Gln Thr Ala Lys Phe Phe Gly Val Asp Ser Ser Ser
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: M66_PRT of Figure 2B

<400> SEQUENCE: 42

Gln Leu Arg Ser Glu Met Gln Lys Gln Ile Pro Phe Asn Tyr Asn Ser
1               5                   10                  15

Pro Lys Gln Thr Ala Lys Phe Phe Gly Val Asn Ser Ser Ser
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: M160_PRT of Figure 2B

<400> SEQUENCE: 43

Gln Leu Arg Ser Glu Met Gln Lys Gln Ile Pro Phe Asn Tyr Asn Ser
1               5                   10                  15

Pro Lys Gln Thr Ala Lys Phe Phe Gly Val Asn Ser Ser Ser
            20                  25                  30

<210> SEQ ID NO 44
<211> LENGTH: 2628
<212> TYPE: DNA
<213> ORGANISM: Artificial Sequence
<220> FEATURE:
<223> OTHER INFORMATION: M401 DNA

<400> SEQUENCE: 44
atgcgtggta tgcttccact gtttgaaccg aaaggccgtg tgctgctggt tgatggccac      60
catctggcct atcgtacctt ccatgcgctg aaaggcctga cgaccagccg cggcgaaccg     120
gtgcaggcgg tgtatggctt tgcgaaaagc ctgctgaaag cgctgaaaga gatggcgat      180 gcggttattg tggtgtttga tgcgaaagcg ccgagctttc gtcatgaagc gtatggcggc     240
tataaagcgg tcgtgcgcc gaccccggaa gatttccgc gtcagctggc cctgattaaa      300
gaactggtgg atctgctggg cctggcgcgt ctggaagtgc gggctatga agcggatgat     360 gtgctggcca gcctggccaa aaaagcggaa aagaaggct acgaagttcg tattctgacc     420
gccgataaag acctgtatca gctgctgtct gatcgtattc atgtgctgca tcctgagggt     480
tatctgatta ccccggcgtg gctgtgggaa aaatatggcc tgcgtccgga tcagtgggcg     540
gattatcgtg cgctgaccgg cgatgaaagc gataacctgc cgggcgtgaa aggcattggc     600

```
gaaaaaaccg cgcgtaaact gctggaagaa tggggcagcc tggaagcgct gctgaaaaac    660
ctggatcgtc tgaaaccggc gattcgtgaa aagatcttag cgcacatgga tgatctgaaa    720
ctgagctggg atctggccaa agtgcgtacc gatctgccgc tggaagtgga ttttgcgaaa    780
cgtcgtgaac cggatcgtga acgtctgcgt gcgtttctgg aacgtctgga atttggcagc    840
ctgctgcatg aatttggcct gctggaaagc ggtggcggcg ttctggcgg tggtggcagc    900
aataccccga aaccgattct gaaaccgcag agcaaagcac tggttgaacc tgttctgtgt    960
gatagcattg atgaaattcc ggcaaaatac aatgaacctg tgtattttga tctggaaacc   1020
gatgaagatc gtccggttct ggcaagcatt tatcagccgc atttgaacg taaagtgtat   1080
tgtctgaatc tgctgcgtga aaaactggca cgttttaaag aatggctgct gaaattagc   1140
gaaattcgtg gttgggcctt agatttcgat ctgcgtgttc tgggttatac ctatgaacag   1200
ctgcgcaaca aaaaaatcgt tgacgtccag ctggccatta aagtgcagca ttatgaacgc   1260
tttaaacaag gtggcaccaa aggtgaaggt tttcgtctgg atgatgttgc acgtgatctg   1320
ctgggtattg aatatccgat gaacaaaacg aaaatccgca ccaccttcaa gtataacatg   1380
tatagcagct tttcgtacga gcaactgctg tatgcaagcc tggatgcata tattccgcat   1440
ctgctgtacaa acgtctgag cagcgatacc ctgaatagcc tggtttatca gattgatcaa   1500
gaggttcaga aagtggtgat tgaaaccagc cagcatggta tgccggttaa actgaaagca   1560
ctggaagaag aaattcatcg tctgacccag ctgcgtagca aatgcagaa acaaattccg   1620
tttaactata taagcccgaa acagaccgcc aaattctttg gtgttaatag cagcagcaaa   1680
gatgttctga tggatctggc actgcgtggt aatgaagttg ccaaaaaagt tctggaagca   1740
cgccagattg aaaaaagtct ggcattcgcc aaagatctgt atgatatcgc caaaaaaaac   1800
ggtggtcgca tctatggtaa cttttttttacc accaccgcac cgagcggtcg tatgagctgt   1860
agcgatatta acctgcagca aattccgcgt cgtctgcgtc cgtttattgg ttttgaaacc   1920
gaggacaaaa aactgatcac cgcagatttt ccgcagattg aactgcgtct ggcaggcgtt   1980
atgtggaatg aacctgaatt tctgaaagcc tttcgtgatg cattgatct gcacaaactg   2040
accgcaagta ttctgttcga taaaagatt aacgaagtga gcaaagagga acgccagatc   2100
ggtaaaagcg caaatttggg tctgatttat ggtatcagcc cgaaaggttt tgccgaatat   2160
tgtattagca acggcattaa catcaccgaa gaaatggcaa tcgagatcgt gaaaaaatgg   2220
aagaagttct atcgcaaaat cgccgaacag catcagctgg catatgaacg tttcaaatat   2280
gccgaattcg tggataatga aacctggctg atcgtccgt atcgtgcatg gaaaccgcaa   2340
gatctgctga actatcagat tcaaggtagc ggtgcagaac tgttcaaaa agcaattgtt   2400
ctgctgaaag aagccaaacc ggatctgaaa attgtgaatc tggttcacga tgaaattgtg   2460
gtggaaacca gtaccgaaga agcagaagat attgcactgc tggtgaaaca aaagatggaa   2520
gaggcatggg attattgcct ggaaaaagca aagaatttg caataacgt ggccgacatt   2580
aaactggaag ttgaaaaacc gaatatagc agcgtgtggg aaaagaa               2628
```

<210> SEQ ID NO 45
<211> LENGTH: 876
<212> TYPE: PRT
<213> ORGANISM: Artificial Sequence
<220> FEATURE:
<223> OTHER INFORMATION: M401 PRT

<400> SEQUENCE: 45

Met Arg Gly Met Leu Pro Leu Phe Glu Pro Lys Gly Arg Val Leu Leu

-continued

```
1               5                   10                  15
Val Asp Gly His His Leu Ala Tyr Arg Thr Phe His Ala Leu Lys Gly
                20                  25                  30
Leu Thr Thr Ser Arg Gly Glu Pro Val Gln Ala Val Tyr Gly Phe Ala
                35                  40                  45
Lys Ser Leu Leu Lys Ala Leu Lys Glu Asp Gly Asp Ala Val Ile Val
        50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
                100                 105                 110
Val Pro Gly Tyr Glu Ala Asp Asp Val Leu Ala Ser Leu Ala Lys Lys
                115                 120                 125
Ala Glu Lys Glu Gly Tyr Glu Val Arg Ile Leu Thr Ala Asp Lys Asp
        130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
        210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
                275                 280                 285
Glu Ser Gly Gly Gly Ser Gly Gly Gly Ser Asn Thr Pro Lys
        290                 295                 300
Pro Ile Leu Lys Pro Gln Ser Lys Ala Leu Val Glu Pro Val Leu Cys
305                 310                 315                 320
Asp Ser Ile Asp Glu Ile Pro Ala Lys Tyr Asn Glu Pro Val Tyr Phe
                325                 330                 335
Asp Leu Glu Thr Asp Glu Asp Arg Pro Val Leu Ala Ser Ile Tyr Gln
                340                 345                 350
Pro His Phe Glu Arg Lys Val Tyr Cys Leu Asn Leu Arg Glu Lys
                355                 360                 365
Leu Ala Arg Phe Lys Glu Trp Leu Leu Lys Phe Ser Glu Ile Arg Gly
        370                 375                 380
Trp Gly Leu Asp Phe Asp Leu Arg Val Leu Gly Tyr Thr Tyr Glu Gln
385                 390                 395                 400
Leu Arg Asn Lys Lys Ile Val Asp Val Gln Leu Ala Ile Lys Val Gln
                405                 410                 415
His Tyr Glu Arg Phe Lys Gln Gly Gly Thr Lys Gly Glu Gly Phe Arg
                420                 425                 430
```

```
Leu Asp Asp Val Ala Arg Asp Leu Leu Gly Ile Glu Tyr Pro Met Asn
        435                 440                 445

Lys Thr Lys Ile Arg Thr Thr Phe Lys Tyr Asn Met Tyr Ser Ser Phe
        450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
                485                 490                 495

Gln Ile Asp Gln Glu Val Gln Lys Val Val Ile Glu Thr Ser Gln His
                500                 505                 510

Gly Met Pro Val Lys Leu Lys Ala Leu Glu Glu Glu Ile His Arg Leu
            515                 520                 525

Thr Gln Leu Arg Ser Glu Met Gln Lys Gln Ile Pro Phe Asn Tyr Asn
            530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
                580                 585                 590

Leu Tyr Asp Ile Ala Lys Lys Asn Gly Gly Arg Ile Tyr Gly Asn Phe
                595                 600                 605

Phe Thr Thr Thr Ala Pro Ser Gly Arg Met Ser Cys Ser Asp Ile Asn
            610                 615                 620

Leu Gln Gln Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
                660                 665                 670

Asp Gly Ile Asp Leu His Lys Leu Thr Ala Ser Ile Leu Phe Asp Lys
                675                 680                 685

Lys Ile Asn Glu Val Ser Lys Glu Glu Arg Gln Ile Gly Lys Ser Ala
            690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735

Val Lys Lys Trp Lys Lys Phe Tyr Arg Lys Ile Ala Glu Gln His Gln
            740                 745                 750

Leu Ala Tyr Glu Arg Phe Lys Tyr Ala Glu Phe Val Asp Asn Glu Thr
                755                 760                 765

Trp Leu Asn Arg Pro Tyr Arg Ala Trp Lys Pro Gln Asp Leu Leu Asn
        770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Glu Ala Glu Asp Ile Ala
                820                 825                 830

Leu Leu Val Lys Gln Lys Met Glu Glu Ala Trp Asp Tyr Cys Leu Glu
            835                 840                 845
```

```
              Lys Ala Lys Glu Phe Gly Asn Asn Val Ala Asp Ile Lys Leu Glu Val
                  850                 855                 860

Glu Lys Pro Asn Ile Ser Ser Val Trp Glu Lys Glu
              865                 870                 875

<210> SEQ ID NO 46
<211> LENGTH: 2628
<212> TYPE: DNA
<213> ORGANISM: Artificial Sequence
<220> FEATURE:
<223> OTHER INFORMATION: M402 DNA

<400> SEQUENCE: 46
atgcgtggta tgcttccact gtttgaaccg aaaggccgtg tgctgctggt tgatggccac        60
catctggcct atcgtacctt ccatgcgctg aaaggcctga cgaccagccg cggcgaaccg       120
gtgcaggcgg tgtatgactt tgcgaaaagc ctgctgaaag cgctgaaaga agatggcgat       180
gcggttattg tggtgtttga tgcgaaagcc ccgagctttc gtcatgaagc gtatggcggc       240
tataaagcgg tcgtgcgcc gaccccggaa gattttccgc gtcagctggc cctgattaaa       300
gaactggtgg atctgctggg cctggcgcgt ctggaagtgc cgggctatga gcggatgat       360 gtgctggcca gctggccaa aaaagcggaa aagaaggct acgaagttcg tattctgacc       420
gccgataaag acctgtatca gctgctgtct gatcgtattc atgtgctgca tcctgagggt       480
tatctgatta ccccggcgtg gctgtgggaa aaatatggcc tgcgtccgga tcagtgggcg       540
gattatcgtg cgctgaccgg cgatgaaagc gataacctgc cgggcgtgaa aggcattggc       600
gaaaaaaccg cgcgtaaact gctggaagaa tggggcagcc tggaagcgct gctgaaaaac       660
ctggatcgtc tgaaaccggc gattcgtgaa agatcttag cgcacatgga tgatctgaaa       720
ctgagctggg atctggccaa agtgcgtacc gatctgccgc tggaagtgga ttttgcgaaa       780
cgtcgtgaac cggatcgtga acgtctgcgt gcgtttctgg aacgtctgga atttggcagc       840
ctgctgcatg aatttggcct gctggaaagc ggtggcggcg ttctggcgg tggtggcagc       900 aataccccga accgattct gaaaccgcag agcaaagcac tggttgaacc tgttctgtgt       960
gatagcattg atgaaattcc ggcaaaatac aatgaacctg tgtattttga tctgaaaacc      1020
gatgaagatc gtccggttct ggcaagcatt tatcagccgc attttgaacg taaagtgtat      1080
tgtctgaatc tgctgcgtga aaaactggca cgttttaaag aatggctgct gaaatttagc      1140
gaaattcgtg gttggggctt agatttcgat ctgcgtgttc tgggttatac ctatgaacag      1200
ctgcgcaaca aaaaaatcgt tgacgtccag ctggccatta agtgcagca ttatgaacgc      1260 tttaaacaag gtggcaccaa aggtgaaggt tttcgtctgg atgatgttgc acgtgatctg      1320
ctgggtattg aatatccgat gaacaaaacg aaaatccgca ccaccttcaa gtataacatg      1380
tatagcagct tttcgtacga gcaactgctg tatgcaagcc tggatgcata tattccgcat      1440
ctgctgtacg aacgtctgag cagcgatacc ctgaatagcc tggtttatca gattgatcaa      1500
gaggttcaga agtggtgat tgaaaccagc agcatggta tgccggttaa actgaaagca      1560
ctggaagaag aaattcatcg tctgacccag ctgcgtagcg aaatgcagaa acaaattccg      1620
tttaactata tagcccgaa acagaccgcc aaattctttg tgttaatag cagcagcaaa      1680 gatgttctga tggatctggc actgcgtggt aatgaagttg ccaaaaaagt tctggaagca      1740
cgccagattg aaaaaagtct ggcattcgcc aaagatctgt atgatatcgc caaaaaaaac      1800
ggtggtcgca tctatggtaa cttttttacc accaccgcac cgagcggtcg tatgagctgt      1860
agcgatatta acctgcagca aattccgcgt cgtctgcgtc cgtttattgg ttttgaaacc      1920
```

```
gaggacaaaa aactgatcac cgcagatttt ccgcagattg aactgcgtct ggcaggcgtt    1980
atgtggaatg aacctgaatt tctgaaagcc tttcgtgatg gcattgatct gcacaaactg    2040
accgcaagta ttctgttcga taaaaagatt aacgaagtga gcaaagagga acgccagatc    2100
ggtaaaagcg caaattttgg tctgatttat ggtatcagcc cgaaaggttt tgccgaatat    2160
tgtattagca acggcattaa catcaccgaa gaaatggcaa tcgagatcgt gaaaaaatgg    2220
aagaagttct atcgcaaaat cgccaacag catcagctgg catatgaacg tttcaaatat    2280
gccgaattcg tggataatga aacctggctg aatcgtccgt atcgtgcatg gaaaccgcaa    2340
gatctgctga actatcagat tcaaggtagc ggtgcagaac tgttcaaaaa agcaattgtt    2400
ctgctgaaag aagccaaacc ggatctgaaa attgtgaatc tggttcacga tgaaattgtg    2460
gtggaaacca gtaccgaaga agcagaagat attgcactgc tggtgaaaca aaagatggaa    2520
gaggcatggg attattgcct ggaaaaagca aagaatttg gcaataacgt ggccgacatt    2580
aaactggaag ttgaaaaacc gaatattagc agcgtgtggg aaaaagaa                2628
```

<210> SEQ ID NO 47
<211> LENGTH: 876
<212> TYPE: PRT
<213> ORGANISM: Artificial Sequence
<220> FEATURE:
<223> OTHER INFORMATION: M402 PRT

<400> SEQUENCE: 47

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Asp Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240
```

-continued

```
Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Gly Gly Gly Gly Ser Gly Gly Gly Gly Ser Asn Thr Pro Lys
    290                 295                 300

Pro Ile Leu Lys Pro Gln Ser Lys Ala Leu Val Glu Pro Val Leu Cys
305                 310                 315                 320

Asp Ser Ile Asp Glu Ile Pro Ala Lys Tyr Asn Glu Pro Val Tyr Phe
                325                 330                 335

Asp Leu Glu Thr Asp Glu Asp Arg Pro Val Leu Ala Ser Ile Tyr Gln
            340                 345                 350

Pro His Phe Glu Arg Lys Val Tyr Cys Leu Asn Leu Leu Arg Glu Lys
        355                 360                 365

Leu Ala Arg Phe Lys Glu Trp Leu Leu Lys Phe Ser Glu Ile Arg Gly
    370                 375                 380

Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
                405                 410                 415

His Tyr Glu Arg Phe Lys Gln Gly Gly Thr Lys Gly Glu Gly Phe Arg
            420                 425                 430

Leu Asp Asp Val Ala Arg Asp Leu Gly Ile Glu Tyr Pro Met Asn
    435                 440                 445

Lys Thr Lys Ile Arg Thr Thr Phe Lys Tyr Asn Met Tyr Ser Ser Phe
450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
                485                 490                 495

Gln Ile Asp Gln Glu Val Gln Lys Val Val Ile Glu Thr Ser Gln His
            500                 505                 510

Gly Met Pro Val Lys Leu Lys Ala Leu Glu Glu Ile His Arg Leu
    515                 520                 525

Thr Gln Leu Arg Ser Glu Met Gln Lys Gln Ile Pro Phe Asn Tyr Asn
    530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
            580                 585                 590

Leu Tyr Asp Ile Ala Lys Lys Asn Gly Gly Arg Ile Tyr Gly Asn Phe
    595                 600                 605

Phe Thr Thr Thr Ala Pro Ser Gly Arg Met Ser Cys Ser Asp Ile Asn
610                 615                 620

Leu Gln Gln Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655
```

Leu Ala Gly Val Met Trp Asn Glu Pro Glu Phe Leu Lys Ala Phe Arg
            660                 665                 670

Asp Gly Ile Asp Leu His Lys Leu Thr Ala Ser Ile Leu Phe Asp Lys
        675                 680                 685

Lys Ile Asn Glu Val Ser Lys Glu Glu Arg Gln Ile Gly Lys Ser Ala
    690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Met Ala Ile Glu Ile
                725                 730                 735

Val Lys Lys Trp Lys Lys Phe Tyr Arg Lys Ile Ala Glu Gln His Gln
        740                 745                 750

Leu Ala Tyr Glu Arg Phe Lys Tyr Ala Glu Phe Val Asp Asn Glu Thr
    755                 760                 765

Trp Leu Asn Arg Pro Tyr Arg Ala Trp Lys Pro Gln Asp Leu Leu Asn
770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
        805                 810                 815

Asp Glu Ile Val Val Glu Thr Ser Thr Glu Glu Ala Glu Asp Ile Ala
    820                 825                 830

Leu Leu Val Lys Gln Lys Met Glu Glu Ala Trp Asp Tyr Cys Leu Glu
    835                 840                 845

Lys Ala Lys Glu Phe Gly Asn Asn Val Ala Asp Ile Lys Leu Glu Val
    850                 855                 860

Glu Lys Pro Asn Ile Ser Ser Val Trp Glu Lys Glu
865                 870                 875

<210> SEQ ID NO 48
<211> LENGTH: 2628
<212> TYPE: DNA
<213> ORGANISM: Artificial Sequence
<220> FEATURE:
<223> OTHER INFORMATION: M403 DNA

<400> SEQUENCE: 48

```
atgcgtggta tgcttccact gtttgaaccg aaaggccgtg tgctgctggt tgatggccac     60
catctggcct atcgtacctt ccatgcgctg aaaggcctga cgaccagccg cggcgaaccg    120
gtgcaggcgg tgtatgactt tgcgaaaagc ctgctgaaag cgctgaaaga gatggcgat    180 gcggttattg tggtgtttga tgcgaaagcg ccgagctttc gtcatgaagc gtatggcggc    240
tataaagcgg tcgtgcgcc gacccggaa gattttccgc gtcagctggc cctgattaaa    300
gaactggtgg atctgctggg cctggcgcgt ctggaagtgc cgggctatga agcggatgat    360
gtgctggcca gctggccaa aaagcggaa aagaaggct acgaagttcg tattctgacc    420
gccgataaag acctgtatca gctgctgtct gatcgtattc atgtgctgca tcctgagggt    480
tatctgatta ccccggcgtg gctgtgggaa aaatatggcc tgcgtccgga tcagtgggcg    540
gattatcgtg cgctgaccgg cgatgaaagc gataacctgc cgggcgtgaa aggcattggc    600
gaaaaaaccg cgcgtaaact gctggaagaa tgggcagcc tggaagcgct gctgaaaaac    660
ctggatcgtc tgaaaccggc gattcgtgaa aagatcttag cgcacatgga tgatctgaaa    720
ctgagctggg atctggccaa agtgcgtacc gatctgccgc tggaagtgga ttttgcgaaa    780
cgtcgtgaac cggatcgtga acgtctgcgt gcgtttctgg aacgtctgga atttggcagc    840
```

```
ctgctgcatg aatttggcct gctggaaagc ggtggcggcg ttctggcgg tggtggcagc      900
aataccccga aaccgattct gaaaccgcag agcaaagcac tggttgaacc tgttctgtgt      960
gatagcattg atgaaattcc ggcaaaatac aatgaacctg tgtattttga tctggcaacc     1020
gatgaagatc gtccggttct ggcaagcatt tatcagccgc attttgaacg taaagtgtat     1080
tgtctgaatc tgctgcgtga aaaactggca cgttttaaag aatggctgct gaaatttagc     1140
gaaattcgtg ttggggcttt agatttcgat ctgcgtgttc tgggttatac ctatgaacag     1200
ctgcgcaaca aaaaaatcgt tgacgtccag ctggccatta agtgcagca ttatgaacgc      1260
tttaaacaag gtggcaccaa aggtgaaggt tttcgtctgg atgatgttgc acgtgatctg     1320
ctgggtattg aatatccgat gaacaaaacg aaaatccgca ccaccttcaa gtataacatg     1380
tatagcagct tttcgtacga gcaactgctg tatgcaagcc tggatgcata tattccgcat     1440
ctgctgtacg aacgtctgag cagcgatacc ctgaatagcc tggtttatca gattgatcaa     1500
gaggttcaga agtggtgat tgaaaccagc cagcatggta tgccggttaa actgaaagca     1560
ctggaagaag aaattcatcg tctgacccag ctgcgtagcg aaatgcagaa acaaattccg     1620
tttaactata atagcccgaa acagaccgcc aaattctttg gtgttaatag cagcagcaaa     1680
gatgttctga tggatctggc actgcgtggt aatgaagttg ccaaaaaagt tctggaagca     1740
cgccagattg aaaaaagtct ggcattcgcc aaagatctgt atgatatcgc caaaaaaaac     1800
ggtggtcgca tctatggtaa cttttttacc accaccgcac cgagcggtcg tatgagctgt     1860
agcgatatta acctgcagca aattccgcgt cgtctgcgtc cgtttattgg ttttgaaacc     1920
gaggacaaaa aactgatcac cgcagatttt ccgcagattg aactgcgtct ggcaggcgtt     1980
atgtggaatg aacctgaatt tctgaaagcc tttcgtgatg gcattgatct gcacaaactg     2040
accgcaagta ttctgttcga taaaaagatt aacgaagtga gcaaagagga acgccagatc     2100
ggtaaaagcg caaattttgg tctgatttat ggtatcagcc cgaaaggttt tgccgaatat     2160
tgtattagca acggcattaa catcaccgaa gaaatggcaa tcgagatcgt gaaaaaatgg     2220
aagaagttct atcgcaaaat cgccgaacag catcagctgg catatgaacg tttcaaatat     2280
gccgaattcg tggataatga aacctggctg aatcgtccgt atcgtgcatg gaaaccgcaa     2340
gatctgctga actatcagat tcaaggtagc ggtgcagaac tgttcaaaaa agcaattgtt     2400
ctgctgaaag aagccaaacc ggatctgaaa attgtgaatc tggttcacga tgaaattgtg     2460
gtggaaacca gtaccgaaga agcagaagat attgcactgc tggtgaaaca aaagatggaa     2520
gaggcatggg attattgcct ggaaaaagca aagaatttg gcaataacgt ggccgacatt     2580
aaactggaag ttgaaaaacc gaatattagc agcgtgtggg aaaaagaa               2628
```

<210> SEQ ID NO 49
<211> LENGTH: 876
<212> TYPE: PRT
<213> ORGANISM: Artificial Sequence
<220> FEATURE:
<223> OTHER INFORMATION: M403 PRT

<400> SEQUENCE: 49

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Asp Phe Ala
        35                  40                  45
```

```
Lys Ser Leu Leu Lys Ala Leu Lys Glu Asp Gly Asp Ala Val Ile Val
    50              55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Gly Leu Ala Arg Leu Glu
            100                 105                 110

Val Pro Gly Tyr Glu Ala Asp Val Leu Ala Ser Leu Ala Lys Lys
            115                 120                 125

Ala Glu Lys Glu Gly Tyr Glu Val Arg Ile Leu Thr Ala Asp Lys Asp
        130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Gly Gly Gly Ser Gly Gly Gly Ser Asn Thr Pro Lys
290                 295                 300

Pro Ile Leu Lys Pro Gln Ser Lys Ala Leu Val Glu Pro Val Leu Cys
305                 310                 315                 320

Asp Ser Ile Asp Glu Ile Pro Ala Lys Tyr Asn Glu Pro Val Tyr Phe
                325                 330                 335

Asp Leu Ala Thr Asp Glu Asp Arg Pro Val Leu Ala Ser Ile Tyr Gln
            340                 345                 350

Pro His Phe Glu Arg Lys Val Tyr Cys Leu Asn Leu Leu Arg Glu Lys
        355                 360                 365

Leu Ala Arg Phe Lys Glu Trp Leu Leu Lys Phe Ser Glu Ile Arg Gly
370                 375                 380

Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
            405                 410                 415

His Tyr Glu Arg Phe Lys Gln Gly Gly Thr Lys Gly Glu Gly Phe Arg
        420                 425                 430

Leu Asp Asp Val Ala Arg Asp Leu Leu Gly Ile Glu Tyr Pro Met Asn
            435                 440                 445

Lys Thr Lys Ile Arg Thr Thr Phe Lys Tyr Asn Met Tyr Ser Ser Phe
450                 455                 460
```

```
Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
            485                 490                 495

Gln Ile Asp Gln Glu Val Gln Lys Val Val Ile Glu Thr Ser Gln His
                500                 505                 510

Gly Met Pro Val Lys Leu Lys Ala Leu Glu Glu Ile His Arg Leu
            515                 520                 525

Thr Gln Leu Arg Ser Glu Met Gln Lys Gln Ile Pro Phe Asn Tyr Asn
    530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
            580                 585                 590

Leu Tyr Asp Ile Ala Lys Asn Gly Gly Arg Ile Tyr Gly Asn Phe
    595                 600                 605

Phe Thr Thr Thr Ala Pro Ser Gly Arg Met Ser Cys Ser Asp Ile Asn
    610                 615                 620

Leu Gln Gln Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
                660                 665                 670

Asp Gly Ile Asp Leu His Lys Leu Thr Ala Ser Ile Leu Phe Asp Lys
            675                 680                 685

Lys Ile Asn Glu Val Ser Lys Glu Glu Arg Gln Ile Gly Lys Ser Ala
    690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735

Val Lys Lys Trp Lys Lys Phe Tyr Arg Lys Ile Ala Glu Gln His Gln
            740                 745                 750

Leu Ala Tyr Glu Arg Phe Lys Tyr Ala Glu Phe Val Asp Asn Glu Thr
    755                 760                 765

Trp Leu Asn Arg Pro Tyr Arg Ala Trp Lys Pro Gln Asp Leu Leu Asn
    770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
            805                 810                 815

Asp Glu Ile Val Val Glu Thr Ser Thr Glu Glu Ala Glu Asp Ile Ala
                820                 825                 830

Leu Leu Val Lys Gln Lys Met Glu Glu Ala Trp Asp Tyr Cys Leu Glu
            835                 840                 845

Lys Ala Lys Glu Phe Gly Asn Asn Val Ala Asp Ile Lys Leu Glu Val
    850                 855                 860

Glu Lys Pro Asn Ile Ser Ser Val Trp Glu Lys Glu
865                 870                 875
```

<210> SEQ ID NO 50
<211> LENGTH: 2628
<212> TYPE: DNA
<213> ORGANISM: Artificial Sequence
<220> FEATURE:
<223> OTHER INFORMATION: M501 DNA

<400> SEQUENCE: 50

| | |
|---|---:|
| atgcgtggta tgcttccact gtttgaaccg aaaggccgtg tgctgctggt tgatggccac | 60 |
| catctggcct atcgtacctt ccatgcgctg aaaggcctga cgaccagccg cggcgaaccg | 120 |
| gtgcaggcgg tgtatggctt tgcgaaaagc ctgctgaaag cgctgaaaga gatggcgat | 180 |
| gcggttattg tggtgtttga tgcgaaagcg ccgagctttc gtcatgaagc gtatggcggc | 240 |
| tataaagcgg tcgtgcgcc gaccccggaa gattttccgc gtcagctggc cctgattaaa | 300 |
| gaactggtgg atctgctggg cctggcgcgt ctggaagtgc cgggctatga gcggatgat | 360 |
| gtgctggcca gcctggccaa aaagcggaa aagaaggct acgaagttcg tattctgacc | 420 |
| gccgataaag acctgtatca gctgctgtct gatcgtattc atgtgctgca tcctgagggt | 480 |
| tatctgatta ccccggcgtg gctgtgggaa aaatatggcc tgcgtccgga tcagtgggcg | 540 |
| gattatcgtg cgctgaccgg cgatgaaagc gataacctgc cggcgtgaa aggcattggc | 600 |
| gaaaaaccg cgcgtaaact gctggaagaa tgggcagcc tggaagcgct gctgaaaaac | 660 |
| ctggatcgtc tgaaaccggc gattcgtgaa aagatcttag cgcacatgga tgatctgaaa | 720 |
| ctgagctggg atctggccaa agtgcgtacc gatctgccgc tggaagtgga ttttgcgaaa | 780 |
| cgtcgtgaac cggatcgtga acgtctgcgt gcgtttctgg aacgtctgga atttggcagc | 840 |
| ctgctgcatg aatttggcct gctggaaagc ggtggcggcg ttctggcgg tggtggcagc | 900 |
| aatacccga accgattct gaaaccgcag agcaaagcac tggttgaacc tgttctgtgt | 960 |
| gatagcattg atgaaattcc ggcaaaatac aatgaacctg tgtattttga tctggcaacc | 1020 |
| gatgaagatc gtccggttct ggcaagcatt tatcagccgc attttgaacg taaagtgtat | 1080 |
| tgtctgaatc tgctgcgtga aaactggca cgttttaaag aatggctgct gaaatttagc | 1140 |
| gaaattcgtg ttggggctt agatttcgat ctgcgtgttc tgggttatac ctatgaacag | 1200 |
| ctgcgcaaca aaaaaatcgt tgacgtccag ctggccatta agtgcagca ttatgaacgc | 1260 |
| tttaaacaag gtggcaccaa aggtgaaggt tttcgtctgg atgatgttgc acgtgatctg | 1320 |
| ctgggtattg aatatccgat gaacaaaacg aaaatccgca ccaccttcaa gtataacatg | 1380 |
| tatagcagct tttcgtacga gcaactgctg tatgcaagcc tggatgcata tattccgcat | 1440 |
| ctgctgtacg aacgtctgag cagcgatacc ctgaatagcc tggtttatca gattgatcaa | 1500 |
| gaggttcaga agtggtgat tgaaaccagc cagcatggta tgccggttaa actgaaagca | 1560 |
| ctggaagaag aaattcatcg tctgacccag ctgcgtagcg aaatgcagaa acaaattccg | 1620 |
| tttaactata atagcccgaa acagaccgcc aaattctttg tgttaatag cagcagcaaa | 1680 |
| gatgttctga tggatctggc actgcgtggt aatgaagttg ccaaaaaagt tctggaagca | 1740 |
| cgccagattg aaaaaagtct ggcattcgcc aaagatctgt atgatatcgc caaaaaaac | 1800 |
| ggtggtcgca tctatggtaa cttttttacc accaccgcac cgagcggtcg tatgagctgt | 1860 |
| agcgatatta acctgcagca aattccgcgt cgtctgcgtc cgtttattgg ttttgaaacc | 1920 |
| gaggacaaaa aactgatcac cgcagatttt ccgcagattg aactgcgtct ggcaggcgtt | 1980 |
| atgtggaatg aacctgaatt tctgaaagcc tttcgtgatg cattgatct gcacaaactg | 2040 |
| accgcaagta ttctgttcga taaaaagatt aacgaagtga gcaaagagga acgccagatc | 2100 |

-continued

```
ggtaaaagcg caaattttgg tctgatttat ggtatcagcc cgaaaggttt tgccgaatat    2160
tgtattagca acggcattaa catcaccgaa gaaatggcaa tcgagatcgt gaaaaaatgg    2220
aagaagttct atcgcaaaat cgccgaacag cagaagaagg catatgaacg tttcaaatat    2280
gccgaattcg tggataatga aacctggctg aatcgtccgt atcgtgcatg gaaaccgcaa    2340
gatctgctga actatcagat tcaaggtagc ggtgcagaac tgttcaaaaa agcaattgtt    2400
ctgctgaaag aagccaaacc ggatctgaaa attgtgaatc tagttcacga tgaaattgtg    2460
gtggaaacca gtaccgaaga agcagaagat attgcactgc tggtgaaaca aagatggaa    2520 gaggcatggg attattgcct ggaaaaagca aaagaatttg caataacgt ggccgacatt    2580 aaactggaag ttgaaaaacc gaatattagc agcgtgtggg aaaaagaa                 2628
```

<210> SEQ ID NO 51
<211> LENGTH: 876
<212> TYPE: PRT
<213> ORGANISM: Artificial Sequence
<220> FEATURE:
<223> OTHER INFORMATION: M501 PRT

<400> SEQUENCE: 51

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270
```

```
Leu Glu Arg Leu Glu Phe Gly Ser Leu Leu His Glu Phe Gly Leu Leu
            275                 280                 285

Glu Ser Gly Gly Gly Ser Gly Gly Gly Ser Asn Thr Pro Lys
290                 295                 300

Pro Ile Leu Lys Pro Gln Ser Lys Ala Leu Val Glu Pro Val Leu Cys
305                 310                 315                 320

Asp Ser Ile Asp Glu Ile Pro Ala Lys Tyr Asn Glu Pro Val Tyr Phe
            325                 330                 335

Asp Leu Ala Thr Asp Glu Asp Arg Pro Val Leu Ala Ser Ile Tyr Gln
            340                 345                 350

Pro His Phe Glu Arg Lys Val Tyr Cys Leu Asn Leu Leu Arg Glu Lys
            355                 360                 365

Leu Ala Arg Phe Lys Glu Trp Leu Leu Lys Phe Ser Glu Ile Arg Gly
            370                 375                 380

Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
                405                 410                 415

His Tyr Glu Arg Phe Lys Gln Gly Gly Thr Lys Gly Glu Gly Phe Arg
            420                 425                 430

Leu Asp Asp Val Ala Arg Asp Leu Leu Gly Ile Glu Tyr Pro Met Asn
            435                 440                 445

Lys Thr Lys Ile Arg Thr Thr Phe Lys Tyr Asn Met Tyr Ser Ser Phe
            450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
                485                 490                 495

Gln Ile Asp Gln Glu Val Gln Lys Val Val Ile Glu Thr Ser Gln His
            500                 505                 510

Gly Met Pro Val Lys Leu Lys Ala Leu Glu Glu Ile His Arg Leu
            515                 520                 525

Thr Gln Leu Arg Ser Glu Met Gln Lys Gln Ile Pro Phe Asn Tyr Asn
530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
            580                 585                 590

Leu Tyr Asp Ile Ala Lys Lys Asn Gly Gly Arg Ile Tyr Gly Asn Phe
            595                 600                 605

Phe Thr Thr Thr Ala Pro Ser Gly Arg Met Ser Cys Ser Asp Ile Asn
            610                 615                 620

Leu Gln Gln Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
            660                 665                 670

Asp Gly Ile Asp Leu His Lys Leu Thr Ala Ser Ile Leu Phe Asp Lys
            675                 680                 685

Lys Ile Asn Glu Val Ser Lys Glu Glu Arg Gln Ile Gly Lys Ser Ala
```

```
Asn Phe Gly Leu Ile Tyr Gly Ile Ser Pro Lys Gly Phe Ala Glu Tyr
            705                 710                 715                 720

Cys Ile Ser Asn Gly Ile Asn Ile Thr Glu Glu Met Ala Ile Glu Ile
                    725                 730                 735

Val Lys Lys Trp Lys Lys Phe Tyr Arg Lys Ile Ala Glu Gln Gln Lys
                740                 745                 750

Lys Ala Tyr Glu Arg Phe Lys Tyr Ala Glu Phe Val Asp Asn Glu Thr
            755                 760                 765

Trp Leu Asn Arg Pro Tyr Arg Ala Trp Lys Pro Gln Asp Leu Leu Asn
        770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Glu Ala Glu Asp Ile Ala
                820                 825                 830

Leu Leu Val Lys Gln Lys Met Glu Glu Ala Trp Asp Tyr Cys Leu Glu
            835                 840                 845

Lys Ala Lys Glu Phe Gly Asn Asn Val Ala Asp Ile Lys Leu Glu Val
        850                 855                 860

Glu Lys Pro Asn Ile Ser Ser Val Trp Glu Lys Glu
865                 870                 875
```

<210> SEQ ID NO 52
<211> LENGTH: 2628
<212> TYPE: DNA
<213> ORGANISM: Artificial Sequence
<220> FEATURE:
<223> OTHER INFORMATION: M502 DNA

<400> SEQUENCE: 52

```
atgcgtggta tgcttccact gtttgaaccg aaaggccgtg tgctgctggt tgatggccac     60
catctggcct atcgtacctt ccatgcgctg aaaggcctga cgaccagccg cggcgaaccg    120
gtgcaggcgg tgtatggctt tgcgaaaagc ctgctgaaag cgctgaaaga agatggcgat    180
gcggttattg tggtgtttga tgcgaaagcg ccgagctttc gtcatgaagc gtatggcggc    240
tataaagcgg tcgtgcgcc gaccccggaa gattttccgc gtcagctggc cctgattaaa    300
gaactggtgg atctgctggg cctggcgcgt ctggaagtgc cgggctatga gcggatgat     360 gtgctggcca gcctggccaa aaaagcggaa aagaaggct acgaagttcg tattctgacc    420
gccgataaag acctgtatca gctgctgtct gatcgtattc atgtgctgca tcctgagggt    480
tatctgatta ccccggcgtg gctgtgggaa aaatatggcc tgcgtccgga tcagtgggcg    540
gattatcgtg cgctgaccgg cgatgaaagc gataacctgc cgggcgtgaa aggcattggc    600
gaaaaaaccg cgcgtaaact gctggaagaa tggggcagcc tggaagcgct gctgaaaaac    660
ctggatcgtc tgaaaccggc gattcgtgaa aagatcttag cgcacatgga tgatctgaaa    720
ctgagctggg atctggccaa agtgcgtacc gatctgccgc tggaagtgga ttttgcgaaa    780
cgtcgtgaac cggatcgtga acgtctgcgt gcgtttctgg aacgtctgga atttggcagc    840
ctgctgcatg aatttggcct gctggaaagc ggtggcggcg ttctggcgg tggtggcagc    900 aataccccga aaccgattct gaaaccgcag agcaaagcac tggttgaacc tgttctgtgt    960
gatagcattg atgaaattcc ggcaaaatac aatgaacctg tgtattttga tctggcaacc   1020
```

|         |         |         |         |         |         |      |
|---------|---------|---------|---------|---------|---------|------|
| gatgaagatc | gtccggttct | ggcaagcatt | tatcagccgc | attttgaacg | taaagtgtat | 1080 |
| tgtctgaatc | tgctgcgtga | aaaactggca | cgttttaaag | aatggctgct | gaaatttagc | 1140 |
| gaaattcgtg | gttggggctt | agatttcgat | ctgcgtgttc | tgggttatac | ctatgaacag | 1200 |
| ctgcgcaaca | aaaaaatcgt | tgacgtccag | ctggccatta | aagtgcagca | ttatgaacgc | 1260 |
| tttaaacaag | gtggcaccaa | aggtgaaggt | tttcgtctgg | atgatgttgc | acgtgatctg | 1320 |
| ctgggtattg | aatatccgat | gaacaaaacg | aaaatccgca | ccaccttcaa | gtataacatg | 1380 |
| tatagcagct | tttcgtacga | gcaactgctg | tatgcaagcc | tggatgcata | tattccgcat | 1440 |
| ctgctgtacg | aacgtctgag | cagcgatacc | ctgaatagcc | tggtttatca | gattgatcaa | 1500 |
| gaggttcaga | agtggtgat | tgaaaccagc | cagcatggta | tgccggttaa | actgaaagca | 1560 |
| ctggaagaag | aaattcatcg | tctgacccag | ctgcgtagcg | aaatgcagaa | acaaattccg | 1620 |
| tttaactata | atagcccgaa | acagaccgcc | aaattctttg | gtgttaatag | cagcagcaaa | 1680 |
| gatgttctga | tggatctggc | actgcgtggt | aatgaagttg | ccaaaaaagt | tctggaagca | 1740 |
| cgccagattg | aaaaaagtct | ggcattcgcc | aaagatctgt | atgatatcgc | caaaaaaaac | 1800 |
| ggtggtcgca | tctatggtaa | cttttttacc | accaccgcac | cgagcggtcg | tatgagctgt | 1860 |
| agcaatatta | acctgcagaa | cattccgcgt | cgtctgcgtc | cgtttattgg | ttttgaaacc | 1920 |
| gaggacaaaa | aactgatcac | cgcagatttt | ccgcagattg | aactgcgtct | ggcaggcgtt | 1980 |
| atgtggaatg | aacctgaatt | tctgaaagcc | tttcgtgatg | cattgatct | gcacaaactg | 2040 |
| accgcaagta | ttctgttcga | taaaaagatt | aacgaagtga | gcaaagagga | acgccagatc | 2100 |
| ggtaaaagcg | caaattttgg | tctgatttat | ggtatcagcc | cgaaaggttt | tgccgaatat | 2160 |
| tgtattagca | acggcattaa | catcaccgaa | gaaatggcaa | tcgagatcgt | gaaaaaatgg | 2220 |
| aagaagttct | atcgcaaaat | cgccgaacag | catcagctgg | catatgaacg | tttcaaatat | 2280 |
| gccgaattcg | tggataatga | aacctggctg | aatcgtccgt | atcgtgcttg | caaaccgcaa | 2340 |
| gccctgctta | actatcagat | tcaaggtagc | ggtgcagaac | tgttcaaaaa | agcaattgtt | 2400 |
| ctgctgaaag | aagccaaacc | ggatctgaaa | attgtgaatc | tggttcacga | tgaaattgtg | 2460 |
| gtggaaacca | gtaccgaaga | agcagaagat | attgcactgc | tggtgaaaca | aaagatggaa | 2520 |
| gaggcatggg | attattgcct | ggaaaaagca | aaagaatttg | gcaataacgt | ggccgacatt | 2580 |
| aaactggaag | ttgaaaaacc | gaatattagc | agcgtgtggg | aaaaagaa |         | 2628 |

<210> SEQ ID NO 53
<211> LENGTH: 876
<212> TYPE: PRT
<213> ORGANISM: Artificial Sequence
<220> FEATURE:
<223> OTHER INFORMATION: M502 PRT

<400> SEQUENCE: 53

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80
```

```
Tyr Lys Ala Gly Arg Ala Pro Thr Pro Glu Asp Phe Pro Arg Gln Leu
            85                  90                  95
Ala Leu Ile Lys Glu Leu Val Asp Leu Gly Leu Ala Arg Leu Glu
            100                 105                 110
Val Pro Gly Tyr Glu Ala Asp Asp Val Leu Ala Ser Leu Ala Lys Lys
            115                 120                 125
Ala Glu Lys Glu Gly Tyr Glu Val Arg Ile Leu Thr Ala Asp Lys Asp
            130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
            165                 170                 175
Asp Gln Trp Ala Asp Tyr Arg Ala Leu Thr Gly Asp Glu Ser Asp Asn
            180                 185                 190
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
            210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
            245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
            275                 280                 285
Glu Ser Gly Gly Gly Ser Gly Gly Gly Ser Asn Thr Pro Lys
            290                 295                 300
Pro Ile Leu Lys Pro Gln Ser Lys Ala Leu Val Glu Pro Val Leu Cys
305                 310                 315                 320
Asp Ser Ile Asp Glu Ile Pro Ala Lys Tyr Asn Glu Pro Val Tyr Phe
            325                 330                 335
Asp Leu Ala Thr Asp Glu Asp Arg Pro Val Leu Ala Ser Ile Tyr Gln
            340                 345                 350
Pro His Phe Glu Arg Lys Val Tyr Cys Leu Asn Leu Arg Glu Lys
            355                 360                 365
Leu Ala Arg Phe Lys Glu Trp Leu Leu Lys Phe Ser Glu Ile Arg Gly
            370                 375                 380
Trp Gly Leu Asp Phe Asp Leu Arg Val Leu Gly Tyr Thr Tyr Glu Gln
385                 390                 395                 400
Leu Arg Asn Lys Lys Ile Val Asp Val Gln Leu Ala Ile Lys Val Gln
            405                 410                 415
His Tyr Glu Arg Phe Lys Gln Gly Gly Thr Lys Gly Glu Gly Phe Arg
            420                 425                 430
Leu Asp Asp Val Ala Arg Asp Leu Leu Gly Ile Glu Tyr Pro Met Asn
            435                 440                 445
Lys Thr Lys Ile Arg Thr Thr Phe Lys Tyr Asn Met Tyr Ser Ser Phe
            450                 455                 460
Ser Tyr Glu Gln Leu Leu Tyr Ala Ser Leu Asp Ala Tyr Ile Pro His
465                 470                 475                 480
Leu Leu Tyr Glu Arg Leu Ser Ser Asp Thr Leu Asn Ser Leu Val Tyr
            485                 490                 495
Gln Ile Asp Gln Glu Val Gln Lys Val Val Ile Glu Thr Ser Gln His
```

```
            500                 505                 510
Gly Met Pro Val Lys Leu Lys Ala Leu Glu Glu Ile His Arg Leu
        515                 520                 525

Thr Gln Leu Arg Ser Glu Met Gln Lys Gln Ile Pro Phe Asn Tyr Asn
        530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
                580                 585                 590

Leu Tyr Asp Ile Ala Lys Lys Asn Gly Gly Arg Ile Tyr Gly Asn Phe
                595                 600                 605

Phe Thr Thr Thr Ala Pro Ser Gly Arg Met Ser Cys Ser Asn Ile Asn
                610                 615                 620

Leu Gln Asn Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
                660                 665                 670

Asp Gly Ile Asp Leu His Lys Leu Thr Ala Ser Ile Leu Phe Asp Lys
                675                 680                 685

Lys Ile Asn Glu Val Ser Lys Glu Arg Gln Ile Gly Lys Ser Ala
                690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735

Val Lys Lys Trp Lys Lys Phe Tyr Arg Lys Ile Ala Glu Gln His Gln
                740                 745                 750

Leu Ala Tyr Glu Arg Phe Lys Tyr Ala Glu Phe Val Asp Asn Glu Thr
                755                 760                 765

Trp Leu Asn Arg Pro Tyr Arg Ala Cys Lys Pro Gln Ala Leu Leu Asn
770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Glu Ala Glu Asp Ile Ala
                820                 825                 830

Leu Leu Val Lys Gln Lys Met Glu Glu Ala Trp Asp Tyr Cys Leu Glu
                835                 840                 845

Lys Ala Lys Glu Phe Gly Asn Asn Val Ala Asp Ile Lys Leu Glu Val
                850                 855                 860

Glu Lys Pro Asn Ile Ser Ser Val Trp Glu Lys Glu
865                 870                 875

<210> SEQ ID NO 54
<211> LENGTH: 2628
<212> TYPE: DNA
<213> ORGANISM: Artificial Sequence
<220> FEATURE:
<223> OTHER INFORMATION: M503 DNA
```

<400> SEQUENCE: 54

```
atgcgtggta tgcttccact gtttgaaccg aaaggccgtg tgctgctggt tgatggccac       60
catctggcct atcgtacctt ccatgcgctg aaaggcctga cgaccagccg cggcgaaccg      120
gtgcaggcgg tgtatggctt tgcgaaaagc ctgctgaaag cgctgaaaga gatggcgat      180
gcggttattg tggtgtttga tgcgaaagcg ccgagctttc gtcatgaagc gtatggcggc     240
tataaagcgg tcgtgcgcc gaccccggaa gattttccgc gtcagctggc cctgattaaa      300
gaactggtgg atctgctggg cctggcgcgt ctggaagtgc cgggctatga agcggatgat     360
gtgctggcca gcctggccaa aaaagcggaa aagaaggct acgaagttcg tattctgacc      420
gccgataaag acctgtatca gctgctgtct gatcgtattc atgtgctgca tcctgagggt     480
tatctgatta ccccggcgtg gctgtgggaa aaatatggcc tgcgtccgga tcagtgggcg     540
gattatcgtg cgctgaccgg cgatgaaagc gataacctgc cgggcgtgaa aggcattggc    600
gaaaaaaccg cgcgtaaact gctggaagaa tggggcagcc tggaagcgct gctgaaaaac   660
ctggatcgtc tgaaaccggc gattcgtgaa aagatcttag cgcacatgga tgatctgaaa   720
ctgagctggg atctgccaa agtgcgtacc gatctgccgc tggaagtgga ttttgcgaaa    780
cgtcgtgaac cggatcgtga acgtctgcgt gcgtttctgg aacgtctgga atttggcagc   840
ctgctgcatg aatttggcct gctggaaagc ggtggcggcg ttctggcgg tggtggcagc    900
aatacccga aaccgattct gaaaccgcag agcaaagcac tggttgaacc tgttctgtgt     960
gatagcattg atgaaattcc ggcaaaatac aatgaacctg tgtattttga tctggcaacc   1020
gatgaagatc gtccggttct ggcaagcatt tatcagccgc attttgaacg taaagtgtat  1080
tgtctgaatc tgctgcgtga aaaactggca cgttttaaag aatggctgct gaaatttagc   1140
gaaattcgtg gttggggctt agatttcgat ctgcgtgttc tgggttatac ctatgaacag   1200
ctgcgcaaca aaaaaatcgt tgacgtccag ctggccatta agtgcagca ttatgaacgc    1260
tttaaacaag gtggcaccaa aggtgaaggt tttcgtctgg atgatgttgc acgtgatctg  1320
ctgggtattg aatatccgat gaacaaaacg aaaatccgca ccaccttcaa gtataacatg   1380
tatagcagct tttcgtacga gcaactgctg tatgcaagcc tggatgcata tattccgcat   1440
ctgctgtacg aacgtctgag cagcgatacc ctgaatagcc tggtttatca gattgatcaa   1500
gaggttcaga agtggtgat tgaaaccagc cagcatggta tgccggttaa actgaaagca   1560
ctggaagaag aaattcatcg tctgacccag ctgcgtagcg aaatgcagaa acaaattccg   1620
tttaactata atagcccgaa acagaccgcc aaattctttg tgttaatag cagcagcaaa    1680
gatgttctga tggatctggc actgcgtggt aatgaagttg ccaaaaaagt tctggaagca   1740
cgccagattg aaaaaagtct ggcattcgcc aaagatctgt atgatatcgc caaaaaaaac   1800
ggtggtcgca tctatggtaa cttttttacc accaccgcac cgagcggtcg tatgagctgt   1860
agcgatatta acctgcagaa cattccgcgt cgtctgcgtc cgtttattgg ttttgaaacc   1920
gaggacaaaa aactgatcac cgcagatttt ccgcagattt aactgcgtct ggcaggcgtt   1980
atgtggaatg aacctgaatt tctgaaagcc tttcgtgatg cattgatct gcacaaactg    2040
accgcaagta ttctgttcga taaaaagatt aacgaagtga gcaaagagga acgccagatc    2100
ggtaaaagcg caaattttgg tctgatttat ggtatcagcc cgaaaggttt tgccgaatat    2160
tgtattagca acggcattaa catcaccgaa gaaatggcaa tcgagatcgt gaaaaaatgg   2220
aagaagttct atcgcaaaat cgccgaacag cagaagaagg catatgaacg tttcaaatat   2280
gccgaattcg tggataatga aacctggctg aatcgtccgt atcgtgcatg gaaaccgcaa   2340
```

-continued

```
gatctgctga actatcagat tcaaggtagc ggtgcagaac tgttcaaaaa agcaattgtt    2400
ctgctgaaag aagccaaacc ggatctgaaa attgtgaatc tggttcacga tgaaattgtg    2460
gtggaaacca gtaccgaaga agcagaagat attgcactgc tggtgaaaca aaagatggaa    2520
gaggcatggg attattgcct ggaaaaagca aaagaatttg gcaataacgt ggccgacatt    2580
aaactggaag ttgaaaaacc gaatattagc agcgtgtggg aaaaagaa                 2628
```

<210> SEQ ID NO 55
<211> LENGTH: 876
<212> TYPE: PRT
<213> ORGANISM: Artificial Sequence
<220> FEATURE:
<223> OTHER INFORMATION: M503 PRT

<400> SEQUENCE: 55

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Gly Gly Gly Gly Ser Gly Gly Gly Ser Asn Thr Pro Lys
    290                 295                 300

Pro Ile Leu Lys Pro Gln Ser Lys Ala Leu Val Glu Pro Val Leu Cys
```

```
            305                 310                 315                 320
Asp Ser Ile Asp Glu Ile Pro Ala Lys Tyr Asn Glu Pro Val Tyr Phe
                325                 330                 335

Asp Leu Ala Thr Asp Glu Asp Arg Pro Val Leu Ala Ser Ile Tyr Gln
                340                 345                 350

Pro His Phe Glu Arg Lys Val Tyr Cys Leu Asn Leu Leu Arg Glu Lys
                355                 360                 365

Leu Ala Arg Phe Lys Glu Trp Leu Leu Lys Phe Ser Glu Ile Arg Gly
370                 375                 380

Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
                405                 410                 415

His Tyr Glu Arg Phe Lys Gln Gly Gly Thr Lys Gly Glu Gly Phe Arg
                420                 425                 430

Leu Asp Asp Val Ala Arg Asp Leu Leu Gly Ile Glu Tyr Pro Met Asn
                435                 440                 445

Lys Thr Lys Ile Arg Thr Thr Phe Lys Tyr Asn Met Tyr Ser Ser Phe
                450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
                485                 490                 495

Gln Ile Asp Gln Glu Val Gln Lys Val Val Ile Glu Thr Ser Gln His
                500                 505                 510

Gly Met Pro Val Lys Leu Lys Ala Leu Glu Glu Ile His Arg Leu
                515                 520                 525

Thr Gln Leu Arg Ser Glu Met Gln Lys Gln Ile Pro Phe Asn Tyr Asn
                530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
                580                 585                 590

Leu Tyr Asp Ile Ala Lys Lys Asn Gly Gly Arg Ile Tyr Gly Asn Phe
                595                 600                 605

Phe Thr Thr Thr Ala Pro Ser Gly Arg Met Ser Cys Ser Asp Ile Asn
                610                 615                 620

Leu Gln Asn Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
                660                 665                 670

Asp Gly Ile Asp Leu His Lys Leu Thr Ala Ser Ile Leu Phe Asp Lys
                675                 680                 685

Lys Ile Asn Glu Val Ser Lys Glu Glu Arg Gln Ile Gly Lys Ser Ala
                690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735
```

```
Val Lys Lys Trp Lys Lys Phe Tyr Arg Lys Ile Ala Glu Gln Gln Lys
                740                 745                 750

Lys Ala Tyr Glu Arg Phe Lys Tyr Ala Glu Phe Val Asp Asn Glu Thr
            755                 760                 765

Trp Leu Asn Arg Pro Tyr Arg Ala Trp Lys Pro Gln Asp Leu Leu Asn
    770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Ala Glu Asp Ile Ala
            820                 825                 830

Leu Leu Val Lys Gln Lys Met Glu Glu Ala Trp Asp Tyr Cys Leu Glu
        835                 840                 845

Lys Ala Lys Glu Phe Gly Asn Asn Val Ala Asp Ile Lys Leu Glu Val
850                 855                 860

Glu Lys Pro Asn Ile Ser Ser Val Trp Glu Lys Glu
865                 870                 875

<210> SEQ ID NO 56
<211> LENGTH: 1940
<212> TYPE: DNA
<213> ORGANISM: Artificial Sequence
<220> FEATURE:
<223> OTHER INFORMATION: ACTB plasmid

<400> SEQUENCE: 56
gagtgagcgg cgcggggcca atcagcgtgc gccgttccga agttgccttt tatggctcg     60
agcggccgcg gcggcgccct ataaaaccca gcggcgcgac gcgccaccac cgccgagacc   120
gcgtccgccc cgcgagcaca gagcctcgcc tttgccgatc cgccgcccgt ccacacccgc   180
cgccagctca ccatggatga tgatatcgcc gcgctcgtcg tcgacaacgg ctccggcatg   240
tgcaaggccg gcttcgcggg cgacgatgcc ccccgggccg tcttcccctc catcgtgggg   300
cgccccaggc accagggcgt gatggtgggc atgggtcaga aggattccta tgtgggcgac   360
gaggcccaga gcaagagagg catcctcacc ctgaagtacc catcgagca cggcatcgtc    420
accaactggg acgacatgga aaaatctgg caccacacct tctacaatga gctgcgtgtg    480
gctcccgagg agcaccccgt gctgctgacc gaggcccccc tgaaccccaa ggccaaccgc   540
gagaagatga cccagatcat gtttgagacc ttcaacaccc cagccatgta cgttgctatc   600
caggctgtgc tatccctgta cgcctctggc cgtaccactg gcatcgtgat ggactccggt   660
gacgggcta cccacactgt gcccatctac gaggggtatg ccctccccca tgccatcctg   720
cgtctggacc tggctggccg ggacctgact gactacctca tgaagatcct caccgagcgc   780
ggctacagct tcaccaccac ggccgagcgg gaaatcgtgc gtgacattaa ggagaagctg   840
tgctacgtcg ccctggactt cgagcaagag atggccacgg ctgcttccag ctcctccctg   900
gagaagagct acgagctgcc tgacggccag gtcatcacca ttggcaatga gcggttccgc   960
tgccctgagg cactcttcca gccttccttc ctgggcatgg agtcctgtgg catccacgaa  1020
actaccttca actccatcat gaagtgtgac gtggacatcc gcaaagacct gtacgccaac  1080
acagtgctgt ctggcggcac caccatgtac cctggcattg ccgacaggat gcagaaggag  1140
atcactgccc tggcacccag cacaatgaag atcaagatca ttgctcctcc tgagcgcaag  1200
tactccgtgt ggatcggcgg ctccatcctg gcctcgctgt ccaccttcca gcagatgtgg  1260
```

```
atcagcaagc aggagtatga cgagtccggc ccctccatcg tccaccgcaa atgcttctag    1320
gcggactatg acttagttgc gttacaccct ttcttgacaa acctaacttt gcgcagaaaa    1380
caagatgaga ttggcatggc tttatttgtt tttttgttt tgttttggtt ttttttttttt   1440 ttttggcttg actcaggatt taaaaactgg aacggtgaag gtgacagcag tcggttggag    1500
cgagcatccc ccaaagttca caatgtggcc gaggactttg attgcacatt gttgtttttt    1560
taatagtcat tccaaatatg agatgcgttg ttacaggaag tcccttgcca tcctaaaagc    1620
caccccactt ctctctaagg agaatggccc agtcctctcc caagtccaca caggggaggt    1680
gatagcattg ctttcgtgta aattatgtaa tgcaaaattt ttttaatctt cgccttaata    1740
cttttttatt ttgttttatt ttgaatgatg agccttcgtg ccccccttc ccctttttt     1800 gtcccccaac ttgagatgta tgaaggcttt tggtctccct gggagtgggt ggaggcagcc    1860
agggcttacc tgtacactga cttgagacca gttgaataaa agtgcacacc ttaaaaatga    1920
ggaaaaaaaa aaaaaaaaaa                                                1940

<210> SEQ ID NO 57
<211> LENGTH: 1242
<212> TYPE: DNA
<213> ORGANISM: Artificial Sequence
<220> FEATURE:
<223> OTHER INFORMATION: GAPDH plasmid

<400> SEQUENCE: 57
gacagccgca tcttcttgtg cagtgccagc ctcgtcccgt agacaaaatg gtgaaggtcg      60
gtgtgaacgg atttggccgt attgggcgcc tggtcaccag ggctgccatt tgcagtggca    120
aagtggagat tgttgccatc aacgaccct tcattgacct caactacatg gtctacatgt     180
tccagtatga ctccactcac ggcaaattca acggcacagt caaggccgag aatgggaagc    240
ttgtcatcaa cggaaagccc atcaccatct tccaggagcg agaccccact aacatcaaat    300
ggggtgaggc cggtgctgag tatgtcgtgg agtctactgg tgtcttcacc accatggaga    360 aggccgggc ccacttgaag ggtggagcca acgggtcat catctccgcc ccttctgccg      420 atgccccat gtttgtgatg ggtgtgaacc acgagaaata tgacaactca ctcaagattg     480
tcagcaatgc atcctgcacc accaactgct tagccccct ggccaaggtc atccatgaca    540
actttggcat tgtggaaggg ctcatgacca cagtccatgc catcactgcc acccagaaga    600
ctgtggatgg cccctctgga aagctgtggc gtgatggccg tggggctgcc cagaacatca    660
tccctgcatc cactggtgct gccaaggctg tgggcaaggt catcccagag ctgaacggga    720
agctcactgg catggccttc cgtgttccta ccccaatgt gtccgtcgtg gatctgacgt     780
gccgcctgga gaaacctgcc aagtatgatg acatcaagaa ggtggtgaag caggcatctg    840
agggcccact gaagggcatc ttgggctaca ctgaggacca ggttgtctcc tgcgacttca    900
acagcaactc ccactcttcc accttcgatg ccggggctgg cattgctctc aatgacaact    960 tgtcaagct catttcctgg tatgacaatg aatacggcta cagcaacagg gtggtggacc    1020
tcatggccta catggcctcc aaggagtaag aaaccctgga ccaccaccc cagcaaggac    1080 actgagcaag agaggcccta tcccaactcg gcccccaaca ctgagcatct ccctcacaat    1140
ttccatccca gaccccata ataacaggag gggcctaggg agccctccct actctcttga    1200
ataccatcaa taaagttcgc tgcacccaaa aaaaaaaaa aa                        1242

<210> SEQ ID NO 58
```

<211> LENGTH: 1497
<212> TYPE: DNA
<213> ORGANISM: Artificial Sequence
<220> FEATURE:
<223> OTHER INFORMATION: ILB1 Plasmid

<400> SEQUENCE: 58

| | | | | | |
|---|---|---|---|---|---|
| accaacctct | tcgaggcaca | aggcacaaca | ggctgctctg | ggattctctt | cagccaatct | 60 |
| tcattgctca | agtgtctgaa | gcagccatgg | cagaagtacc | tgagctcgcc | agtgaaatga | 120 |
| tggcttatta | cagtggcaat | gaggatgact | tgttctttga | agctgatggc | cctaaacaga | 180 |
| tgaagtgctc | cttccaggac | ctggacctct | gccctctgga | tggcggcatc | cagctacgaa | 240 |
| tctccgacca | ccactacagc | aagggcttca | ggcaggccgc | gtcagttgtt | gtggccatgg | 300 |
| acaagctgag | gaagatgctg | gttccctgcc | cacagacctt | ccaggagaat | gacctgagca | 360 |
| ccttcttcc | cttcatcttt | gaagaagaac | ctatcttctt | cgacacatgg | gataacgagg | 420 |
| cttatgtgca | cgatgcacct | gtacgatcac | tgaactgcac | gctccgggac | tcacagcaaa | 480 |
| aaagcttggt | gatgtctggt | ccatatgaac | tgaaagctct | ccacctccag | ggacaggata | 540 |
| tggagcaaca | agtggtgttc | tccatgtcct | ttgtacaagg | agaagaaagt | aatgacaaaa | 600 |
| tacctgtggc | cttgggcctc | aaggaaaaga | atctgtacct | gtcctgcgtg | ttgaaagatg | 660 |
| ataagcccac | tctacagctg | gagagtgtag | atcccaaaaa | ttacccaaag | aagaagatgg | 720 |
| aaaagcgatt | tgtcttcaac | aagatagaaa | tcaataacaa | gctggaattt | gagtctgccc | 780 |
| agttccccaa | ctggtacatc | agcacctctc | aagcagaaaa | catgcccgtc | ttcctgggag | 840 |
| ggaccaaagg | cggccaggat | ataactgact | tcaccatgca | atttgtgtct | tcctaaagag | 900 |
| agctgtaccc | agagagtcct | gtgctgaatg | tggactcaat | ccctagggct | ggcagaaagg | 960 |
| gaacagaaag | gttttttgagt | acggctatag | cctggacttt | cctgttgtct | acaccaatgc | 1020 |
| ccaactgcct | gccttagggt | agtgctaaga | ggatctcctg | tccatcagcc | aggacagtca | 1080 |
| gctctctcct | ttcagggcca | atccccagcc | cttttgttga | gccaggcctc | tctcacctct | 1140 |
| cctactcact | taaagcccgc | ctgacagaaa | ccacggccac | atttggttct | aagaaaccct | 1200 |
| ctgtcattcg | ctcccacatt | ctgatgagca | accgcttccc | tatttatta | tttatttgtt | 1260 |
| tgtttgtttt | attcattggt | ctaatttatt | caaaggggc | aagaagtagc | agtgtctgta | 1320 |
| aaagagccta | gttttttaata | gctatggaat | caattcaatt | tggactggtg | tgctctcttt | 1380 |
| aaatcaagtc | ctttaattaa | gactgaaaat | atataagctc | agattattta | aatgggaata | 1440 |
| tttataaatg | agcaaatatc | atactgttca | atggttctga | aataaacttc | tctgaag | 1497 |

<210> SEQ ID NO 59
<211> LENGTH: 1707
<212> TYPE: DNA
<213> ORGANISM: Artificial Sequence
<220> FEATURE:
<223> OTHER INFORMATION: TUBA Plasmid

<400> SEQUENCE: 59

| | | | | | |
|---|---|---|---|---|---|
| aagtgaacaa | tgggcgccca | gctctaaaat | gacagcctgg | ttcaatgggg | tggaggagct | 60 |
| agggagggat | gagtgctttg | tgtgcttgga | attagatcct | tcaaatggat | cctttctgaa | 120 |
| tgcaaaactg | tacatctcta | actggattct | tatttacttc | accaggactc | ttcagctccc | 180 |
| tgcgcctttt | aacacatgca | catccagcaa | aagcagagga | gaacctggct | gtgattcaaa | 240 |
| gcgtgagtgc | atctccatcc | acgttggcca | ggctggtgtc | cagattggca | atgcctgctg | 300 |
| ggagctctac | tgcctggaac | acggcatcca | gcccgatggc | cagatgccaa | gtgacaagac | 360 |

```
cattggggga ggagatgatt ccttcaacac cttcttcagt gaaacgggtg ctggcaagca    420
tgtgccccgg gcagtgtttg tagacttgga acccacagtc attgatgaag ttcgcactgg    480
cacttaccgc cagctcttcc accctgagca actcatcaca ggcaaggaag atgctgccaa    540
taactatgcc cgagggcact acaccattgg caaggagatc attgacctcg tgttggaccg    600
aattcgcaag ctggctgacc agtgcaccgg tcttcagggc ttcttggttt ccacagctt    660 tggtggggga actggttctg ggttcacctc gctgctcatg aacgtctct cagttgatta    720 tggcaagaag tccaagctgg agttctccat ttacccggcg ccccaggttt ccacagctgt    780
agttgagccc tacaactcca tcctcaccac ccacaccacc ctggagcact ctgattgtgc    840
cttcatggta gacaatgagg ccatctatga catctgtcgt agaaacctcg atatcgagcg    900
cccaacctac actaaccta accgccttat tagccagatt gtgtcctcca tcactgcttc    960
cctgagattt gatggagccc tgaatgttga cctgacagaa ttccagacca acctggtgcc    1020 ctaccccgc atccacttcc ctctggccac atatgcccct gtcatctctg ctgagaaagc    1080
ctaccacgaa cagcttactg tagcagagat caccaatgct tgctttgagc cagccaacca    1140
gatggtgaaa tgtgaccctc gccatggtaa atacatggct tgctgcctgt tataccgtgg    1200
tgacgtggtt cccaaagatg tcaatgctgc cattgccacc atcaaaacca agcgtaccat    1260
ccagtttgtg gattggtgcc ccactggctt caaggttggc attaattacc agcctcccac    1320
tgtggtgcct ggcggagacc tggccaaggt acagagagct gtgtgcatgc tgagcaatac    1380
cacagctgtt gccgaggcct gggctcgcct ggaccacaag tttgacctga tgtatgccaa    1440
gcgtgccttt gttcactggt acgtgggtga ggggatggag gaaggcgagt tttcagaggc    1500
ccgtgaggac atggctgccc ttgagaagga ttatgaggag gttggagcag atagtgctga    1560
cggagaggat gagggtgaag agtattaacc tgtgtgctgt acttttacac tccttttgtct    1620 tggaactgtc ttattttgt tctgtaaatg tctattgccg taaattgtta ataaaattga    1680
agtttccatt ttaaatgtca aaaaaaa                                        1707
```

```
<210> SEQ ID NO 60
<211> LENGTH: 22
<212> TYPE: DNA
<213> ORGANISM: Artificial Sequence
<220> FEATURE:
<223> OTHER INFORMATION: GAPDH Fwd

<400> SEQUENCE: 60
caactacatg gtctacatgt tc                                              22

<210> SEQ ID NO 61
<211> LENGTH: 17
<212> TYPE: DNA
<213> ORGANISM: Artificial Sequence
<220> FEATURE:
<223> OTHER INFORMATION: GAPDH Rev

<400> SEQUENCE: 61
ctcgctcctg gaagatg                                                    17

<210> SEQ ID NO 62
<211> LENGTH: 21
<212> TYPE: DNA
<213> ORGANISM: Artificial Sequence
<220> FEATURE:
<223> OTHER INFORMATION: GAPDH Probe
```

```
<400> SEQUENCE: 62
cggcacagtc aaggccgaga a                                    21

<210> SEQ ID NO 63
<211> LENGTH: 15
<212> TYPE: DNA
<213> ORGANISM: Artificial Sequence
<220> FEATURE:
<223> OTHER INFORMATION: ACTB Fwd

<400> SEQUENCE: 63
cttcaccacc acggc                                           15

<210> SEQ ID NO 64
<211> LENGTH: 17
<212> TYPE: DNA
<213> ORGANISM: Artificial Sequence
<220> FEATURE:
<223> OTHER INFORMATION: ACTB Rev

<400> SEQUENCE: 64
ccatctcttg ctcgaag                                         17

<210> SEQ ID NO 65
<211> LENGTH: 26
<212> TYPE: DNA
<213> ORGANISM: Artificial Sequence
<220> FEATURE:
<223> OTHER INFORMATION: ACTB Probe

<400> SEQUENCE: 65
tcgtgcgtga cattaaggag aagctg                               26

<210> SEQ ID NO 66
<211> LENGTH: 17
<212> TYPE: DNA
<213> ORGANISM: Artificial Sequence
<220> FEATURE:
<223> OTHER INFORMATION: IL1-B Fwd

<400> SEQUENCE: 66
tgctccttcc aggacct                                         17

<210> SEQ ID NO 67
<211> LENGTH: 17
<212> TYPE: DNA
<213> ORGANISM: Artificial Sequence
<220> FEATURE:
<223> OTHER INFORMATION: IL1-B Rev

<400> SEQUENCE: 67
gtggtggtcg gagattc                                         17

<210> SEQ ID NO 68
<211> LENGTH: 21
<212> TYPE: DNA
<213> ORGANISM: Artificial Sequence
<220> FEATURE:
<223> OTHER INFORMATION: Il1-B Probe

<400> SEQUENCE: 68
ctctgccctc tggatggcgg c                                    21

<210> SEQ ID NO 69
<211> LENGTH: 16
```

-continued

```
<212> TYPE: DNA
<213> ORGANISM: Artificial Sequence
<220> FEATURE:
<223> OTHER INFORMATION: TUBA Fwd

<400> SEQUENCE: 69
tcgcaagctg gctgac                                                         16

<210> SEQ ID NO 70
<211> LENGTH: 20
<212> TYPE: DNA
<213> ORGANISM: Artificial Sequence
<220> FEATURE:
<223> OTHER INFORMATION: TUBA Rev

<400> SEQUENCE: 70
aggtgaaccc agaaccagtt                                                     20

<210> SEQ ID NO 71
<211> LENGTH: 22
<212> TYPE: DNA
<213> ORGANISM: Artificial Sequence
<220> FEATURE:
<223> OTHER INFORMATION: TUBA Probe

<400> SEQUENCE: 71
caccggtctt cagggcttct tg                                                  22

<210> SEQ ID NO 72
<211> LENGTH: 73
<212> TYPE: PRT
<213> ORGANISM: Artificial Sequence
<220> FEATURE:
<223> OTHER INFORMATION: 400-472 region of M501 and M503

<400> SEQUENCE: 72

Gln Ile Gly Lys Ser Ala Asn Phe Gly Leu Ile Tyr Gly Ile Ser Pro
1               5                   10                  15

Lys Gly Phe Ala Glu Tyr Cys Ile Ser Asn Gly Ile Asn Ile Thr Glu
            20                  25                  30

Glu Met Ala Ile Glu Ile Val Lys Lys Trp Lys Phe Tyr Arg Lys
        35                  40                  45

Ile Ala Glu Gln Gln Lys Lys Ala Tyr Glu Arg Phe Lys Tyr Ala Glu
    50                  55                  60

Phe Val Asp Asn Glu Thr Trp Leu Asn
65                  70

<210> SEQ ID NO 73
<211> LENGTH: 2628
<212> TYPE: DNA
<213> ORGANISM: Artificial Sequence
<220> FEATURE:
<223> OTHER INFORMATION: M601

<400> SEQUENCE: 73
atgcgtggta tgcttccact gtttgaaccg aaaggccgtg tgctgctggt tgatggccac       60
catctggcct atcgtacctt ccatgcgctg aaaggcctga cgaccagccg cggcgaaccg      120
gtgcaggcgg tgtatggctt tgcgaaaagc ctgctgaaag cgctgaaaga agatggcgat      180
gcggttattg tggtgtttga tgcgaaagcg ccgagctttc gtcatgaagc gtatggcggc      240
tataaagcgg tcgtgcgcc gaccccggaa gattttccgc gtcagctggc cctgattaaa      300
gaactggtgg atctgctggg cctggcgcgt ctggaagtgc cgggctatga agcggatgat      360
```

```
gtgctggcca gcctggccaa aaaagcggaa aaagaaggct acgaagttcg tattctgacc      420
gccgataaag acctgtatca gctgctgtct gatcgtattc atgtgctgca tcctgagggt      480
tatctgatta ccccggcgtg gctgtgggaa aaatatggcc tgcgtccgga tcagtgggcg      540
gattatcgtg cgctgaccgg cgatgaaagc gataacctgc cgggcgtgaa aggcattggc      600
gaaaaaaccg cgcgtaaact gctggaagaa tggggcagcc tggaagcgct gctgaaaaac      660
ctggatcgtc tgaaaccggc gattcgtgaa aagatcttag cgcacatgga tgatctgaaa      720
ctgagctggg atctggccaa agtgcgtacc gatctgccgc tggaagtgga ttttgcgaaa      780
cgtcgtgaac cggatcgtga acgtctgcgt gcgtttctgg aacgtctgga atttggcagc      840
ctgctgcatg aatttggcct gctggaaagc ggtggcggcg ttctggcgg tggtggcagc      900 aatacccccga accgattct gaaaccgcag agcaaagcac tggttgaacc tgttctgtgt      960
gatagcattg atgaaattcc ggcaaaatac aatgaacctg tgtattttga tctggaaacc     1020
gatgaagatc gtccggttct ggcaagcatt tatcagccgc attttgaacg taaagtgtat     1080
tgtctgaatc tgctgcgtga aaaactggca cgttttaaag aatggctgct gaaatttagc     1140
gaaattcgtg gttggggctt agatttcgat ctgcgtgttc tgggttatac ctatgaacag     1200
ctgcgcaaca aaaaaatcgt tgacgtccag ctggccatta agtgcagca ttatgaacgc      1260 tttaaacaag gtggcaccaa aggtgaaggt tttcgtctgg atgatgttgc acgtgatctg     1320
ctgggtattg aatatccgat gaacaaaacg aaaatccgca ccaccttcaa gtataacatg     1380
tatagcagct tttcgtacga gcaactgctg tatgcaagcc tggatgcata tattccgcat     1440
ctgctgtacg aacgtctgag cagcgatacc ctgaatagcc tggtttatca gattgatcaa     1500
gaggttcaga aagtggtgat tgaaaccagc cagcatggta tgccggttaa actgaaagca     1560
ctggaagaag aaattcatcg tctgacccag ctgcgtagcg aaatgcagaa acaaattccg     1620
tttaactata atagcccgaa acagaccgcc aaattctttg tgttaatag cagcagcaaa     1680 gatgttctga tggatctggc actgcgtggt aatgaagttc ccaaaaaagt tctggaagca     1740
cgccagattg aaaaaagtct ggcattcgcc aaagatctgt atgatatcgc caaaaaaaac     1800
ggtggtcgca tctatggtaa ctttttttacc accaccgcac cgagcggtcg tatgagctgt     1860
agcaatatta acctgcagaa cattccgcgt cgtctgcgtc cgtttattgg ttttgaaacc     1920
gaggacaaaa aactgatcac cgcagatttt ccgcagattg aactgcgtct ggcaggcgtt     1980
atgtggaatg aacctgaatt tctgaaagcc tttcgtgatg gcattgatct gcacaaactg     2040
accgcaagta ttctgttcga taaaaagatt aacgaagtga gcaaagagga acgccagatc     2100
ggtaaaagcg caaatttttgg tctgattat ggtatcagcc cgaaaggttt tgccgaatat     2160
tgtattagca acggcattaa catcaccgaa gaaatgcaa tcgagatcgt gaaaaatgg      2220 aagaagttct atcgcaaaat cgccgaacag catcagctgg catatgaacg tttcaaatat     2280
gccgaattcg tggataatga aacctggctg aatcgtccgt atcgtgcttg caaaccgcaa     2340
gccctgctta actatcagat tcaaggtagc ggtgcagaac tgttcaaaaa agcaattgtt     2400
ctgctgaaag aagccaaacc ggatctgaaa attgtgaatc tggttcacga tgaaattgtg     2460
gtggaaacca gtaccgaaga agcagaagat attgcactgc tggtgaaaca aaagatggaa     2520
gaggcatggg attattgcct ggaaaaagca aagaatttg caataacgt ggccgacatt      2580 aaactggaag ttgaaaaacc gaatattagc agcgtgtggg aaaaagaa                  2628

<210> SEQ ID NO 74
```

```
<211> LENGTH: 876
<212> TYPE: PRT
<213> ORGANISM: Artificial Sequence
<220> FEATURE:
<223> OTHER INFORMATION: M601

<400> SEQUENCE: 74
```

| | | | | | | | | | | | | | | |
|---|---|---|---|---|---|---|---|---|---|---|---|---|---|---|
| Met | Arg | Gly | Met | Leu | Pro | Leu | Phe | Glu | Pro | Lys | Gly | Arg | Val | Leu | Leu |
| 1 | | | | 5 | | | | | 10 | | | | | 15 | |

| Val | Asp | Gly | His | His | Leu | Ala | Tyr | Arg | Thr | Phe | His | Ala | Leu | Lys | Gly |
|---|---|---|---|---|---|---|---|---|---|---|---|---|---|---|---|
| | | | 20 | | | | | 25 | | | | | 30 | | |

| Leu | Thr | Thr | Ser | Arg | Gly | Glu | Pro | Val | Gln | Ala | Val | Tyr | Gly | Phe | Ala |
|---|---|---|---|---|---|---|---|---|---|---|---|---|---|---|---|
| | | | 35 | | | | | 40 | | | | | 45 | | |

| Lys | Ser | Leu | Leu | Lys | Ala | Leu | Lys | Glu | Asp | Gly | Asp | Ala | Val | Ile | Val |
|---|---|---|---|---|---|---|---|---|---|---|---|---|---|---|---|
| | 50 | | | | | 55 | | | | | 60 | | | | |

| Val | Phe | Asp | Ala | Lys | Ala | Pro | Ser | Phe | Arg | His | Glu | Ala | Tyr | Gly | Gly |
|---|---|---|---|---|---|---|---|---|---|---|---|---|---|---|---|
| 65 | | | | | 70 | | | | | 75 | | | | | 80 |

| Tyr | Lys | Ala | Gly | Arg | Ala | Pro | Thr | Pro | Glu | Asp | Phe | Pro | Arg | Gln | Leu |
|---|---|---|---|---|---|---|---|---|---|---|---|---|---|---|---|
| | | | | 85 | | | | | 90 | | | | | 95 | |

| Ala | Leu | Ile | Lys | Glu | Leu | Val | Asp | Leu | Leu | Gly | Leu | Ala | Arg | Leu | Glu |
|---|---|---|---|---|---|---|---|---|---|---|---|---|---|---|---|
| | | | 100 | | | | | 105 | | | | | 110 | | |

| Val | Pro | Gly | Tyr | Glu | Ala | Asp | Asp | Val | Leu | Ala | Ser | Leu | Ala | Lys | Lys |
|---|---|---|---|---|---|---|---|---|---|---|---|---|---|---|---|
| | | | 115 | | | | | 120 | | | | | 125 | | |

| Ala | Glu | Lys | Glu | Gly | Tyr | Glu | Val | Arg | Ile | Leu | Thr | Ala | Asp | Lys | Asp |
|---|---|---|---|---|---|---|---|---|---|---|---|---|---|---|---|
| | 130 | | | | | 135 | | | | | 140 | | | | |

| Leu | Tyr | Gln | Leu | Leu | Ser | Asp | Arg | Ile | His | Val | Leu | His | Pro | Glu | Gly |
|---|---|---|---|---|---|---|---|---|---|---|---|---|---|---|---|
| 145 | | | | | 150 | | | | | 155 | | | | | 160 |

| Tyr | Leu | Ile | Thr | Pro | Ala | Trp | Leu | Trp | Glu | Lys | Tyr | Gly | Leu | Arg | Pro |
|---|---|---|---|---|---|---|---|---|---|---|---|---|---|---|---|
| | | | | 165 | | | | | 170 | | | | | 175 | |

| Asp | Gln | Trp | Ala | Asp | Tyr | Arg | Ala | Leu | Thr | Gly | Asp | Glu | Ser | Asp | Asn |
|---|---|---|---|---|---|---|---|---|---|---|---|---|---|---|---|
| | | | 180 | | | | | 185 | | | | | 190 | | |

| Leu | Pro | Gly | Val | Lys | Gly | Ile | Gly | Glu | Lys | Thr | Ala | Arg | Lys | Leu | Leu |
|---|---|---|---|---|---|---|---|---|---|---|---|---|---|---|---|
| | | | 195 | | | | | 200 | | | | | 205 | | |

| Glu | Glu | Trp | Gly | Ser | Leu | Glu | Ala | Leu | Leu | Lys | Asn | Leu | Asp | Arg | Leu |
|---|---|---|---|---|---|---|---|---|---|---|---|---|---|---|---|
| | 210 | | | | | 215 | | | | | 220 | | | | |

| Lys | Pro | Ala | Ile | Arg | Glu | Lys | Ile | Leu | Ala | His | Met | Asp | Asp | Leu | Lys |
|---|---|---|---|---|---|---|---|---|---|---|---|---|---|---|---|
| 225 | | | | | 230 | | | | | 235 | | | | | 240 |

| Leu | Ser | Trp | Asp | Leu | Ala | Lys | Val | Arg | Thr | Asp | Leu | Pro | Leu | Glu | Val |
|---|---|---|---|---|---|---|---|---|---|---|---|---|---|---|---|
| | | | | 245 | | | | | 250 | | | | | 255 | |

| Asp | Phe | Ala | Lys | Arg | Arg | Glu | Pro | Asp | Arg | Glu | Arg | Leu | Arg | Ala | Phe |
|---|---|---|---|---|---|---|---|---|---|---|---|---|---|---|---|
| | | | 260 | | | | | 265 | | | | | 270 | | |

| Leu | Glu | Arg | Leu | Glu | Phe | Gly | Ser | Leu | Leu | His | Glu | Phe | Gly | Leu | Leu |
|---|---|---|---|---|---|---|---|---|---|---|---|---|---|---|---|
| | | | 275 | | | | | 280 | | | | | 285 | | |

| Glu | Ser | Gly | Gly | Gly | Ser | Gly | Gly | Gly | Ser | Asn | Thr | Pro | Lys |
|---|---|---|---|---|---|---|---|---|---|---|---|---|---|
| | 290 | | | | | 295 | | | | | 300 | | |

| Pro | Ile | Leu | Lys | Pro | Gln | Ser | Lys | Ala | Leu | Val | Glu | Pro | Val | Leu | Cys |
|---|---|---|---|---|---|---|---|---|---|---|---|---|---|---|---|
| 305 | | | | | 310 | | | | | 315 | | | | | 320 |

| Asp | Ser | Ile | Asp | Glu | Ile | Pro | Ala | Lys | Tyr | Asn | Glu | Pro | Val | Tyr | Phe |
|---|---|---|---|---|---|---|---|---|---|---|---|---|---|---|---|
| | | | | 325 | | | | | 330 | | | | | 335 | |

| Asp | Leu | Glu | Thr | Asp | Glu | Asp | Arg | Pro | Val | Leu | Ala | Ser | Ile | Tyr | Gln |
|---|---|---|---|---|---|---|---|---|---|---|---|---|---|---|---|
| | | | 340 | | | | | 345 | | | | | 350 | | |

| Pro | His | Phe | Glu | Arg | Lys | Val | Tyr | Cys | Leu | Asn | Leu | Arg | Glu | Lys |
|---|---|---|---|---|---|---|---|---|---|---|---|---|---|---|
| | | | 355 | | | | | 360 | | | | | 365 | |

| Leu | Ala | Arg | Phe | Lys | Glu | Trp | Leu | Leu | Lys | Phe | Ser | Glu | Ile | Arg | Gly |
|---|---|---|---|---|---|---|---|---|---|---|---|---|---|---|---|
| | 370 | | | | | 375 | | | | | 380 | | | | |

-continued

```
Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
            405                 410                 415

His Tyr Glu Arg Phe Lys Gln Gly Gly Thr Lys Gly Glu Gly Phe Arg
        420                 425                 430

Leu Asp Asp Val Ala Arg Asp Leu Leu Gly Ile Glu Tyr Pro Met Asn
    435                 440                 445

Lys Thr Lys Ile Arg Thr Thr Phe Lys Tyr Asn Met Tyr Ser Ser Phe
450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
                485                 490                 495

Gln Ile Asp Gln Glu Val Gln Lys Val Val Ile Glu Thr Ser Gln His
            500                 505                 510

Gly Met Pro Val Lys Leu Lys Ala Leu Glu Glu Ile His Arg Leu
        515                 520                 525

Thr Gln Leu Arg Ser Glu Met Gln Lys Gln Ile Pro Phe Asn Tyr Asn
530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
            580                 585                 590

Leu Tyr Asp Ile Ala Lys Lys Asn Gly Gly Arg Ile Tyr Gly Asn Phe
        595                 600                 605

Phe Thr Thr Thr Ala Pro Ser Gly Arg Met Ser Cys Ser Asn Ile Asn
    610                 615                 620

Leu Gln Asn Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
            660                 665                 670

Asp Gly Ile Asp Leu His Lys Leu Thr Ala Ser Ile Leu Phe Asp Lys
        675                 680                 685

Lys Ile Asn Glu Val Ser Lys Glu Glu Arg Gln Ile Gly Lys Ser Ala
    690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735

Val Lys Lys Trp Lys Lys Phe Tyr Arg Lys Ile Ala Glu Gln His Gln
            740                 745                 750

Leu Ala Tyr Glu Arg Phe Lys Tyr Ala Glu Phe Val Asp Asn Glu Thr
        755                 760                 765

Trp Leu Asn Arg Pro Tyr Arg Ala Cys Lys Pro Gln Ala Leu Leu Asn
    770                 775                 780

Tyr Gln Ile Gln Gly Ser Gly Ala Glu Leu Phe Lys Lys Ala Ile Val
785                 790                 795                 800
```

| Leu | Leu | Lys | Glu | Ala | Lys | Pro | Asp | Leu | Lys | Ile | Val | Asn | Leu | Val | His |
|---|---|---|---|---|---|---|---|---|---|---|---|---|---|---|---|
| | | | | 805 | | | | 810 | | | | | 815 | | |

| Asp | Glu | Ile | Val | Val | Glu | Thr | Ser | Thr | Glu | Glu | Ala | Glu | Asp | Ile | Ala |
|---|---|---|---|---|---|---|---|---|---|---|---|---|---|---|---|
| | | | 820 | | | | | 825 | | | | | 830 | | |

| Leu | Leu | Val | Lys | Gln | Lys | Met | Glu | Glu | Ala | Trp | Asp | Tyr | Cys | Leu | Glu |
|---|---|---|---|---|---|---|---|---|---|---|---|---|---|---|---|
| | | | 835 | | | | | 840 | | | | | 845 | | |

| Lys | Ala | Lys | Glu | Phe | Gly | Asn | Asn | Val | Ala | Asp | Ile | Lys | Leu | Glu | Val |
|---|---|---|---|---|---|---|---|---|---|---|---|---|---|---|---|
| | 850 | | | | | 855 | | | | | 860 | | | | |

| Glu | Lys | Pro | Asn | Ile | Ser | Ser | Val | Trp | Glu | Lys | Glu |
|---|---|---|---|---|---|---|---|---|---|---|---|
| 865 | | | | | 870 | | | | 875 | | |

<210> SEQ ID NO 75
<211> LENGTH: 2628
<212> TYPE: DNA
<213> ORGANISM: Artificial Sequence
<220> FEATURE:
<223> OTHER INFORMATION: M602

<400> SEQUENCE: 75

```
atgcgtggta tgcttccact gtttgaaccg aaaggccgtg tgctgctggt tgatggccac      60
catctggcct atcgtacctt ccatgcgctg aaaggcctga cgaccagccg cggcgaaccg     120
gtgcaggcgg tgtatgactt tgcgaaaagc ctgctgaaag cgctgaaaga gatggcgat     180
gcggttattg tggtgtttga tgcgaaagcg ccgagctttc gtcatgaagc gtatggcggc     240
tataaagcgg tcgtgcgcc gaccccggaa gattttccgc gtcagctggc cctgattaaa     300
gaactggtgg atctgctggg cctggcgcgt ctggaagtgc cgggctatga gcggatgat     360
gtgctggcca gcctggccaa aaaagcggaa aagaaggct acgaagttcg tattctgacc     420
gccgataaag acctgtatca gctgctgtct gatcgtattc atgtgctgca tcctgagggt     480
tatctgatta ccccggcgtg gctgtgggaa aaatatggcc tgcgtccgga tcagtgggcg     540
gattatcgtg cgctgaccgg cgatgaaagc gataacctgc cgggcgtgaa aggcattggc     600
gaaaaaaccg cgcgtaaact gctggaagaa tgggggcagcc tggaagcgct gctgaaaaac     660
ctggatcgtc tgaaaccggc gattcgtgaa aagatcttag cgcacatgga tgatctgaaa     720
ctgagctggg atctggccaa agtgcgtacc gatctgccgc tggaagtgga ttttgcgaaa     780
cgtcgtgaac cggatcgtga acgtctgcgt gcgtttctgg aacgtctgga atttggcagc     840
ctgctgcatg aatttggcct gctggaaagc ggtggcggcg ttctggcgg tggtggcagc     900
aatacccga accgattct gaaaccgcag agcaaagcac tggttgaacc tgttctgtgt     960
gatagcattg atgaaattcc ggcaaaatac aatgaacctg tgtattttga tctggaaacc    1020
gatgaagatc gtccggttct ggcaagcatt atcagccgc attttgaacg taaagtgtat    1080
tgtctgaatc tgctgcgtga aaaactggca cgttttaaag aatggctgct gaaatttagc    1140
gaaattcgtg gttgggcctt agatttcgat ctgcgtgttc tgggttatac ctatgaacag    1200
ctgcgcaaca aaaaaatcgt tgacgtccag ctggccatta agtgcagca ttatgaacgc    1260
tttaaacaag gtggcaccaa aggtgaaggt tttcgtctgg atgatgttgc acgtgatctg    1320
ctgggtattg aatatccgat gaacaaaacg aaaatccgca ccaccttcaa gtataacatg    1380
tatagcagct tttcgtacga gcaactgctg tatgcaagcc tggatgcata tattccgcat    1440
ctgctgtacg aacgtctgag cagcgatacc ctgaatagcc tggtttatca gattgatcaa    1500
gaggttcaga aagtggtgat tgaaaccagc cagcatggta tgccggttaa actgaaagca    1560
ctggaagaag aaattcatcg tctgaccccag ctgcgtagcg aaatgcagaa acaaattccg    1620
```

```
tttaactata atagcccgaa acagaccgcc aaattctttg gtgttaatag cagcagcaaa    1680
gatgttctga tggatctggc actgcgtggt aatgaagttg ccaaaaaagt tctggaagca    1740
cgccagattg aaaaaagtct ggcattcgcc aaagatctgt atgatatcgc caaaaaaaac    1800
ggtggtcgca tctatggtaa cttttttacc accaccgcac cgagcggtcg tatgagctgt    1860
agcaatatta acctgcagaa cattccgcgt cgtctgcgtc cgtttattgg ttttgaaacc    1920
gaggacaaaa aactgatcac cgcagatttt ccgcagattg aactgcgtct ggcaggcgtt    1980
atgtggaatg aacctgaatt tctgaaagcc tttcgtgatg gcattgatct gcacaaactg    2040
accgcaagta ttctgttcga taaaaagatt aacgaagtga gcaaagagga acgccagatc    2100
ggtaaaagcg caaattttgg tctgatttat ggtatcagcc cgaaaggttt tgccgaatat    2160
tgtattagca acggcattaa catcaccgaa gaaatggcaa tcgagatcgt gaaaaaatgg    2220
aagaagttct atcgcaaaat cgccgaacag catcagctgg catatgaacg tttcaaatat    2280
gccgaattcg tggataatga aacctggctg aatcgtccgt atcgtgcttg caaaccgcaa    2340
gccctgctta actatcagat tcaaggtagc ggtgcagaac tgttcaaaaa agcaattgtt    2400
ctgctgaaag aagccaaacc ggatctgaaa attgtgaatc tggttcacga tgaaattgtg    2460
gtggaaacca gtaccgaaga agcagaagat attgcactgc tggtgaaaca aaagatggaa    2520
gaggcatggg attattgcct ggaaaaagca aaagaatttg gcaataacgt ggccgacatt    2580 aaactgaag ttgaaaaacc gaatattagc agcgtgtggg aaaaagaa                  2628
```

<210> SEQ ID NO 76
<211> LENGTH: 876
<212> TYPE: PRT
<213> ORGANISM: Artificial Sequence
<220> FEATURE:
<223> OTHER INFORMATION: M602

<400> SEQUENCE: 76

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190
```

-continued

```
Leu Pro Gly Val Lys Gly Ile Gly Glu Lys Thr Ala Arg Lys Leu Leu
            195                 200                 205
Glu Glu Trp Gly Ser Leu Glu Ala Leu Leu Lys Asn Leu Asp Arg Leu
    210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
            260                 265                 270
Leu Glu Arg Leu Glu Phe Gly Ser Leu Leu His Glu Phe Gly Leu Leu
    275                 280                 285
Glu Ser Gly Gly Gly Ser Gly Gly Gly Ser Asn Thr Pro Lys
    290                 295                 300
Pro Ile Leu Lys Pro Gln Ser Lys Ala Leu Val Glu Pro Val Leu Cys
305                 310                 315                 320
Asp Ser Ile Asp Glu Ile Pro Ala Lys Tyr Asn Glu Pro Val Tyr Phe
                325                 330                 335
Asp Leu Glu Thr Asp Glu Asp Arg Pro Val Leu Ala Ser Ile Tyr Gln
            340                 345                 350
Pro His Phe Glu Arg Lys Val Tyr Cys Leu Asn Leu Arg Glu Lys
    355                 360                 365
Leu Ala Arg Phe Lys Glu Trp Leu Leu Lys Phe Ser Glu Ile Arg Gly
    370                 375                 380
Trp Gly Leu Asp Phe Asp Leu Arg Val Leu Gly Tyr Thr Tyr Glu Gln
385                 390                 395                 400
Leu Arg Asn Lys Lys Ile Val Asp Val Gln Leu Ala Ile Lys Val Gln
                405                 410                 415
His Tyr Glu Arg Phe Lys Gln Gly Gly Thr Lys Gly Glu Gly Phe Arg
            420                 425                 430
Leu Asp Asp Val Ala Arg Asp Leu Leu Gly Ile Glu Tyr Pro Met Asn
    435                 440                 445
Lys Thr Lys Ile Arg Thr Thr Phe Lys Tyr Asn Met Tyr Ser Ser Phe
    450                 455                 460
Ser Tyr Glu Gln Leu Leu Tyr Ala Ser Leu Asp Ala Tyr Ile Pro His
465                 470                 475                 480
Leu Leu Tyr Glu Arg Leu Ser Ser Asp Thr Leu Asn Ser Leu Val Tyr
                485                 490                 495
Gln Ile Asp Gln Glu Val Gln Lys Val Ile Glu Thr Ser Gln His
            500                 505                 510
Gly Met Pro Val Lys Leu Lys Ala Leu Glu Glu Ile His Arg Leu
    515                 520                 525
Thr Gln Leu Arg Ser Glu Met Gln Lys Gln Ile Pro Phe Asn Tyr Asn
    530                 535                 540
Ser Pro Lys Gln Thr Ala Lys Phe Phe Gly Val Asn Ser Ser Lys
545                 550                 555                 560
Asp Val Leu Met Asp Leu Ala Leu Arg Gly Asn Glu Val Ala Lys Lys
                565                 570                 575
Val Leu Glu Ala Arg Gln Ile Glu Lys Ser Leu Ala Phe Ala Lys Asp
            580                 585                 590
Leu Tyr Asp Ile Ala Lys Lys Asn Gly Gly Arg Ile Tyr Gly Asn Phe
    595                 600                 605
```

Phe Thr Thr Ala Pro Ser Gly Arg Met Ser Cys Ser Asn Ile Asn
610                 615                 620

Leu Gln Asn Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
                645                 650                 655

Leu Ala Gly Val Met Trp Asn Glu Pro Glu Phe Leu Lys Ala Phe Arg
                660                 665                 670

Asp Gly Ile Asp Leu His Lys Leu Thr Ala Ser Ile Leu Phe Asp Lys
                675                 680                 685

Lys Ile Asn Glu Val Ser Lys Glu Glu Arg Gln Ile Gly Lys Ser Ala
690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735

Val Lys Lys Trp Lys Lys Phe Tyr Arg Lys Ile Ala Glu Gln His Gln
                740                 745                 750

Leu Ala Tyr Glu Arg Phe Lys Tyr Ala Glu Phe Val Asp Asn Glu Thr
                755                 760                 765

Trp Leu Asn Arg Pro Tyr Arg Ala Cys Lys Pro Gln Ala Leu Leu Asn
770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Glu Ala Glu Asp Ile Ala
                820                 825                 830

Leu Leu Val Lys Gln Lys Met Glu Glu Ala Trp Asp Tyr Cys Leu Glu
                835                 840                 845

Lys Ala Lys Glu Phe Gly Asn Asn Val Ala Asp Ile Lys Leu Glu Val
                850                 855                 860

Glu Lys Pro Asn Ile Ser Ser Val Trp Glu Lys Glu
865                 870                 875

<210> SEQ ID NO 77
<211> LENGTH: 2628
<212> TYPE: DNA
<213> ORGANISM: Artificial Sequence
<220> FEATURE:
<223> OTHER INFORMATION: M603

<400> SEQUENCE: 77
atgcgtggta tgcttccact gtttgaaccg aaaggccgtg tgctgctggt tgatggccac      60
catctggcct atcgtacctt ccatgcgctg aaaggcctga cgaccagccg cggcgaaccg     120
gtgcaggcgg tgtatggctt tgcgaaaagc ctgctgaaag cgctgaaaga agatggcgat     180
gcggttattg tggtgtttga tgcgaaagcg ccgagctttc gtcatgaagc gtatggcggc     240
tataaagcgg tcgtgcgcc gacccoggaa gattttccgc gtcagctggc cctgattaaa     300
gaactggtgg atctgctggg cctggcgcgt ctggaagtgc cgggctatga gcggatgat     360 gtgctggcca gctggccaa aaaagcggaa aagaaggct acgaagttcg tattctgacc      420
gccgataaag acctgtatca gctgctgtct gatcgtattc atgtgctgca tcctgagggt     480
tatctgatta ccccggcgtg gctgtgggaa aaatatggcc tgcgtccgga tcagtgggcg     540

| | |
|---|---|
| gattatcgtg cgctgaccgg cgatgaaagc gataacctgc cgggcgtgaa aggcattggc | 600 |
| gaaaaaccg cgcgtaaact gctggaagaa tggggcagcc tggaagcgct gctgaaaaac | 660 |
| ctggatcgtc tgaaaccggc gattcgtgaa aagatcttag cgcacatgga tgatctgaaa | 720 |
| ctgagctggg atctggccaa agtgcgtacc gatctgccgc tggaagtgga ttttgcgaaa | 780 |
| cgtcgtgaac cggatcgtga acgtctgcgt gcgtttctgg aacgtctgga atttggcagc | 840 |
| ctgctgcatg aatttggcct gctggaaagc ggtggcggcg ttctggcgg tggtggcagc | 900 |
| aataccccga accgattct gaaaccgcag agcaaagcac tggttgaacc tgttctgtgt | 960 |
| gatagcattg atgaaattcc ggcaaaatac aatgaacctg tgtattttga tctggaaacc | 1020 |
| gatgaagatc gtccggttct ggcaagcatt tatcagccgc attttgaacg taaagtgtat | 1080 |
| tgtctgaatc tgctgcgtga aaaactggca cgttttaaag aatggctgct gaaatttagc | 1140 |
| gaaattcgtg gttgggcctt agatttcgat ctgcgtgttc tgggttatac ctatgaacag | 1200 |
| ctgcgcaaca aaaaaatcgt tgacgtccag ctggccatta aagtgcagca ttatgaacgc | 1260 |
| tttaaacaag gtggcaccaa aggtgaaggt ttcgtctgg atgatgttgc acgtgatctg | 1320 |
| ctgggtattg aatatccgat gaacaaaacg aaaatccgca ccaccttcaa gtataacatg | 1380 |
| tatagcagct tttcgtacga gcaactgctg tatgcaagcc tggatgcata tattccgcat | 1440 |
| ctgctgtacg aacgtctgag cagcgatacc ctgaatagcc tggtttatca gattgatcaa | 1500 |
| gaggttcaga agtggtgat tgaaaccagc cagcatggta tgccggttaa actgaaagca | 1560 |
| ctggaagaag aaattcatcg tctgacccag ctgcgtagcg aaatgcagaa acaaattccg | 1620 |
| tttaactata atagcccgaa acagaccgcc aaattctttg gtgttaatag cagcagcaaa | 1680 |
| gatgttctga tggatctggc actgcgtggt aatgaagttg ccaaaaaagt tctggaagca | 1740 |
| cgccagattg aaaaaagtct ggcattcgcc aaagatctgt atgatatcgc caaaaaaaac | 1800 |
| ggtggtcgca tctatggtaa cttttttacc accaccgcac cgagcggtcg tatgagctgt | 1860 |
| agcgatatta acctgcagaa cattccgcgt cgtctgcgtc cgtttattgg ttttgaaacc | 1920 |
| gaggacaaaa aactgatcac cgcagatttt ccgcagattg aactgcgtct ggcaggcgtt | 1980 |
| atgtggaatg aacctgaatt tctgaaagcc tttcgtgatg cattgatct gcacaaactg | 2040 |
| accgcaagta ttctgttcga taaaaagatt aacgaagtga gcaaagagga acgccagatc | 2100 |
| ggtaaaagcg caaattttgg tctgatttat ggtatcagcc cgaaaggttt tgccgaatat | 2160 |
| tgtattagca acggcattaa catcaccgaa gaaatggcaa tcgagatcgt gaaaaaatgg | 2220 |
| aagaagttct atcgcaaaat cgccgaacag cagaagaagg catatgaacg tttcaaatat | 2280 |
| gccgaattcg tggataatga aacctggctg aatcgtccgt atcgtgcatg gaaaccgcaa | 2340 |
| gatctgctga actatcagat tcaaggtagc ggtgcagaac tgttcaaaaa agcaattgtt | 2400 |
| ctgctgaaag aagccaaacc ggatctgaaa attgtgaatc tggttcacga tgaaattgtg | 2460 |
| gtggaaacca gtaccgaaga agcagaagat attgcactgc tggtgaaaca aaagatggaa | 2520 |
| gaggcatggg attattgcct ggaaaaagca aagaatttg gcaataacgt ggccgacatt | 2580 |
| aaactggaag ttgaaaaacc gaatattagc agcgtgtggg aaaaagaa | 2628 |

<210> SEQ ID NO 78
<211> LENGTH: 876
<212> TYPE: PRT
<213> ORGANISM: Artificial Sequence
<220> FEATURE:
<223> OTHER INFORMATION: M603

<400> SEQUENCE: 78

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
                100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Gly Gly Gly Ser Gly Gly Gly Ser Asn Thr Pro Lys
290                 295                 300

Pro Ile Leu Lys Pro Gln Ser Lys Ala Leu Val Glu Pro Val Leu Cys
305                 310                 315                 320

Asp Ser Ile Asp Glu Ile Pro Ala Lys Tyr Asn Glu Pro Val Tyr Phe
                325                 330                 335

Asp Leu Glu Thr Asp Glu Asp Arg Pro Val Leu Ala Ser Ile Tyr Gln
            340                 345                 350

Pro His Phe Glu Arg Lys Val Tyr Cys Leu Asn Leu Leu Arg Glu Lys
            355                 360                 365

Leu Ala Arg Phe Lys Glu Trp Leu Leu Lys Phe Ser Glu Ile Arg Gly
        370                 375                 380

Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
                405                 410                 415
```

His Tyr Glu Arg Phe Lys Gln Gly Gly Thr Lys Gly Glu Gly Phe Arg
                420                 425                 430

Leu Asp Asp Val Ala Arg Asp Leu Leu Gly Ile Glu Tyr Pro Met Asn
            435                 440                 445

Lys Thr Lys Ile Arg Thr Thr Phe Lys Tyr Asn Met Tyr Ser Ser Phe
        450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
                485                 490                 495

Gln Ile Asp Gln Glu Val Gln Lys Val Val Ile Glu Thr Ser Gln His
            500                 505                 510

Gly Met Pro Val Lys Leu Lys Ala Leu Glu Glu Ile His Arg Leu
        515                 520                 525

Thr Gln Leu Arg Ser Glu Met Gln Lys Gln Ile Pro Phe Asn Tyr Asn
        530                 535                 540

Ser Pro Lys Gln Thr Ala Lys Phe Phe Gly Val Asn Ser Ser Lys
545                 550                 555                 560

Asp Val Leu Met Asp Leu Ala Leu Arg Gly Asn Glu Val Ala Lys Lys
                565                 570                 575

Val Leu Glu Ala Arg Gln Ile Glu Lys Ser Leu Ala Phe Ala Lys Asp
            580                 585                 590

Leu Tyr Asp Ile Ala Lys Lys Asn Gly Gly Arg Ile Tyr Gly Asn Phe
        595                 600                 605

Phe Thr Thr Thr Ala Pro Ser Gly Arg Met Ser Cys Ser Asp Ile Asn
610                 615                 620

Leu Gln Asn Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
            645                 650                 655

Leu Ala Gly Val Met Trp Asn Glu Pro Glu Phe Leu Lys Ala Phe Arg
        660                 665                 670

Asp Gly Ile Asp Leu His Lys Leu Thr Ala Ser Ile Leu Phe Asp Lys
        675                 680                 685

Lys Ile Asn Glu Val Ser Lys Glu Glu Arg Gln Ile Gly Lys Ser Ala
        690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
            725                 730                 735

Val Lys Lys Trp Lys Lys Phe Tyr Arg Lys Ile Ala Glu Gln Gln Lys
        740                 745                 750

Lys Ala Tyr Glu Arg Phe Lys Tyr Ala Glu Phe Val Asp Asn Glu Thr
        755                 760                 765

Trp Leu Asn Arg Pro Tyr Arg Ala Trp Lys Pro Gln Asp Leu Leu Asn
        770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Glu Ala Glu Asp Ile Ala
            820                 825                 830

Leu Leu Val Lys Gln Lys Met Glu Glu Ala Trp Asp Tyr Cys Leu Glu 835                 840                 845
Lys Ala Lys Glu Phe Gly Asn Asn Val Ala Asp Ile Lys Leu Glu Val
            850                 855                 860

Glu Lys Pro Asn Ile Ser Ser Val Trp Glu Lys Glu
865                 870                 875

<210> SEQ ID NO 79
<211> LENGTH: 2628
<212> TYPE: DNA
<213> ORGANISM: Artificial Sequence
<220> FEATURE:
<223> OTHER INFORMATION: M604

<400> SEQUENCE: 79

| | | | |
|---|---|---|---|
| atgcgtggta tgcttccact gtttgaaccg aaaggccgtg tgctgctggt tgatggccac | 60 |
| catctggcct atcgtacctt ccatgcgctg aaaggcctga cgaccagccg cggcgaaccg | 120 |
| gtgcaggcgg tgtatgactt tgcgaaaagc ctgctgaaag cgctgaaaga agatggcgat | 180 |
| gcggttattg tggtgtttga tgcgaaagcg ccgagctttc gtcatgaagc gtatggcggc | 240 |
| tataaagcgg tcgtgcgcc gaccccggaa gattttccgc gtcagctggc cctgattaaa | 300 |
| gaactggtgg atctgctggg cctggcgcgt ctggaagtgc cgggctatga gcggatgat | 360 |
| gtgctggcca gcctggccaa aaaagcggaa aagaaggct acgaagttcg tattctgacc | 420 |
| gccgataaag acctgtatca gctgctgtct gatcgtattc atgtgctgca tcctgagggt | 480 |
| tatctgatta ccccggcgtg gctgtgggaa aaatatggcc tgcgtccgga tcagtgggcg | 540 |
| gattatcgtg cgctgaccgg cgatgaaagc gataacctgc cggcgtgaa aggcattggc | 600 |
| gaaaaaaccg cgcgtaaact gctggaagaa tggggcagcc tggaagcgct gctgaaaaac | 660 |
| ctggatcgtc tgaaaccggc gattcgtgaa agatcttag cgcacatgga tgatctgaaa | 720 |
| ctgagctggg atctggccaa agtgcgtacc gatctgccgc tggaagtgga ttttgcgaaa | 780 |
| cgtcgtgaac cggatcgtga acgtctgcgt gcgtttctgg aacgtctgga atttggcagc | 840 |
| ctgctgcatg aatttggcct gctggaaagc ggtggcggcg ttctggcgg tggtggcagc | 900 |
| aatacccga aaccgattct gaaaccgcag agcaaagcac tggttgaacc tgttctgtgt | 960 |
| gatagcattg atgaaattcc ggcaaaatac aatgaacctg tgtattttga tctggaaacc | 1020 |
| gatgaagatc gtccggttct ggcaagcatt tatcagccgc atttgaacg taaagtgtat | 1080 |
| tgtctgaatc tgctgcgtga aaaactggca cgttttaaag aatggctgct gaaatttagc | 1140 |
| gaaattcgtg gttggggctt agatttcgat ctgcgtgttc tgggttatac ctatgaacag | 1200 |
| ctgcgcaaca aaaaatcgt tgacgtccag ctggccatta agtgcagca ttatgaacgc | 1260 |
| tttaaacaag gtggcaccaa aggtgaaggt tttcgtctgg atgatgttgc acgtgatctg | 1320 |
| ctgggtattg aatatccgat gaacaaaacg aaaatccgca ccaccttcaa gtataacatg | 1380 |
| tatagcagct tttcgtacga gcaactgctg tatgcaagcc tggatgcata tattccgcat | 1440 |
| ctgctgtacg aacgtctgag cagcgatacc ctgaatagcc tggtttatca gattgatcaa | 1500 |
| gaggttcaga agtggtgat tgaaaccagc cagcatggta tgccggttaa actgaaagca | 1560 |
| ctggaagaag aaattcatcg tctgacccag ctgcgtagcg aaatgcagaa acaaattccg | 1620 |
| tttaactata atagcccgaa acagaccgcc aaattctttg tgttaatag cagcagcaaa | 1680 |
| gatgttctga tggatctggc actgcgtggt aatgaagttg ccaaaaaagt tctggaagca | 1740 |
| cgccagattg aaaaaagtct ggcattcgcc aaagatctgt atgatatcgc caaaaaaac | 1800 |
| ggtggtcgca tctatggtaa cttttttacc accaccgcac cgagcggtcg tatgagctgt | 1860 |

-continued

```
agcgatatta acctgcagaa cattccgcgt cgtctgcgtc cgtttattgg ttttgaaacc    1920
gaggacaaaa aactgatcac cgcagatttt ccgcagattg aactgcgtct ggcaggcgtt    1980
atgtggaatg aacctgaatt tctgaaagcc tttcgtgatg cattgatct gcacaaactg     2040
accgcaagta ttctgttcga taaaaagatt aacgaagtga gcaaagagga acgccagatc    2100
ggtaaaagcg caaattttgg tctgatttat ggtatcagcc cgaaaggttt tgccgaatat    2160
tgtattagca acggcattaa catcaccgaa gaaatggcaa tcgagatcgt gaaaaaatgg    2220
aagaagttct atcgcaaaat cgccgaacag cagaagaagg catatgaacg tttcaaatat    2280
gccgaattcg tggataatga aacctggctg aatcgtccgt atcgtgcatg gaaaccgcaa    2340
gatctgctga actatcagat tcaaggtagc ggtgcagaac tgttcaaaaa agcaattgtt    2400
ctgctgaaag aagccaaacc ggatctgaaa attgtgaatc tggttcacga tgaaattgtg    2460
gtggaaacca gtaccgaaga agcagaagat attgcactgc tggtgaaaca aaagatggaa    2520
gaggcatggg attattgcct ggaaaaagca aaagaatttg caataacgt ggccgacatt      2580
aaactggaag ttgaaaaacc gaatattagc agcgtgtggg aaaaagaa                  2628
```

<210> SEQ ID NO 80
<211> LENGTH: 876
<212> TYPE: PRT
<213> ORGANISM: Artificial Sequence
<220> FEATURE:
<223> OTHER INFORMATION: M604

<400> SEQUENCE: 80

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Asp Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220
```

```
Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
        260                 265                 270

Leu Glu Arg Leu Glu Phe Gly Ser Leu Leu His Glu Phe Gly Leu Leu
    275                 280                 285

Glu Ser Gly Gly Gly Gly Ser Gly Gly Gly Gly Ser Asn Thr Pro Lys
290                 295                 300

Pro Ile Leu Lys Pro Gln Ser Lys Ala Leu Val Glu Pro Val Leu Cys
305                 310                 315                 320

Asp Ser Ile Asp Glu Ile Pro Ala Lys Tyr Asn Glu Pro Val Tyr Phe
            325                 330                 335

Asp Leu Glu Thr Asp Glu Asp Arg Pro Val Leu Ala Ser Ile Tyr Gln
            340                 345                 350

Pro His Phe Glu Arg Lys Val Tyr Cys Leu Asn Leu Leu Arg Glu Lys
        355                 360                 365

Leu Ala Arg Phe Lys Glu Trp Leu Leu Lys Phe Ser Glu Ile Arg Gly
370                 375                 380

Trp Gly Leu Asp Phe Asp Leu Arg Val Leu Gly Tyr Thr Tyr Glu Gln
385                 390                 395                 400

Leu Arg Asn Lys Lys Ile Val Asp Val Gln Leu Ala Ile Lys Val Gln
                405                 410                 415

His Tyr Glu Arg Phe Lys Gln Gly Gly Thr Lys Gly Glu Gly Phe Arg
        420                 425                 430

Leu Asp Asp Val Ala Arg Asp Leu Leu Gly Ile Glu Tyr Pro Met Asn
    435                 440                 445

Lys Thr Lys Ile Arg Thr Thr Phe Lys Tyr Asn Met Tyr Ser Ser Phe
450                 455                 460

Ser Tyr Glu Gln Leu Leu Tyr Ala Ser Leu Asp Ala Tyr Ile Pro His
465                 470                 475                 480

Leu Leu Tyr Glu Arg Leu Ser Ser Asp Thr Leu Asn Ser Leu Val Tyr
            485                 490                 495

Gln Ile Asp Gln Glu Val Gln Lys Val Val Ile Glu Thr Ser Gln His
        500                 505                 510

Gly Met Pro Val Lys Leu Lys Ala Leu Glu Glu Glu Ile His Arg Leu
    515                 520                 525

Thr Gln Leu Arg Ser Glu Met Gln Lys Gln Ile Pro Phe Asn Tyr Asn
530                 535                 540

Ser Pro Lys Gln Thr Ala Lys Phe Phe Gly Val Asn Ser Ser Ser Lys
545                 550                 555                 560

Asp Val Leu Met Asp Leu Ala Leu Arg Gly Asn Glu Val Ala Lys Lys
            565                 570                 575

Val Leu Glu Ala Arg Gln Ile Glu Lys Ser Leu Ala Phe Ala Lys Asp
        580                 585                 590

Leu Tyr Asp Ile Ala Lys Lys Asn Gly Gly Arg Ile Tyr Gly Asn Phe
    595                 600                 605

Phe Thr Thr Thr Ala Pro Ser Gly Arg Met Ser Cys Ser Asp Ile Asn
610                 615                 620

Leu Gln Asn Ile Pro Arg Arg Leu Arg Pro Phe Ile Gly Phe Glu Thr
625                 630                 635                 640

Glu Asp Lys Lys Leu Ile Thr Ala Asp Phe Pro Gln Ile Glu Leu Arg
```

```
                645                 650                 655
Leu Ala Gly Val Met Trp Asn Glu Pro Glu Phe Leu Lys Ala Phe Arg
            660                 665                 670

Asp Gly Ile Asp Leu His Lys Leu Thr Ala Ser Ile Leu Phe Asp Lys
        675                 680                 685

Lys Ile Asn Glu Val Ser Lys Glu Arg Gln Ile Gly Lys Ser Ala
    690                 695                 700

Asn Phe Gly Leu Ile Tyr Gly Ile Ser Pro Lys Gly Phe Ala Glu Tyr
705                 710                 715                 720

Cys Ile Ser Asn Gly Ile Asn Ile Thr Glu Glu Met Ala Ile Glu Ile
                725                 730                 735

Val Lys Lys Trp Lys Lys Phe Tyr Arg Lys Ile Ala Glu Gln Gln Lys
            740                 745                 750

Lys Ala Tyr Glu Arg Phe Lys Tyr Ala Glu Phe Val Asp Asn Glu Thr
        755                 760                 765

Trp Leu Asn Arg Pro Tyr Arg Ala Trp Lys Pro Gln Asp Leu Leu Asn
    770                 775                 780

Tyr Gln Ile Gln Gly Ser Gly Ala Glu Leu Phe Lys Lys Ala Ile Val
785                 790                 795                 800

Leu Leu Lys Glu Ala Lys Pro Asp Leu Lys Ile Val Asn Leu Val His
                805                 810                 815

Asp Glu Ile Val Val Glu Thr Ser Thr Glu Glu Ala Glu Asp Ile Ala
            820                 825                 830

Leu Leu Val Lys Gln Lys Met Glu Glu Ala Trp Asp Tyr Cys Leu Glu
        835                 840                 845

Lys Ala Lys Glu Phe Gly Asn Asn Val Ala Asp Ile Lys Leu Glu Val
    850                 855                 860

Glu Lys Pro Asn Ile Ser Ser Val Trp Glu Lys Glu
865                 870                 875

<210> SEQ ID NO 81
<211> LENGTH: 112
<212> TYPE: RNA
<213> ORGANISM: Artificial Sequence
<220> FEATURE:
<223> OTHER INFORMATION: template RNA

<400> SEQUENCE: 81
rurargrgrc rgrurcrgrg rurgrarcra rararcrgrg rcrcrargrc rgrururgru      60
rurgrurcru rcrurcrurg rururcrura rgrcrurura rurcrgrgru rc             112

<210> SEQ ID NO 82
<211> LENGTH: 74
<212> TYPE: DNA
<213> ORGANISM: Artificial Sequence
<220> FEATURE:
<223> OTHER INFORMATION: DNA primer strand containing a 3'-terminal
      nucleotide match

<400> SEQUENCE: 82
gccgatatcg gacaacggcc gaactgggaa ggcgagactg accgaccgat aagctagaac      60
agagagacaa caac                                                       74

<210> SEQ ID NO 83
<211> LENGTH: 75
<212> TYPE: DNA
<213> ORGANISM: Artificial Sequence
<220> FEATURE:
```

```
<223> OTHER INFORMATION: DNA primer strand containing a 3'-terminal dC
      mismatch

<400> SEQUENCE: 83
gccgatatcg gacaacggcc gaactgggaa ggcgagactg accgaccgat aagctagaac    60
agagagacaa caacc                                                    75

<210> SEQ ID NO 84
<211> LENGTH: 75
<212> TYPE: DNA
<213> ORGANISM: Artificial Sequence
<220> FEATURE:
<223> OTHER INFORMATION: DNA primer strand containing a 3'-terminal dA
      mismatch

<400> SEQUENCE: 84
gccgatatcg gacaacggcc gaactgggaa ggcgagactg accgaccgat aagctagaac    60
agagagacaa caaca                                                    75

<210> SEQ ID NO 85
<211> LENGTH: 75
<212> TYPE: DNA
<213> ORGANISM: Artificial Sequence
<220> FEATURE:
<223> OTHER INFORMATION: DNA primer strand containing a 3'-terminal dT
      mismatch

<400> SEQUENCE: 85
gccgatatcg gacaacggcc gaactgggaa ggcgagactg accgaccgat aagctagaac    60
agagagacaa caact                                                    75

<210> SEQ ID NO 86
<211> LENGTH: 25
<212> TYPE: DNA
<213> ORGANISM: Artificial Sequence
<220> FEATURE:
<223> OTHER INFORMATION: forward primer

<400> SEQUENCE: 86
ggacaacggc cgaactggga aggcg                                         25

<210> SEQ ID NO 87
<211> LENGTH: 25
<212> TYPE: DNA
<213> ORGANISM: Artificial Sequence
<220> FEATURE:
<223> OTHER INFORMATION: reverse primer

<400> SEQUENCE: 87
taggcgtcgg tgacaaacgg ccagc                                         25

<210> SEQ ID NO 88
<211> LENGTH: 30
<212> TYPE: DNA
<213> ORGANISM: Artificial Sequence
<220> FEATURE:
<223> OTHER INFORMATION: probe
<220> FEATURE:
```

```
<221> NAME/KEY: misc_structure
<222> LOCATION: 5'
<223> OTHER INFORMATION: /note="5' FAM, ZEN quencher between base 9 and
      10, 3'-Iowa Black"

<400> SEQUENCE: 88
actgaccgac cgataagcta gaacagagag                                          30
```

US 11,807,667 B2

THERMOSTABLE VIRAL REVERSE TRANSCRIPTASE

CROSS-REFERENCE TO RELATED APPLICATIONS

This is a U.S. National Phase Application of International Application No. PCT/IB2019/053537, filed Apr. 30, 2019, which claims priority to and the benefit of the filing date of U.S. Provisional Patent Application No. 62/665,560, filed May 2, 2018, European Patent Application No. 18173195.1, filed May 18, 2018, U.S. Provisional Patent Application No. 62/790,483, filed Jan. 10, 2019 and to U.S. Provisional Patent Application No. 62/835,521, filed Apr. 18, 2019, which are incorporated herein by reference in their entireties.

FIELD OF THE INVENTION

The present invention provides novel engineered polypeptides that support both reverse transcription and DNA amplification, in manganese-independent reactions. The present invention also provides methods for amplifying template nucleic acids using such polypeptides. This invention addresses deficiencies in the current state of the art in nucleic acid amplification-based detection of template nucleic acids, especially RNA targets, including deficiencies in detection sensitivity, specificity, enzyme stability, inhibitor tolerance and time to result compared with manganese-dependent thermostable reverse transcriptases and two-enzyme solutions.

BACKGROUND OF THE INVENTION

Sensitive amplification of specific RNA sequences enables molecular detection and quantification of targets including, e.g., transcription products that may indicate disease states like cancer, RNA viruses that may be associated with infectious diseases, and rRNA that can allow extremely sensitive detection of prokaryotic and eukaryotic cells. Improvements in detection are highly valued in the areas of diagnostics, human and veterinary health care, agriculture, food safety, environmental monitoring and scientific research.

In the current state of the art, primary tools for detecting and quantifying RNA are variants of reverse transcription polymerase chain reaction (RT-PCR), such as quantitative RT-PCR (RT-qPCR) or real-time RT-PCR. Other variants of RT-PCR include digital RT-PCR (dRT-PCR) or digital droplet RT-PCR (ddRT-PCR). These methods are all improved by this invention. The present invention is also useful in related methods of amplifying RNA without high temperature thermal cycling, such as loop-mediated isothermal amplification (LAMP), helicase dependent amplification (HDA) and recombinase polymerase amplification (RPA).

These methods are further facilitated by enzymatic functionalities that allow fluorescent detection of the amplification products.

In the current state of the art, RT-PCR typically uses two distinct enzymes, a thermolabile reverse transcriptase (RT), often a murine Moloney leukemia virus (MMLV) RT derivative, that synthesizes complementary DNA (cDNA) based on an RNA template, and a distinct DNA polymerase, commonly Taq polymerase, for amplification of the DNA product. Commonly, a third enzymatic activity, 5'→3' exonuclease activity, inherent in Taq DNA polymerase, facilitates fluorescent detection by amplification-dependent hydrolysis and dequenching of a fluorescent DNA probe.

Several RT-PCR mixes, including some One Step RT-PCR kits, are currently provided, e.g., by QIAGEN (e.g., QIAGEN OneStep RT-PCR Kit) and Thermo Fisher Scientific (e.g., TaqMan® Fast Virus 1-Step Master Mix). All of these are two enzyme systems using derivatives of a retroviral RT and Taq DNA polymerase.

The reliance on multiple enzymes for these different steps has an inherent consequence that reaction conditions are necessarily a compromise between those optimal for the respective enzymes. This has a negative impact on sensitivity, specificity, time-to-result, ease of use, stability in storage and other key characteristics. Further, the presence of both enzymes in a single tube may lead to direct interference between the RT and the polymerase thereby limiting the sensitivity of RNA detection (Sellner, 1992).

In addition to retroviral RTs, *Bacillus* PolA enzymes often have moderately thermostable inherent RT activity, but, like the retroviral RTs, none has been thermostable enough for PCR. Reported attempts to increase thermostability of retroviral RTs by mutagenesis and in vitro evolution have been unsuccessful in providing adequate thermostability to allow single enzyme RT-PCR. Some inherently thermostable DNA polymerases, e.g. Tth polymerase and Hawk Z05 (Roche), can be induced to function as reverse transcriptases by modifying the buffer to include manganese rather than the typical magnesium. Other variants of thermostable DNA polymerases, e.g. those of *Thermus* (U.S. Pat. No. 5,455,170), Thermatoga and other thermophiles, have been modified by mutagenesis and directed evolution to use RNA templates. Intron encoded RTs from various thermophilic bacteria been explored for their potential use in single enzyme RT-PCR.

Single enzyme magnesium-dependent RT-PCR was enabled by PyroPhage® DNA polymerase (Lucigen). A 588 amino acid sequence was submitted as GenBank Acc. No. AFN99405.1 with the patent filings, i.e. U.S. Pat. No. 8,093,030 and related patents, and presumptively comprises the PyroPhage DNA polymerase. However, it was later found that this sequence contains an error from amino acid positions 450 to 463. This error was corrected by submission of GenBank Acc. No. AGL03984, a 611 amino acid open reading frame, the carboxyterminal 588 amino acids of which comprise the correct PyroPhage polymerase sequence. The corrected 588 amino acid sequence, including mutation E51A intentionally incorporated into the PyroPhage DNA polymerase to eliminate exonuclease activity, is shown in SEQ ID NO:15. This enzyme has both thermostable reverse transcriptase and DNA polymerase activities. This enzyme, as described in patents (e.g., U.S. Pat. No. 8,093,030) and literature (Schoenfeld et al., 2013; Moser et al., 2012), proved difficult to manufacture consistently, did not have sufficient RT activity, and was not competitive with the two enzyme systems with regard to ease of use, sensitivity, versatility in target RNAs, time-to-result, functionality in detection using probes or overall reliability.

Overall, none of these alternative thermostable reverse transcriptase/polymerase enzymes has been sufficiently effective in RT-PCR and the two enzyme mixes continue to be the state of the art for the great majority of practitioners.

The polypeptides of the present invention improve on the previously described molecule of SEQ ID NO:15 in that the amino acid sequence of the polymerase domain is altered by truncation of the N terminus of this sequence, such as elimination of eleven amino terminal amino acids from the N terminus of the protein sequence.

Previous attempts to use this molecule failed due the inability to produce a consistent product and for that reason failed to address the needs for reliable RT-PCR. The inventors of the present invention discovered that this variability was likely due to different levels of an internal translational initiation intrinsic to the host cells that eliminates those eleven amino acids from the amino terminus during normal enzyme expression. The result is a highly variable, heterogeneous mix of full-length and truncated product. It was also found that this truncated product, and not the full-length product, actually provides the RT activity and that truncating the gene to produce the smaller product results in a homogeneous product with higher overall RT activity.

Further, the primary sequence of this enzyme was improved by in vitro evolution. The improvements originated from a screening of published variants of differing levels of divergence (Schoenfeld et al., 2013) for polymerases with biochemical profiles that could potentially enhance functionality. The selected variants (Parent 1, 2, 3; SEQ ID NOs: 18-20) showed either high RT activity or thermostability.

The inventors of the present invention found that by combining specific regions derived from the different parent molecules, i.e., a region comprising the amino acid sequence of SEQ ID NO:16 and a region comprising an amino acid sequence selected from the group consisting of SEQ ID NO:17 and SEQ ID NO:72 or amino acid sequences at least 90%, preferably at least 95%, more preferably at least 98% identical thereto, polypeptides having improved combinations of properties regarding both RT activity and thermostability could be generated. Advantageously, the polypeptides of the invention may be applied in single enzyme RT-PCR reactions or in related reactions, such as amplifying RNA without high temperature thermal cycling, in conjunction with a second DNA polymerase, e.g. Taq DNA polymerase, for two enzyme RT PCR systems or preparative uses such as cDNA synthesis for cloning or for RNA sequence analysis.

In addition to analytic applications, there exist preparative uses for cDNA synthesis and RT-PCR, including cDNA cloning, preparation of templates for sequence determination of messenger and noncoding RNA, and other similar applications known in the art. In contrast to analytic methods, preservation of the integrity of the nucleotide sequence is critical for these preparative applications and there is an unmet need for improved accuracy of cDNA synthesis, both in conjunction with and independent of subsequent PCR typical of RT-PCR reactions. Substantial improvements in the accuracy of synthesis and amplification using DNA templates have been realized over the past three decades since the introduction of the first thermostable proofreading DNA polymerases, e.g. Lundberg K S, et al. (1991) Gene. 108(1):1-6; however, no such proofreading reverse transcriptase has been available for high accuracy, high efficiency synthesis using RNA templates.

A native proofreading activity is inherent to the parent molecules used to derive the enzymes of this invention. To limit complications from this secondary activity such as degradation of primers, this proofreading exonuclease activity was disabled by mutagenesis in versions of the enzyme of this invention that are intended for analytic uses. Since this activity is beneficial in preparative use, this proofreading function was reconstituted in the best mode RT constructs by reversion of the proofreading exonuclease domain to the wildtype sequence. These constructs represent the preferred embodiment for preparative use in of the invention in high fidelity RT-PCR.

SUMMARY OF THE INVENTION

In one aspect, the present invention relates to polypeptides comprising a polymerase domain comprising an amino acid sequence of SEQ ID NO:16 and an amino acid sequence selected from the group consisting of SEQ ID NO:17 and SEQ ID NO:72, or amino acid sequences at least 90%, preferably at least 95%, more preferably at least 98% identical thereto.

In some embodiments, the N-terminus of the polymerase domain corresponds to the sequence of positions 12-22 of the sequence of SEQ ID NO:15, or a sequence at least 90%, preferably at least 95%, more preferably at least 98% identical thereto. In some preferred embodiments, the N-terminus is an amino acid sequence of "MN($X_1$)PKPILKPQ($X_2$)KALVEPVLC($X_3$)SI($X_4$)EIPA" (SEQ ID NO:21); or variants thereof, wherein $X_1$=A or T; $X_2$=P or S; $X_3$=N or D; and $X_4$=N or D.

In certain embodiments, the polymerase domain comprises an amino acid sequence of SEQ ID NO:2, SEQ ID NO:4, SEQ ID NO:6, SEQ ID NO:8, SEQ ID NO:10, or SEQ ID NO:12, or an amino acid sequence at least 90%, preferably at least 95%, more preferably at least 98% identical thereto.

In other embodiments, the polypeptide further comprises an exonuclease domain connected to the polymerase domain, preferably via a linker.

In one embodiment, the polypeptide exhibits only reverse transcriptase and DNA polymerase activity. In another embodiment, the polypeptide also exhibits 5'→3' exonuclease activity.

One aspect of the present invention relates to compositions comprising a polypeptide of the invention. Another aspect of the present invention relates to vectors encoding the polypeptides of the invention. In another aspect, the present invention relates to transformed host cells comprising the vectors.

In another aspect, the present invention refers to methods for amplifying template nucleic acids comprising contacting the template nucleic acids with a polypeptide of the invention.

In one embodiment, the method is RT-PCR.

In certain embodiments, the method comprises a) generating cDNA using a polypeptide of the invention, and b) amplifying the generated cDNA using a polypeptide of the invention.

In some embodiments, the same polypeptide is applied for steps a) and b).

In other embodiments, the reverse transcription of step a) and the amplification of step b) are performed at isothermal conditions.

In another aspect, the present invention relates to kits comprising the polypeptide of the invention and a buffer.

In other embodiments, this invention provides a proofreading function coupled to high efficiency reverse transcription and inhibitor tolerance to enable high fidelity cDNA synthesis that enables high accuracy RT PCR.

Panel B. Endpoint pUC19 DNA PCR demonstrates that both lots of full length 3173 polymerase possess DNA polymerase activity and are capable of thermal cycling.

Panel C. Endpoint MS2 RNA RT-PCR demonstrates that only the partially purified full-length 3173 polymerase displays RT-PCR activity, whereas the extensively purified 3173 full-length polymerase does not allow product generation in RT-PCR.

Panel D. Real-time RT-qPCR demonstrates that the truncated 577 amino acid 3173 polymerase retains RT-PCR activity despite being extensively purified. In addition, the extensively purified M160 polymerase has lower Cq values on RNA templates, indicated a higher reverse transcriptase activity compared with 3173 polymerase.

FIG. 2: Motifs shared by the RT-PCR enhanced mutant enzymes.

Panel A. The RT-PCR enhanced mutants contained the region between 400 and 472 (SEQ ID NOs: 26-34) derived from Parent 2, i.e., a region comprising an amino acid sequence corresponding to SEQ ID NO:17 or SEQ ID NO:72 or amino acid sequences at least 90%, preferably at least 95% identical thereto.

Panel B. All the RT-PCR enhanced clones contained the region between 231 and 260 (SEQ ID NOs: 35-43), i.e., a region comprising the amino acid sequence corresponding to SEQ ID NO:16 or amino acid sequences at least 90%, preferably at least 95% identical thereto derived from Parent 1 or 3, which are almost indistinguishable in that region. Based on alignment to Taq Pol (not shown) this region probably includes the H helix.

Figure 3:
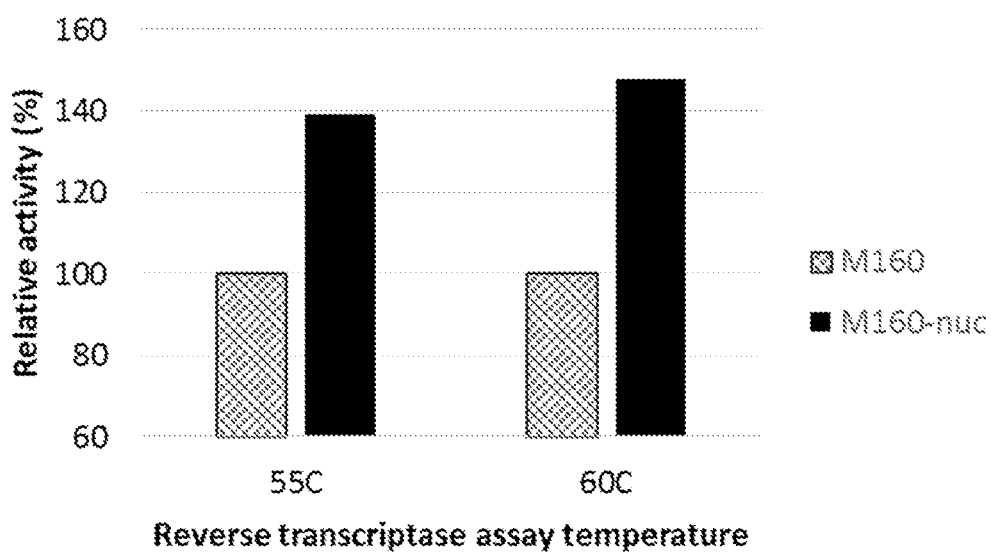

FIG. 3: Reverse transcriptase activity of M160 and M160-nuc at 55° C. and 60° C.

Figure 4:
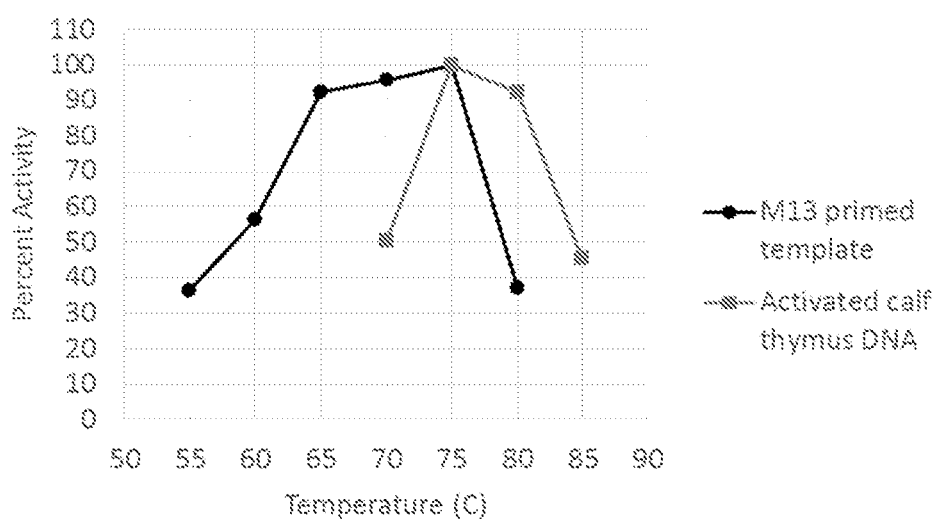

FIG. 4: Thermal activity profile of M160-nuc.

FIG. 5: Sensitivity and efficiency of detection of viral RNA.
Panel A. Detection by M160.
Panel B. Detection by M160-nuc.

Figure 6:
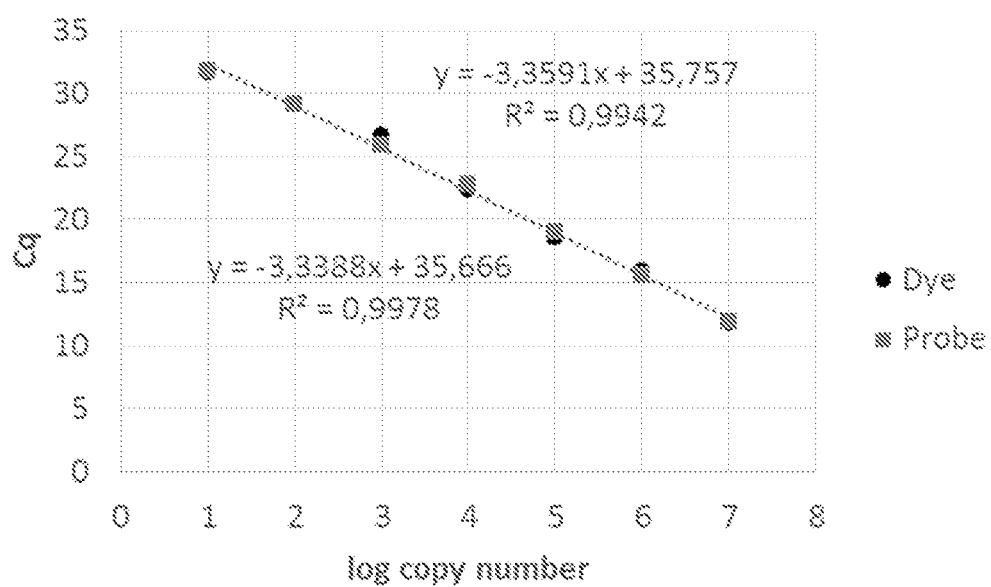

FIG. 6: M160-nuc compatibility with dye- and probe-based qPCR reaction chemistry.

FIG. 7: Comparison of M160-nuc with two-enzyme RT-PCR mix.
Panel A. Detection of a synthetic DNA target corresponding to MS2 RNA.
Panel B. Detection MS2 RNA target.

Figure 8:
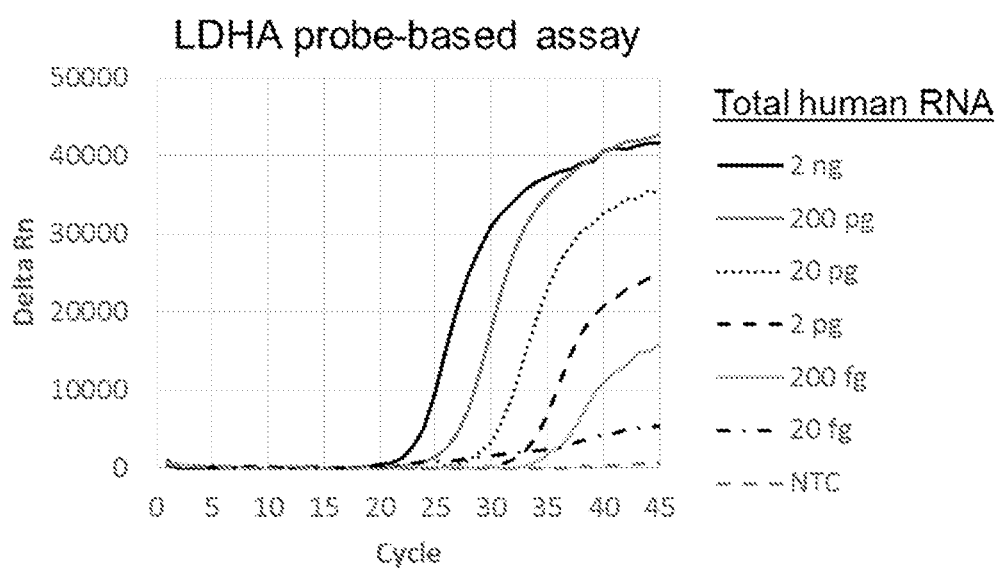

FIG. 8: Amplification of an mRNA transcript from total human RNA with M160-nuc.

Figure 9:
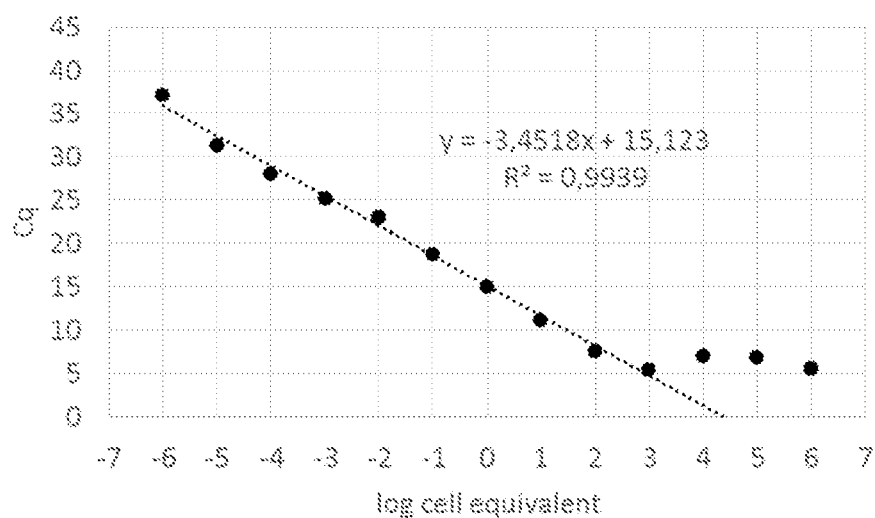

FIG. 9: Amplification of 16S rRNA directly from bacterial cell lysate with M160-nuc.

FIG. 10: Illustrates the binding affinity of engineered polymerases to primed-template DNA using an electrophoretic mobility shift assay.
Panel A. Shows the binding affinity of M160 polymerase.
Panel B. Illustrates the increased binding affinity of the M160-nuc polymerase.
Panel C. Illustrates the further increased binding affinity of the M502 mutant polymerase.

FIG. 11: Illustrates a comparison of the biochemical activity of the M160-nuc heparin resistant mutants with M160-nuc.
Panel A. DNA polymerase specific activity as measured using oligonucleotide-primed M13 DNA template.
Panel B. Reverse transcriptase activity as measured using an oligo(dT)$_{20}$-primed poly(A) template.

Figure 12:
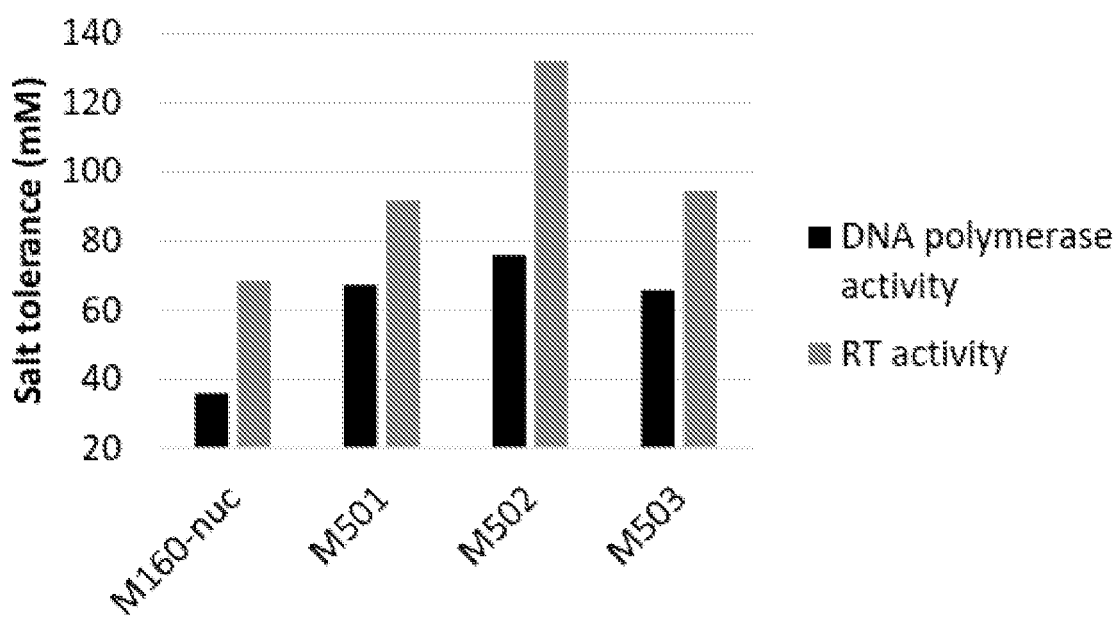

FIG. 12: Illustrates the increased salt tolerance of the M160-nuc heparin resistant mutants compared with M160-nuc by measuring DNA polymerase activity on an oligonucleotide-primed M13 DNA template and reverse transcriptase activity using an oligo(dT)$_{20}$-primed poly(A) template.

FIG. 13: Illustrates tolerance to the inhibitory effects of heparin on the detection of MS2 viral RNA using either M160-nuc, M501, M502, or M503 polymerase in one-step RT-qPCR reactions.
Panel A. Reaction buffer lacking human serum albumin.
Panel B. Reaction buffer including 1 mg/ml human serum albumin.

FIG. 14: Illustrates tolerance to the inhibitory effects of hematin on the detection of MS2 viral RNA using either M160-nuc, M501, M502, or M503 polymerase in one-step RT-qPCR reactions.
Panel A. Reaction buffer lacking human serum albumin.
Panel B. Reaction buffer including 1 mg/ml human serum albumin.

FIG. 15: Illustrates tolerance to the inhibitory effects of humic acid on the detection of MS2 viral RNA using either M160-nuc, M501, M502, or M503 polymerase in one-step RT-qPCR reactions.
Panel A. Reaction buffer lacking human serum albumin.
Panel B. Reaction buffer including 1 mg/ml human serum albumin.

FIG. 16: Illustrates tolerance to the inhibitory effects of hemoglobin on the detection of MS2 viral RNA using either M160-nuc, M501, M502, or M503 polymerase in one-step RT-qPCR reactions.
Panel A. Reaction buffer lacking human serum albumin.
Panel B. Reaction buffer including 1 mg/ml human serum albumin.

FIG. 17: Illustrates tolerance to the inhibitory effects of xylan on the detection of MS2 viral RNA using either M160-nuc, M501, M502, or M503 polymerase in one-step RT-qPCR reactions.
Panel A. Reaction buffer lacking human serum albumin.
Panel B. Reaction buffer including 1 mg/ml human serum albumin.

FIG. 18: Illustrates the detection sensitivity of the M160-nuc, M501, M502, or M503 polymerase in one-step RT-qPCR reactions.
Panel A. Detection of MS2 viral RNA using hydrolysis probe-based chemistry.
Panel B. Detection of MS2 viral RNA using Eva Green dye-based chemistry.
Panel C. Detecti4 on of LDHA mRNA from total human RNA using hydrolysis probe-based chemistry.

FIG. 19: Illustrates the improved detection of LDHA mRNA from total human RNA in probe-based one-step RT-qPCR reactions using mixtures of M503 and Taq polymerase.
Panel A. Shows the improvement in the fluorescent signal generated using enzyme mixtures containing Taq polymerase.
Panel B. Shows the improvement in Cq values using enzyme mixtures containing Taq polymerase.

Figure 20:
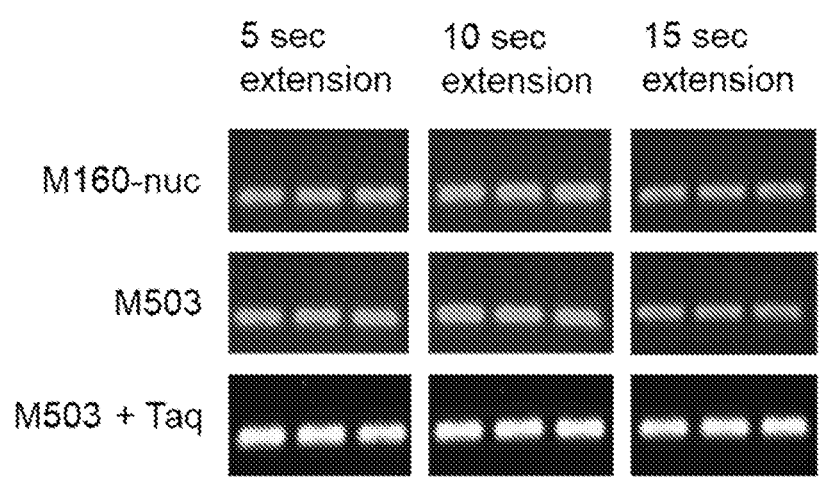

FIG. 20: Illustrates the extension speed of M160-nuc, M503, and a mixture of M503 and Taq polymerase using end-point PCR amplification of MS2 viral RNA.

FIG. 21: Illustrates the detection sensitivity of four target DNA sequences using a mixture of M503 and Taq polymerase in multiplex one-step qPCR reactions.
Panel A. Each of the four target DNA sequences was present in reactions at the same copy number.

Panel B. The ACTB, IL1B, and TUBA DNA sequences were present in all reactions at $10^8$ copies. The GAPDH DNA sequences were present in reactions at the indicated copy number.

Figure 22:
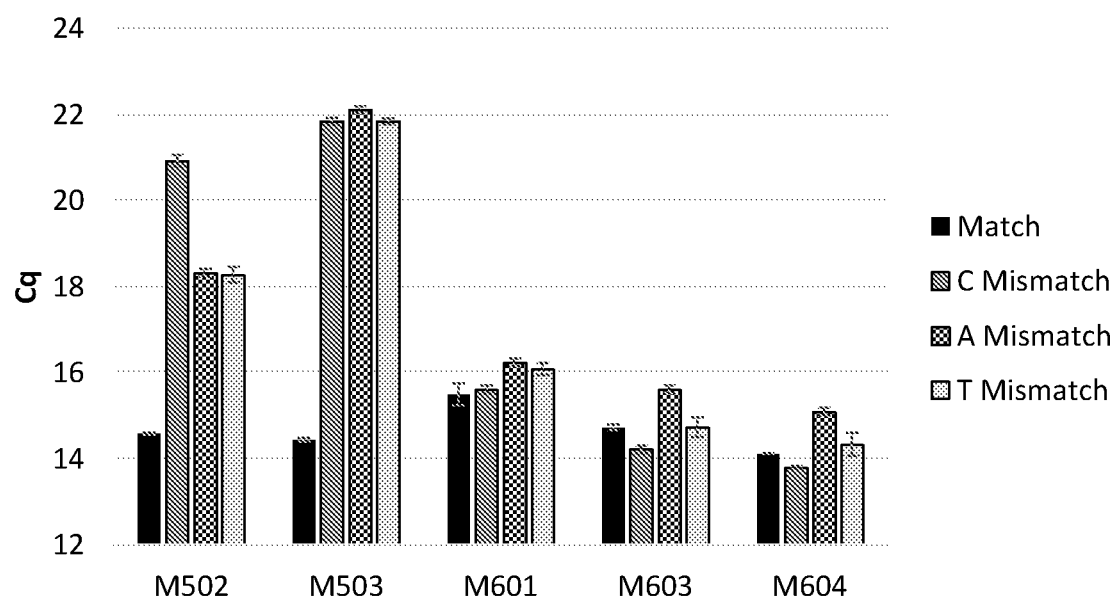

FIG. 22: Proofreading on a DNA-primed RNA template using the 3'→5' nuclease-active mutants was demonstrated by comparing the efficiency of the extension of a primer with a 3'-terminal matched base pair versus the three possible 3'-terminal mismatched base pairs, as indicated. Error bars represent the standard deviation of triplicate reactions.

DETAILED DESCRIPTION OF THE INVENTION

Definitions

Unless defined otherwise, all technical and scientific terms used herein have the same meaning as commonly understood by one of ordinary skill in the art (e.g., in cell culture, molecular genetics, nucleic acid chemistry, hybridization techniques and biochemistry).

In practicing the present invention, many conventional techniques in molecular biology, microbiology, and recombinant DNA may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985 (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods In Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

As used herein, the term "comprising" is to be construed as encompassing both "including" and "consisting of", both meanings being specifically intended, and hence individually disclosed embodiments in accordance with the present invention.

The term "DNA" in the present invention relates to any one of viral DNA, prokaryotic DNA, archaeal DNA, and eukaryotic DNA. The DNA may also be obtained from any one of viral RNA, and mRNA from prokaryotes, archaea, and eukaryotes by generating complementary DNA (cDNA) by using a reverse transcriptase.

The term "PCR" refers to polymerase chain reaction, which is a standard method in molecular biology for DNA amplification.

"RT-PCR" relates to reverse transcription polymerase chain reaction, a variant of PCR commonly used for the detection and quantification of RNA. RT-PCR comprises two steps, synthesis of complementary DNA (cDNA) from RNA by reverse transcription and amplification of the generated cDNA by PCR. Variants of RT-PCR include quantitative RT-PCR (RT-qPCR), real-time RT-PCR, digital RT-PCR (dRT-PCR) or digital droplet RT-PCR (ddRT-PCR).

"Methods of amplifying RNA without high temperature thermal cycling" as referred to herein, may be isothermal nucleic acid amplification technologies, such as loop-mediated amplification (LAMP), helicase dependent amplification (HDA) and recombinase polymerase amplification (RPA).

"Truncate", "truncation" or "truncated" as referred to herein includes modifications of the N-terminal sequences incorporated during synthesis of the corresponding nucleic acids encoding the proteins. Despite a common, stricter usage in the art that does not include modification of the N-terminus, as used herein, "truncate" and its derivatives "truncation" and "truncated" may encompass both reduction in molecular weight and modification of the N-terminal sequence as defined herein.

Polymerases/Enzymes

In a first aspect, the present invention provides polypeptides comprising a polymerase domain comprising an amino acid sequence of SEQ ID NO:16 and an amino acid sequence selected from the group consisting of SEQ ID NO:17 and SEQ ID NO:72, or amino acid sequences at least 90%, preferably at least 95%, more preferably at least 98% identical thereto. Preferably, the polypeptides of the present invention comprise a polymerase domain comprising an amino acid sequence of SEQ ID NO:16 and an amino acid sequence selected from the group consisting of SEQ ID NO:17 and SEQ ID NO:72. In one embodiment, the polypeptides of the present invention comprise a polymerase domain comprising the amino acid sequence of SEQ ID NO:16 and an amino acid sequence at least 90%, preferably at least 95%, more preferably at least 98% identical to the amino acid sequence of SEQ ID NO:17 or SEQ ID NO:72. In another embodiment, the polypeptides of the present invention comprise a polymerase domain comprising the amino acid sequence of SEQ ID NO:17 or SEQ ID NO:72 and an amino acid sequence at least 90%, preferably at least 95%, more preferably at least 98% identical to SEQ ID NO:16.

In some embodiments, the N-terminus of the polymerase domain corresponds to the sequence of positions 12-22 of the sequence of SEQ ID NO:15, ora sequence at least 90%, preferably at least 95%, more preferably at least 98% identical thereto. In other embodiments, the N-terminus of the polymerase domain corresponds to the sequence of positions 12-25, more preferably 12-27, most preferably 12-30 of SEQ ID NO:15, or a sequence at least 90%, preferably at least 95%, more preferably at least 98% identical thereto.

In some preferred embodiments, the N-terminus is an amino acid sequence of "MN($X_1$)PKPILKPQ($X_2$)KALVE-PVLC($X_3$)SI($X_4$)EIPA" (SEQ ID NO:21); or variants thereof, wherein $X_1$=A or T; $X_2$=P or S; $X_3$=N or D; and $X_4$=N or D.

In some preferred embodiments, the polymerase domain of the polypeptide of the present invention comprises an amino acid sequence of SEQ ID NO:2, SEQ ID NO:4, SEQ ID NO:6, SEQ ID NO:8, SEQ ID NO:10, or SEQ ID NO:12, or an amino acid sequence at least 95% identical thereto. In some particularly preferred embodiments, the polypeptide of the invention comprises a polymerase domain having an amino acid sequence as shown in SEQ ID NO:4.

In some embodiments, the polypeptide of the present invention has an amino acid sequence as shown in SEQ ID NO:2, SEQ ID NO:4, SEQ ID NO:6, SEQ ID NO:8, SEQ ID NO:10, SEQ ID NO:12, or SEQ ID NO:14, or an amino acid sequence at least 90%, preferably at least 95%, more preferably at least 98% identical thereto. In some particularly preferred embodiments, the polypeptide of the invention has an amino acid sequence as shown in SEQ ID NO:4.

In some embodiments, the proofreading 3'→5' exonuclease activity is disabled by at least one point mutation. In other embodiments, the proofreading activity can be reconstituted by reversion of this point mutation. The native enzyme molecules from which the polypeptides of the invention were derived, e.g. SEQ ID NO:15, have inherent proofreading 3'→5' exonuclease activity. Since this activity may interfere with certain common analytical applications, in some embodiments, e.g., in the polypeptides comprising the amino acid sequences of SEQ ID NO:2, SEQ ID NO:4, SEQ ID NO:6, SEQ ID NO:8, SEQ ID NO:10, SEQ ID NO:12, or SEQ ID NO:14, SEQ ID NO:18, SEQ ID NO:19, SEQ ID NO:20, SEQ ID NO:49, SEQ ID NO:51, SEQ ID NO:53, SEQ ID NO:55, or an amino acid sequence at least 90%, preferably at least 95%, more preferably at least 98% identical thereto, this activity has been disabled by at least one point mutation. A preferred embodiment (for analytic uses) is a polypeptide comprising the amino acid sequence of SEQ ID NO:55, or an amino acid sequence at least 90%, preferably at least 95%, more preferably at least 98% identical thereto.

In other embodiments, this point mutation has been reversed so that the proofreading activity is reconstituted. One can envision certain uses, especially preparative applications, in which the increased accuracy of synthesis provided by such a proofreading activity would be advantageous. In one embodiment, the polypeptide comprising a restored proofreading activity comprises an amino acid sequence of SEQ ID NO:45, or an amino acid sequence at least 90%, preferably at least 95%, more preferably at least 98% identical thereto. In other embodiments, the polypeptide comprising a restored proofreading activity has an amino acid sequence of SEQ ID NO:45, SEQ ID NO:47, SEQ ID NO:74, SEQ ID NO:76, SEQ ID NO:78 or SEQ ID NO:80 or an amino acid sequence at least 90%, preferably at least 95%, more preferably at least 98% identical thereto. A preferred embodiment (for preparative uses) is a polypeptide comprising the amino acid sequence of SEQ ID NO:80, or an amino acid sequence at least 90%, preferably at least 95%, more preferably at least 98% identical thereto.

In some preferred embodiments, in addition to the polymerase domain, the polypeptide of the invention further comprises a 5'→3' exonuclease domain connected to the polymerase domain, preferably via a linker.

Suitable linkers may be amino acid linkers comprising 5-15 amino acids, more preferably 7-12 amino acids, most preferably 9-11 amino acids. In a preferred embodiment, the linker has the sequence "GGGGSGGGS" (SEQ ID NO:22). Alternatively, suitable linkers may be non-amino acid linkers.

In polypeptides according to the invention comprising a 5'→3' exonuclease domain connected to the polymerase domain, for instance via a linker, the N-terminus of the polymerase domain comprises the sequence of positions 13-22, preferably of positions 13-25, more preferably of positions 13-27, most preferably of positions 13-30 of the sequence of SEQ ID NO:15.

Advantageously, polypeptides of the present invention comprise an additional 5'→3' exonuclease domain to facilitate fluorescent detection of the amplification products, for instance using hydrolysis probes, such as TaqMan probes. In some embodiments, such a polypeptide comprising a polymerase domain and an additional exonuclease domain comprises an amino acid sequence of SEQ ID NO:14, SEQ ID NO:45, SEQ ID NO:47, SEQ ID NO:49, SEQ ID NO:51, SEQ ID NO:53, SEQ ID NO:55, SEQ ID NO:74, SEQ ID NO:76, SEQ ID NO:78 or SEQ ID NO:80 or an amino acid sequence at least 90%, preferably at least 95%, more preferably at least 98% identical thereto. In some preferred embodiments, a polypeptide comprising a polymerase domain and an exonuclease domain has an amino acid sequence at least 90%, preferably at least 95%, more preferably at least 98%, most preferably 100% identical to SEQ ID NO:14, SEQ ID NO:45, SEQ ID NO:47, SEQ ID NO:49, SEQ ID NO:51, SEQ ID NO:53, SEQ ID NO:55, SEQ ID NO:74, SEQ ID NO:76, SEQ ID NO:78 or SEQ ID NO:80. In some particularly preferred embodiments, such polypeptide comprises an amino acid sequence at least 90%, preferably at least 95%, more preferably at least 98%, most preferably 100% identical to SEQ ID NO:55. In other particularly preferred embodiments, such polypeptide comprises an amino acid sequence at least 90%, preferably at least 95%, more preferably at least 98%, most preferably 100% identical to SEQ ID NO:80.

Preferably, a polypeptide according to the invention comprises an amino acid sequence at least 90%, preferably at least 95%, more preferably at least 98% identical to SEQ ID NO:14, wherein one or more of amino acids H751, Q752, L753, W777, D781, D622, or Q627 of SEQ ID NO:14 is substituted. More preferably, a polypeptide according to the invention comprises an amino acid sequence at least 90%, preferably at least 95%, more preferably at least 98% identical to SEQ ID NO: 14, wherein SEQ ID NO:14 comprises at least one or more of the following substitutions: H751Q, Q752K, L753K, W777C, D781A, D622N, and/or Q627N. More preferably, a polypeptide according to the invention comprises an amino acid sequence at least 90%, preferably at least 95%, more preferably at least 98% identical to SEQ ID NO:14, wherein SEQ ID NO:14 comprises one of the following groups of substitutions: Q627N, H751Q, Q752K, and L753K; or H751Q, Q752K, and L753K; or W777C, D781A, D622N and Q627N. Most preferably, a polypeptide according to the invention comprises an amino acid sequence at least 90%, preferably at least 95%, more preferably at least 98% identical to SEQ ID NO:14, wherein SEQ ID NO:14 comprises the following substitutions: Q627N, H751Q, Q752K, L753K. Accordingly, most preferably, a polypeptide according to the invention comprises an amino acid sequence at least 90%, preferably at least 95%, more preferably at least 98% identical to SEQ ID NO:55 having the following substitutions: Q627N, H751Q, Q752K, L753K. Similarly, most preferably, a polypeptide according to the invention comprises an amino acid sequence at least 90%, preferably at least 95%, more preferably at least 98% identical to SEQ ID NO:80 having the following substitutions: Q627N, H751Q, Q752K, L753K. Advantageously, polypeptides having the indicated mutations exhibit beneficial properties, such as increased resistance to PCR inhibitors or salt tolerance, while retaining good polymerase activity and RT activity.

In some embodiments, the polypeptide of the invention exhibits reverse transcriptase activity. In other embodiments, the polypeptide of the invention exhibits 5'→3' exonuclease activity. In some embodiments the 5'→3' exonuclease domain can be included, but the catalytic activity can be disabled by point mutation, as is known in the art, to provide enhanced nucleic acid binding affinity while avoiding nuclease catalytic activity when it might interfere with an intended application. In still another embodiment the 5'→3' exonuclease domain could be included for binding affinity, but disabled catalytically, while the 3'→5' proofreading exonuclease activity can be reconstituted and active.

Beneficially, the activity of the polypeptides of the invention does not require the presence of manganese so that the polypeptides of the inventions may be used in conventional magnesium containing buffers. This compatibility with magnesium provides practical advantages in simplicity of reaction formulation and accuracy of synthesis, as is known in the art.

In one aspect, the polypeptides according to the invention are used in a method of the invention. In another aspect, the invention relates to compositions comprising a polypeptide of the invention.

Another aspect of the invention refers to vectors encoding a polypeptide of the invention. In some embodiments, the vector comprises a nucleic acid sequence as shown in SEQ ID NO: 1, SEQ ID NO:3, SEQ ID NO:5, SEQ ID NO:7, SEQ ID NO:9, SEQ ID NO:11, or SEQ ID NO:13. In a particularly preferred embodiment, the vector coding for a polypeptide of the invention comprises a nucleic acid sequence as shown in SEQ ID NO:3. Alternatively, the vector comprises a nucleic acid sequence as shown in SEQ ID NO:13, more preferably the vector comprise a nucleic acid sequence as shown in any of SEQ ID NO:50, SEQ ID NO:52, SEQ ID NO:54, SEQ ID NO:73, SEQ ID NO:75, SEQ ID NO:77 or SEQ ID NO:79. In a particularly preferred embodiment, the vector comprises a nucleic acid sequence as shown in SEQ ID NO:54. In another particularly preferred embodiment, the vector comprises a nucleic acid sequence as shown in SEQ ID NO:79.

Another aspect of the invention relates to transformed host cells comprising such vector, such as *E. coli* or other suitable host cells.

Methods

In another aspect, the present invention refers to methods for amplifying template nucleic acids comprising contacting the template nucleic acids with a polypeptide according to the invention.

Template nucleic acids according to the present invention may be any type of nucleic acids, such as RNA, DNA, or RNA:DNA hybrids. Template nucleic acids may either be artificially produced (e.g. by molecular or enzymatic manipulations or by synthesis) or may be a naturally occurring DNA or RNA. In some preferred embodiments, the template nucleic acids are RNA sequences, such as transcription products, RNA viruses, or rRNA.

Advantageously, the method of the invention also enables amplification and detection/quantification of template nucleic acids, such as specific RNA target sequences, out of a complex mixture of target and non-target background RNA. For instance, the method of the invention allows amplification of an mRNA transcript from total human RNA or amplification of rRNA directly from bacterial cell lysate.

In some embodiments, the method referred to herein is RT-PCR. RT-PCR may be quantitative RT-PCR (RT-qPCR), real-time RT-PCR, digital RT-PCR (dRT-PCR) or digital droplet RT-PCR (ddRT-PCR).

In other embodiments, the method referred to herein is a method of amplifying RNA without high temperature thermal cycling, such as loop-mediated isothermal amplification (LAMP), helicase dependent amplification (HDA) and recombinase polymerase amplification (RPA).

In some preferred embodiments, the method of the invention comprises the steps of
   a) generating cDNA using a polypeptide of the invention; and
   b) amplifying the generated cDNA using a polypeptide of the invention.

In some embodiments, the method of the invention further comprises detecting and/or quantifying the amplified nucleic acids. Quantification/detection of amplified nucleic acids may be performed, e.g., using non-sequence-specific fluorescent dyes (e.g., SYBR® Green, EvaGreen®) that intercalate into double-stranded DNA molecules in a sequence non-specific manner, or sequence-specific DNA probes (e.g., oligonucleotides labelled with fluorescent reporters) that permit detection only after hybridization with the DNA targets, synthesis-dependent hydrolysis or after incorporation into PCR products.

In some preferred embodiments, in the method of the invention, the same polypeptide is applied for generating cDNA in step a) and for amplifying the generated cDNA in step b). Advantageously, in the method of the invention, reverse transcription and subsequent amplification of the generated cDNA may be performed in a single enzyme format. In other particularly preferred embodiments, the generation of cDNA in step a) and the amplification of the generated cDNA in step b) are performed at isothermal conditions. Suitable temperatures may, for instance, be between 30-96° C., preferably 55-95° C., more preferably 55-75° C., most preferably 55-65° C.

In some embodiments, in the method of the invention, a polypeptide of the invention is used in combination with Taq DNA polymerase. In other embodiments, human serum albumin is added during amplification, preferably at a concentration of 1 mg/ml.

Kits

Reagents necessary to perform the method of the invention may be comprised in kits.

In some embodiments, the invention relates to kits for amplifying template nucleic acids, wherein the kit comprises a polypeptide of the invention and a buffer. Optionally, the kit additionally comprises Taq DNA polymerase and/or serum albumin. Buffers comprised in the kit may be conventional buffers containing magnesium. Suitable buffer solutions do not need to contain manganese.

EXAMPLES

The invention is illustrated in the following examples.

Example 1: Expression of Truncated DNA Polymerases

The 588 amino acid sequence shown in GenBank Acc. No. AFN99405.1, presumptively comprising the PyroPhage polymerase (Lucigen, Middleton, Wis.), contains a sequencing error from amino acid positions 450 to 463. This error was corrected by submission of GenBank Acc. No. AGL03984, a 611 amino acid open reading frame, the carboxyterminal 588 amino acids of which comprise the correct PyroPhage polymerase sequence. The corrected 588 amino acid sequence, including mutation E51A intentionally incorporated to eliminate exonuclease activity, is shown in SEQ ID NO:15. This enzyme was purified numerous times and the performance of the enzyme preparations in RT-PCR was highly variable. In two representative examples (Lots 1 and 4151), this molecule was purified to varying degrees of homogeneity by iterative rounds of affinity and ion exchange column chromatography as is well known in the art, and the molecular weights of the generated products were determined by SDS PAGE. The Lot 1 preparation (FIG. 1, Panel A, Lane 2) shows a homogeneous enzyme estimated to comprise the full-length 588 amino acid molecule of SEQ ID NO:15. Lot 4151 (FIG. 1, Panel A, Lane 2) was less completely purified, as evidenced by spurious bands of lower molecular weight. A close examination of the SDS PAGE data (FIG. 1, Panel A, Lane 2) reveals that the apparent major band is actually two bands estimated to correspond to 588 (SEQ ID NO:15) and 577 (SEQ ID NO:18) amino acids.

Figure 1:
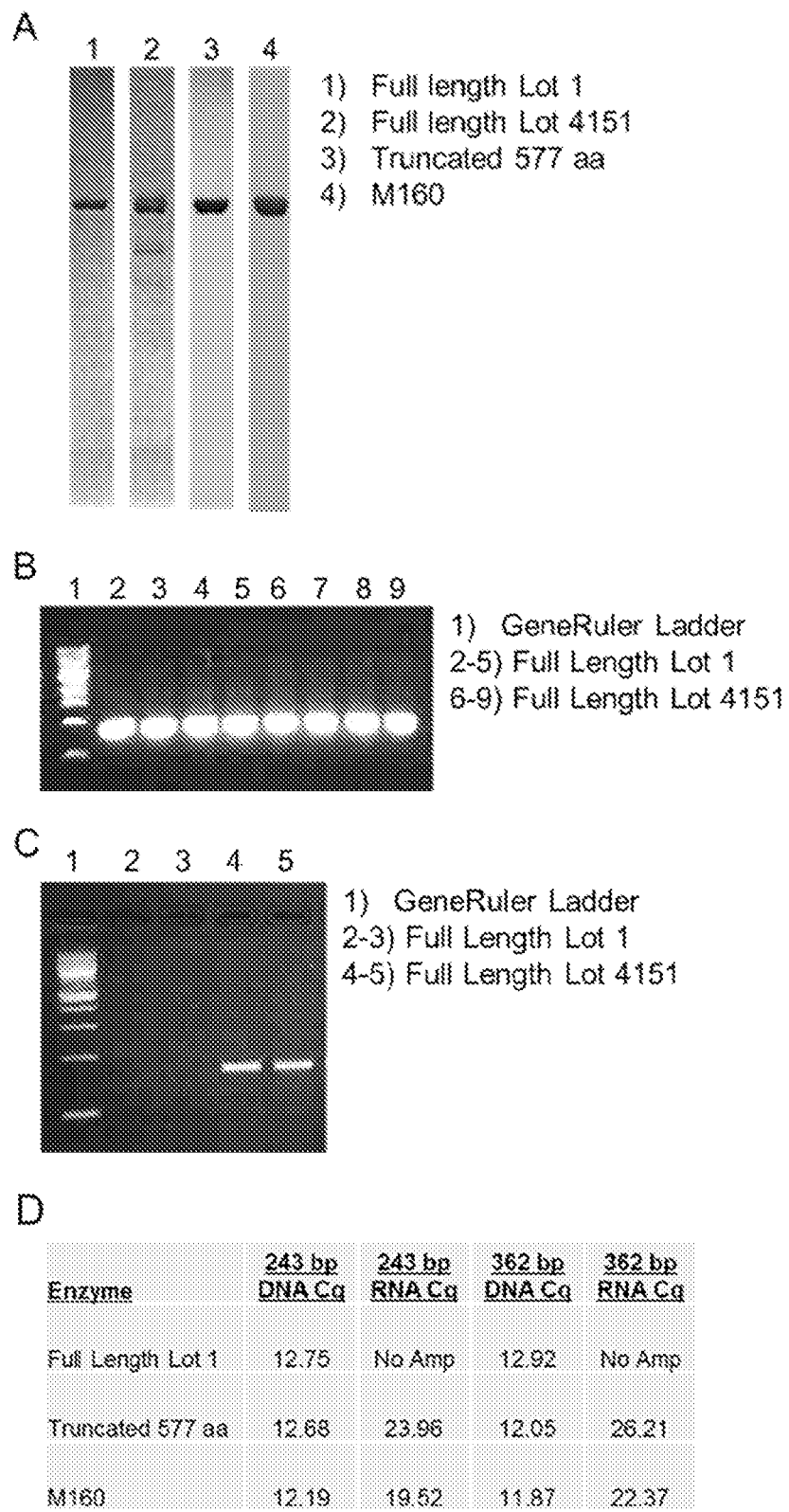
FIG. 1: Truncated 3173 polymerase maintains RT activity when extensively purified.
   Panel A. SDS-PAGE images of 1) full-length 3173 polymerase lot 1 purified extensively, 2) partially purified 3173 polymerase lot 4151, 3) Extensively purified truncated 3173 polymerase, and 4) extensively purified M160 polymerase.

Lots 1 and 4151 were tested in quadruplicate reactions for their ability to PCR amplify a 860 bp DNA target from the pUC19 beta-lactamase gene. Equivalent quantities of enzyme were thermal cycled under conditions described for a control PCR in the PyroPhage® 3173 DNA polymerase, Exo-product manual (MA 100 v. 1.0, Lucigen Corp.). DNA products were analyzed by agarose gel electrophoresis (FIG. 1, Panel B, Lanes 2 to 5 and Lanes 6 to 9). The DNA product was present in all lanes indicating that both enzyme preparations were fully capable of PCR amplifying from DNA templates.

Lots 1 (FIG. 1, Panel C, Lanes 2 to 3) and 4151 (FIG. 1, Panel C, Lanes 4 to 5) were tested in duplicate reactions for their ability to RT PCR amplify MS2 phage RNA. Using the control RT-PCR conditions described in the PyroScript™ RT-PCR 2× Master Mix Kit manual (MA 102, Lucigen Corp.), equivalent units of enzyme were thermal cycled and the products were analyzed by agarose gel electrophoreses. In this case, only the less purified Lot 4151 generated the expected 160 bp product, indicating successful amplification from the RNA template and suggesting the RT-PCR capacity is associated with a lower molecular weight product seen in FIG. 1, Panel A, Lane 2.

Examination of the corrected sequence corresponding to GenBank Acc. No. AFN99405.1 (SEQ ID NO:15) shows two methionine residues at positions 11 and 12. It was hypothesized that the reverse transcription activity was associated with a 577 amino acid translation product generated by spurious internal translational initiation or, alternatively, proteolysis to generate a product initiating at the position 12 methionine. The variability in the generation of this product is believed to result in a mix of 588 and 577 amino acid products (SEQ ID NOs: 15 and 18) and, therefore, the variability or ineffectiveness of some preparations in RT-PCR. Purification to homogeneity of the 588 amino acid product, as in Lot 1, results in an enzyme preparation that fails to reverse transcribe RNA targets prior to PCR amplification.

To test the hypothesis that the 577 amino acid enzyme is the active form of the enzyme responsible for reverse transcriptase activity, a gene construct that encodes the 577 amino acid protein truncated at the N terminus by 11 amino acids, but otherwise identical to SEQ ID NO:15, was used to produce homogenous 577 amino acid product, the sequence of which is shown in SEQ ID NO:18.

The 577 amino acid product was tested (FIG. 1, Panel D) in RT-PCR in 20 µl reactions containing 50 mM Tris, pH 8.7, 75 mM KCl, 4 mM $MgCl_2$, 0.3 mM dNTPs, 0.04 mg/ml human serum albumin, 0.2 M trehalose, 0.2× EvaGreen dye (Biotium), 0.3 µM forward and reverse primer (25 nucleotides each in size), 300 ng polymerase, and either $1\times10^7$ copies of MS2 phage RNA (Roche) or $1\times10^7$ copies of a synthetic double-stranded DNA gene block (IDT) with sequence corresponding to MS2 RNA. The 243 bp amplicon corresponded to position 472 to 714 of the MS2 genome (GenBank Acc. No. V00642.1; SEQ ID NO:23) and the 362 bp amplicon corresponded to position 353 to 714 of the MS2 genome. Reactions were thermal cycled in a StepOnePlus (Thermo Fisher) as follows: 94° C. 30 sec (×1), 94° C. 3 sec, 64° C. 1 minute (×40).

As hypothesized and in contrast to the full length 588 amino acid product in Lot 1, this 577 amino acid truncated enzyme had reproducible performance in RT-PCR (FIG. 1, Panel D). This 577 amino acid enzyme truncation product of SEQ ID NO:15 was used as Parent 1 (SEQ ID NO:18) in subsequent work described below.

Example 2: Testing of Parent Molecules

Six viral DNA polymerase genes ranging from 100% to 44% compared to Parent 1 (SEQ ID NO:18) were identified in a published source (Schoenfeld, 2013). Truncated derivatives of each were mutagenized to eliminate 3'-5' exonuclease activity as described (Moser et al, 2008), expressed and tested for RT activity and thermostability. Three of the six constructs were chosen for shuffling based on enhanced thermostability (Parents 1 and 3, SEQ ID NOs: 18 and 20) or high reverse transcriptase activity (Parent 2, SEQ ID NO:19).

Example 3: Generation and Screening of Clone Libraries

Clones were generated by dividing each of the genes encoding Parent enzymes 1, 2 and 3 (SEQ ID NO:18, SEQ ID NO:19, SEQ ID NO:20) into nine homologous segments and randomly shuffling the sequences with each other. The DNA segments for each of these regions were synthesized based on the sequences of Parents 1, 2 and 3, respectively and shuffled using the RepliQa™ Assembly Mix (Quantabio) according to the manufacturer's recommendation. Over 400 clones were expressed in *E. coli* and screened for performance in RT-PCR by measuring the ability of crude heat-treated lysate to amplify the 243 bp segment of MS2 phage RNA. Whereas most of the clones were completely nonfunctional or had diminished performance in RT-PCR, six of the mutant enzymes (M66, M160, M180, M295, M384, and M392) had enhanced performance in RT-PCR compared to both the full length enzyme (GenBank Acc. No. AFN99405.1; SEQ ID NO:15) and truncated Parent 1 (SEQ ID NO:18) as evidenced by lower Cq values (Table 1).

TABLE 1

| High-efficiency polymerase variants. | | | | |
| --- | --- | --- | --- | --- |
| Variant | Nucleic acid sequence | Amino acid sequence | Amino acid conservation compared to parent 1 | Cycle threshold for detection of MS2 by RT-qPCR |
| Parent 1 | | Truncated sequence derived from SEQ ID NO: 15 (SEQ ID NO: 18) | 100% | 17.3 |
| Parent 2 | | Truncated sequence derived from the sequence of | 84% | None detected |

TABLE 1-continued

High-efficiency polymerase variants.

| Variant | Nucleic acid sequence | Amino acid sequence | Amino acid conservation compared to parent 1 | Cycle threshold for detection of MS2 by RT-qPCR |
|---|---|---|---|---|
| Parent 3 | | GenBank AGL03983 (SEQ ID NO: 19) Truncated sequence derived from the sequence of GenBank AGL03985 (SEQ ID NO: 20) | 93% | 26.4 |
| M66 | SEQ ID NO: 1 | SEQ ID NO: 2 | 92% | 15.3 |
| M160 | SEQ ID NO: 3 | SEQ ID NO: 4 | 89% | 12.1 |
| M180 | SEQ ID NO: 5 | SEQ ID NO: 6 | 94% | 14.4 |
| M295 | SEQ ID NO: 7 | SEQ ID NO: 8 | 94% | 12.9 |
| M384 | SEQ ID NO: 9 | SEQ ID NO: 10 | 95% | 14.6 |
| M392 | SEQ ID NO: 11 | SEQ ID NO: 12 | 95% | 14.5 |
| M160-nuc | SEQ ID NO: 13 | SEQ ID NO: 14 | 89% | not determined |

Example 4. Bioinformatic Analysis of the RT-PCR Competent Clones

In the original analysis, Parent 2 (SEQ ID NO:19) had higher RT activity, but inadequate thermostability for RT-PCR. In contrast, Parents 1 (SEQ ID NO:18) and 3 (SEQ ID NO:20) had higher thermostability, but lower RT activity. Presumably the sequences comprising enhanced RT-PCR clones are combinations of the regions of the parents that confer the optimal combination of these functions, i.e., a region comprising the amino acid sequence of SEQ ID NO:16 and a region comprising an amino acid sequence selected from the group consisting of SEQ ID NO:17 and SEQ ID NO:72, or amino acid sequences at least 90%, preferably at least 95%, more preferably 98% identical thereto. The sequences of the enhanced RT-PCR clones were compared to those of the ineffective RT-PCR clones to identify common features conserved in the enhanced RT-PCR enzyme constructs but not the ineffective enzymes. Although there were numerous positions that varied among the enhanced RT-PCR clones, this analysis identified a region (amino acids 400 to 472) between motifs B and C (Delarue, 1990) that was fully conserved and apparently derived from Parent 2 (SEQ ID NO:19; FIG. 2, Panel A). In better characterized Family A DNA polymerases, this inter-motif region is characterized by two alpha helices, 0 Helix and P Helix and Beta Sheets 10 and 11, known to be in close contact with the template (Li, 1998). This proximity to the template is very consistent with the improved utilization of the non-natural RNA template. In all the positive clones, the bulk of the sequence outside this inter-motif region is derived from Parents 1 and 3 (SEQ ID NO:18 and SEQ ID NO:20) and the residues conserved in these Parents are more distributed. However, the region between residues 231 to 260 of all the enhanced RT-PCR clones are conserved and appear derived from Parent 1 or 3, which are almost identical in this region (FIG. 2, Panel B). This region includes H helix, which appears to be critical to binding the phosphate backbone of the template in both the open and closed forms (Li, 1998).

Example 5: High-Efficiency Polymerase Variants

Of the six RT PCR enhanced variants, M160 provided the shortest cycle threshold and was used for further development. This enzyme was further improved by fusing to its N-terminus a domain from the Taq DNA polymerase enzyme that conferred 5'→3' exonuclease activity and consequently the ability to utilize hydrolyzable probes such as TaqMan (Roche) probes.

As shown in the following examples, the fusion construct M160-nuc had the additional advantage of improving reverse transcriptase activity at elevated temperatures (FIGS. 3 and 4), and RNA detection sensitivity (FIG. 5). The M160-nuc can detect amplification by dye-based chemistry or hydrolyzable probes (FIG. 6) and can detect viral RNA (FIG. 7), mRNA transcripts (FIG. 8) and bacterial rRNA (FIG. 9) with high sensitivity and fast time to result compared to alternative two enzyme RT-PCR systems.

Example 6: Reverse Transcriptase Activity

Reverse transcriptase activities of the purified variant M160 and the purified fusion construct M160-nuc, in which the 5'→3' nuclease domain from Taq polymerase was fused to the N-terminus of M160 via a 10-amino acid flexible linker, were assessed at different temperatures and the activities were compared. Reactions (20 μl) containing 50 mM Tris, pH 8.3, 75 mM NaCl, 5 mM $MgCl_2$, 1 mM DTT, 0.01% Tween-20, 2% trehalose, 0.4× EvaGreen dye (Biotium), 0.8 mM dTTP, 0.01 ug/μl Poly(A), 0.1 μM olgo(dT)20 primer, and 0-20 ng polymerase were incubated at the indicated temperature and fluorescence readings were taken every 15 seconds. The initial slopes of fluorescence curves were calculated and compared for each polymerase.

FIG. 3 shows relative reverse transcriptase activities of M160 and M160-nuc at different temperatures (55° C. and 60° C.). In addition to demonstrating that the presence of the 5'→3' nuclease domain does not interfere with M160 reverse transcriptase activity at high temperature, the results indicate that the nuclease domain improves activity, presumably by increasing affinity of the enzyme for the nucleic acid template.

Example 7: Measurement of Thermal Activity Profile

DNA polymerase activities of M160-nuc were measured by determining the relative rates of nucleotide incorporation (FIG. 4) using either a primed M13 template or activated calf thymus DNA, each of which is an effective substrate over different temperature ranges. Both types of reaction contained 20 mM Tris, pH 8.8, 10 mM $(NH_4)_2SO_4$, 10 mM KCl, 2 mM $MgSO_4$, and 0.1% Triton X-100. The M13-based reactions (20 μl) also contained 200 uM dNTPs, 1×SYBR Green I (Thermo Fisher), 7.5 μg/ml M13mp18 DNA, 0.25 mM each of a mixture of three primers 24-33 nt in size, and 0.03-1 ng of M160-nuc enzyme. Reactions were incubated at the indicated temperature, fluorescence readings were taken every 15 seconds, and fluorescence initial slope values were calculated and compared. For the calf thymus DNA-based reactions, reactions (50 μl) also contained 4 μg activated calf thymus DNA, 100 μM dNTPs, 7.5 μCi/ml $^3$H-dTTP, and 0.8-25 ng M13-nuc polymerase. Reactions were incubated at the indicated temperatures, then the TCA-insoluble radioactive counts were measured. The slopes of the initial rates of nucleotide incorporation were then determined and compared. In both cases the temperature at which the activity was highest was set at 100% activity and other values were plotted relative to this number. As shown in FIG. 4, the M160-nuc construct displays peak activity from 65'-80° C.

Example 8: Presence of 5' Nuclease Domain Improves Sensitivity and Efficiency of Detection of Viral RNA The M160 (FIG. 5, Panel A) or M160-nuc (FIG. 5, Panel B) constructs were tested in RT-qPCR amplification using serial dilutions of MS2 RNA template. In both cases amplifications were performed without a pre-incubation step prior to thermal cycling.

Reactions (20 μl) contained 50 mM Tris, pH 8.7, 75 mM KCl, 4 mM $MgCl_2$, 0.3 mM dNTPs, 0.04 mg/ml human serum albumin, 0.2 M trehalose, 0.225× EvaGreen dye (Biotium), the indicated number of copies of MS2 phage RNA, 0.3 μM forward and reverse primer (25 nucleotides each in size), and 300 ng polymerase. The amplicon was 531 bp in size and corresponded to position 184 to 714 of the MS2 genome (GenBank Acc. No. V00642.1; SEQ ID NO:23). Reactions were thermal cycled in a StepOnePlus (Thermo Fisher) as follows: 94° C. 30 sec (×1), 94° C. 3 sec, 64° C. 1 minute (×40). Compared with M160 alone (FIG. 5, Panel A), the M160-nuc (FIG. 5, Panel B) polymerase displays significantly improved detection sensitivity and amplification at lower cycle numbers, indicated by lower Cq values and higher efficiency amplification.

Example 9: M160-Nuc Compatibility with Dye- and Probe-Based qPCR Reaction Chemistry To test capacity of M160-nuc to support detection by hydrolysable probes, RT-qPCR reactions were performed using either EvaGreen-based detection chemistry or by using a dual-quenched FAM-labeled hydrolysis probe for amplification detection (FIG. 6). Reactions (20 μl) contained 50 mM Tris, pH 8.75, 75 mM KCl, 3 mM $MgCl_2$, 0.3 mM dNTPs, 0.04 mg/ml human serum albumin, 0.2 M trehalose, the indicated number of copies of MS2 phage RNA, 0.3 μM forward and reverse primer (25 nucleotides each in size), and 100 ng of M160-nuc polymerase. The amplicon was 362 bp in size and corresponded to position 353 to 714 of the MS2 genome (GenBank Acc. No. V00642.1; SEQ ID NO:23). Dye-based reactions contained 0.225× Eva Green (Biotium) and probe-based reactions contained 0.2 μM of a 5'-FAM/internal ZEN/3'-Iowa Black quenched 22 nt oligonucleotide (MS2 position 650-671). Reactions were thermal cycled in a QuantStudio system (Thermo Fisher) as follows: 94° C. 30 sec (×1), 94° C. 3 sec, 72° C. 1 minute (×40). In both cases, serially diluted MS2 RNA was used as template and the resulting Cq values were assessed. The equivalent Cq values indicate compatibility of the M160-nuc polymerase with both detection chemistries in terms of sensitivity and efficiency.

Example 10: Comparison of M160-Nuc with Two-Enzyme RT-PCR Mix

Hydrolysis probe-based qPCR reactions were performed with dilutions of either a synthetic double-stranded DNA molecule corresponding to a portion of the MS2 phage genomic RNA sequence (FIG. 7, Panel A) or using single-stranded MS2 phage RNA (FIG. 7, Panel B). The 25 nt primers generate a 531 bp product and corresponded to position 184 to 714 of the MS2 genome (GenBank Acc. No. V00642.1; SEQ ID NO:23). M160-nuc reactions were thermal cycled at 94° C. 30 sec (1 cycle), 94° C. 3 sec, 72° C. 1 minute (40 cycles) and reactions with the Taq/MMLV RNase H-enzyme mixture (ZipScript, QIAGEN) were additionally pre-incubated at 50° C. for 15 min.

Whereas reactions with the Taq/MMLV RNase H-enzyme mixture required a pre-incubation step (50° C., 15 min) in the RNA reactions for cDNA conversion because the MMLV enzyme is thermolabile and denatures during the cycling phase, the M160-nuc polymerase does not require a pre-incubation phase because it is highly active at the temperatures used for DNA extension during cycling conditions (72° C.).

In addition, the Cq values for the Taq/MMLV RNase H-mixture were approximately 5.5 cycles higher than with the M160-nuc polymerase, indicating that the M160-nuc polymerase is significantly more efficient at reverse transcription of the highly structured MS2 RNA genome during the PCR cycling phase (72° C.) compared with the MMLV RNase H-enzyme during the pre-incubation phase (50° C.).

Example 11: Amplification of an mRNA Transcript from Total Human RNA

To test the capacity of the M160-nuc enzyme to detect mRNA transcripts, the M160-nuc polymerase was used to amplify a 145 bp region of the LDHA mRNA from total human RNA using a FAM probe-based RT-qPCR assay (FIG. 8). Reactions (20 μl) contained 50 mM Tris, pH 8.75, 75 mM KCl, 3 mM $MgCl_2$, 0.3 mM dNTPs, 0.04 mg/ml human serum albumin, 0.2 M trehalose, the indicated quantity of total human RNA, 0.3 μM forward and reverse primer (40 nt and 26 nt, respectively), 0.2 uM probe, and 100 ng of M160-nuc polymerase. The amplicon corresponded to position 1428 to 1572 of the LDHA transcript (GenBank Acc. No. NM_005566.3; SEQ ID NO:24). The probe was 34 nt in size, corresponded to position 1509-1542 and contained 5'-FAM/internal ZEN/3'-Iowa Black modifications. Reactions were thermal cycled in a QuantStudio system (Thermo Fisher) as follows: 94° C. 30 sec (×1), 94° C. 3 sec, 72° C. 45 sec (×45). Detection sensitivity was demonstrated to be approximately 200 fg, which corresponds to approximately 5 copies as determined by digital PCR quantification. This demonstrates a high degree of sensitivity and specificity for the M160-nuc polymerase for mRNA detection in the presence of a complex mixture of target and non-target background RNA.

Example 12: Amplification of 16S rRNA Directly from Bacterial Cell Lysate

The capacity of the M160-nuc in detection of a highly structured ribosomal RNA target directly from cell lysate without processing was tested in a RT PCR reaction (FIG. 9). From serial dilutions of total cell lysate, M160-nuc polymerase was used in FAM probe-based RT-qPCR reactions to directly amplify a variable portion of the 16S rRNA. *Vibrio natriegens* cells were grown to early log phase in 2× YT media and the cell number was quantified by plating serial dilutions of cells to LB-agar and growing overnight at 30° C. Cells resuspended in 200 μl of a buffer containing 10 mM Tris, pH 7.5, 0.5 mM EDTA, 100 mM NaCl, 0.1% Triton X-100 and were lysed by addition of 1 μl of Ready-Lyse™ Lysozyme solution (Lucigen) and incubating for 15 minutes at room temperature. The lysate was briefly vortexed and serial dilutions were made using 0.01% Tween-20. Finally, 2 μl of this lysate was used directly in RT-PCR reactions (20 μl) containing 50 mM Tris, pH 8.75, 75 mM KCl, 3 mM $MgCl_2$, 0.3 mM dNTPs, 0.04 mg/ml human serum albumin, 0.2 M trehalose, 0.3 μM forward and reverse primer (25 nt and 26 nt, respectively), 0.2 μM probe, and 100 ng of M160-nuc polymerase. The amplicon (159 nt) corresponded to position 56 to 214 of the *Vibrio natriegens* strain ATCC 14048 16S ribosomal RNA gene (GenBank Acc. No. NR_117890.1; SEQ ID NO:25). The probe was 34 nt in size, corresponded to position 145-178 and contained 5'-FAM/internal ZEN/3'-Iowa Black modifications. Reactions were thermal cycled in a QuantStudio system (Thermo Fisher) as follows: 94° C. 30 sec (1 cycle), 94° C. 3 sec, 72° C. 30 sec (45 cycles). rRNA is present at copy numbers as high as 10,000 per cell. The detection limit by RT-PCR was significantly lower than the extinction limit based on serial plating of cells, demonstrating the efficiency of detection of the structured rRNA in the presence of cell lysate components and the capacity of this method to allow detection of cells at limits of detection well below single cell.

Example 13: Presence of the 5' Nuclease Domain Increases Binding Affinity to Primed-Template DNA To determine whether the increased activity and improved performance characteristics of M160-nuc were correlated with increased binding affinity to primed-template nucleic acid, the enzymes were tested with target substrates using an electrophoretic mobility shift assay (FIG. 10). The sequence and preparation of the primed template oligonucleotides was as previously described (Yamagami et al., 2014). Reactions (30 μl) containing 20 mM Tris, pH 8.8, 10 mM NaCl, 5 mM $MgCl_2$, 1 mM DTT, 0.05 mg/ml BSA, 10% glycerol, and 5 nM unlabeled DNA substrate were incubated with polymerase at 37° C. for 10 minutes to allow equilibrium to be reached, then components were fractionated by native 3-12% polyacrylamide gel electrophoresis. Gels were stained with 2×SYBR Gold (Invitrogen) and the band intensities were quantified. The fraction bound was determined by dividing the intensity of the shifted band by the total DNA signal. Binding affinity to primed-template DNA for M160-nuc (Kd=78.9 nM) increased 12-fold compared with the M160 polymerase (Kd=946 nM) lacking the exonuclease domain.

Example 14: Biochemical Characterization of M160-Nuc Exonuclease Derivatives While not essential for RT PCR-based nucleic acid detection, high nucleotide incorporation fidelity of the reverse transcriptase would be beneficial for preparative applications, e.g. cDNA cloning and RNA-seq methods, where sequence accuracy is important. As noted above, M160-nuc had its proofreading activity eliminated by mutagenesis. The error rate of M160-nuc, measured using a standard blue-white screen of sequence errors in PCR-amplified lacI repressor, was $1.91 \times 10^{-4}$ (Table 2), similar to the error rates measured for retroviral reverse transcriptases and for a variant KOD polymerase with RT activity (Ellefson et al., 2013; Yasukawa et al., 2016). In contrast, in preparations of altered versions of the M160-nuc enzyme in which the 3'→5' proofreading nuclease activity was reactivated with an A339E reversion (Table 2, M401, SEQ ID NO:45), the measured error rate was reduced by nearly two orders of magnitude, resulting in an error rate similar to KOD polymerase, a prototypical proofreading PCR enzyme.

TABLE 2

Biochemical characterization of M160-nuc exonuclease derivatives.

| Enzyme | Nucleic acid sequence | Amino acid sequence | 5'→3' exo | 3'→5' exo | Relative pol activity | Relative RT activity, 50° C. | Relative ssExo activity | Error rate |
|---|---|---|---|---|---|---|---|---|
| M160-nuc | SEQ ID NO 13 | SEQ ID NO 14 | + | − | 1 | 1 | Not detected | $1.91 \times 10^{-4}$ +/− 0.196 |
| M401 | SEQ ID NO 44 | SEQ ID NO 45 | + | + | 0.91 | 1.02 | 0.76 | $2.22 \times 10^{-6}$ +/− 0.02 |
| M402 | SEQ ID NO 46 | SEQ ID NO 47 | − | + | 1.05 | 0.98 | 0.89 | $2.49 \times 10^{-6}$ +/− 0.33 |
| M403 | SEQ ID NO 48 | SEQ ID NO 49 | − | − | 0.72 | 1.03 | Not tested | Not tested |

To discern whether the RT-PCR performance improvement of M160-nuc compared to M160 was due to nuclease activity or simply the presence of the nuclease domain providing enhanced template binding affinity, two additional constructs were generated. In the first of these, M402, the 5'→3' nuclease domain was present but inactivated by the G46D mutation. In the second, M403, both the 5'→3' and the 3'→5' activities were inactivated by mutagenesis. To test for exonuclease activity, reactions (50 μl) containing 50 mM Tris, pH 8.7, 75 mM KCl, 4 mM $MgCl_2$, 0.3 mM dNTPs, 0.04 mg/ml human serum albumin, 0.2 M trehalose, 50 nM $^3$H-dTTP end-labeled single-stranded 59-mer oligonucleotide and 0.39-50 ng polymerase were incubated at 37° C. for 60 minutes.

Reactions were stopped by addition of salmon sperm carrier DNA and TCA-soluble radioactive counts were measured. Exonuclease activity measurements were made relative to Pfu polymerase. Elimination of the 5'→3' nuclease did not have a measurable impact on the RT activity, regardless of the associated 3'→5' exonuclease activity (Table 2), suggesting the improvement of RT-PCR function was dependent on biochemical attributes other than nucleolytic activity, presumably modification of the binding affinity provided by the domain. In addition, the presence or absence of a 5'→3' nuclease activity did not substantially affect fidelity.

Example 15: Focused Mutagenesis of M160-Nuc for Increased Inhibitor Resistance

The sensitivity and specificity of nucleic acid amplification-based detection methods are often hindered by the presence of biological, chemical, and environmental inhibitors in target samples. These inhibitors include blood components, blood preservation chemicals, fabrics, plant and soil components, excess salts, detergents, and nucleic acid extraction chemicals. Methods that tolerate nucleic acid amplification inhibitors are therefore highly desirable and there remains a need for polymerases and polymerase formulations that increase resistance to inhibitors.

Heparin, a branched polymer of variable molecular weight and variably sulfated repeating disaccharide units, is commonly used as an anticoagulant and can copurify with nucleic acid samples derived from blood. With its high negative charge density, heparin can bind to DNA-interacting proteins such as reverse transcriptases and DNA polymerases, competing with nucleic acid template binding and interfering with activity. To engineer mutants of M160-nuc with increased heparin resistance, mutagenesis efforts targeted regions of the molecule predicted to associate with template nucleic acid. Mutations in the molecule that increase specificity of binding to nucleic acid template by increasing primed-template binding affinity or by decreasing heparin affinity should confer increased heparin resistance in RT-qPCR. Mutagenesis of M160-nuc focused on three regions of the polymerase, chosen based on sequence alignment with better characterized family A polymerases. The first region mutated was M160-nuc amino acid residues 750-753, predicted to correspond to a region of helix P, an exterior alpha helix in the fingers domain adjacent to template. The next round of mutagenesis targeted amino acids 776-783, predicted to correspond to helix Q, a region running parallel to the DNA template strand in the palm at the base of the fingers domain that faces DNA template and participates in binding to the minor groove. The final round targeted amino acids 622-627, predicted to correspond to motif 2, a region at the base of the fingers and thumb domain involved in binding primer-template duplex through minor groove and sugar phosphate interactions (Loh and Loeb, 2005).

Random and semi-random mutant libraries of M160-nuc sequences were prepared by assembling a partially degenerate oligonucleotide containing 25 nucleotide terminal overlaps with an inverse PCR-generated expression plasmid lacking the region to be mutagenized. Assembly was done using the RepliQa Assembly Mix™ (Quantabio) according to the manufacturer's recommendation. Approximately 128 clones from each mutagenized segment were expressed in *E. coli* and screened for performance in RT-PCR by measuring the ability of crude heat-treated lysate to amplify the 243 bp segment of phage MS2 RNA in the presence of heparin. In the helix P library, four distinct mutants (Helix P-62, 63, 69, and 88) were identified that showed enhanced performance in the presence of 10 ng/µl heparin compared with M160-nuc as evidenced by lower Cq values (Table 3). In the helix Q library, four distinct heparin-resistant mutants were also identified (Helix Q-9, 69, 87, 88). Of these, Helix Q-69 showed the most heparin resistance, resulting in a Cq of 9.1 in the presence of 10 ng/µl heparin, which is comparable to that of the parent M160-nuc in the absence of heparin (Cq=8.1). To identify mutants with even further increased heparin resistance, the next round of mutagenesis targeted Helix Q-69 at motif 2 and used a screen based on RT-PCR activity in the presence of 40 ng/µl heparin. Six distinct mutants (Motif 2-11, 25, 41, 108, 120, and 121) showed Cq values lower than the Helix Q-69 mutant. Of these, the Motif 2-108 mutant showed the highest heparin resistance and was able to amplify MS2 RNA in the presence of 40 ng/µl heparin with equal efficiency (Cq=7.9) as the parent M160-nuc in the absence of heparin (Cq=8.1).

TABLE 3

Primary screen of M160-nuc heparin resistant mutants

| Mutant | Amino acid changes | Heparin quantity (ng/µl) | Cycle threshold for detection of MS2 by RT-qPCR |
|---|---|---|---|
| Unmodified M160-nuc | None | 0 | 8.1 |
| Unmodified M160-nuc | None | 10 | 22.8-28.3 |
| Helix P-62 | Q750W, H751Q, Q752K, L753K | 10 | 21.0 |
| Helix P-63 | H751Q, Q752K, L753K | 10 | 14.9 |
| Helix P-65 | H751L, Q752K | 10 | 19.5 |
| Helix P-89 | Q750W, Q752K, L753Q | 10 | 18.1 |
| Helix Q-9 | W777G, D781H | 10 | 9.6 |
| Helix Q-69 | W777C, D781A | 10 | 9.1 |
| Helix Q-87 | W777Y, D781A | 10 | 12.3 |
| Helix Q-88 | W777Y, D781R | 10 | 21.5 |
| Unmodified M160-nuc | None | 40 | No amplification |
| Helix Q-69 | W777C, D781A | 40 | 18.7-19.3 |
| Motif2-11 | W777C, D781A, D622N, I623L, Q627N | 40 | 12.5 |
| Motif2-25 | W777C, D781A, D622S, Q627N | 40 | 11.5 |
| Motif2-41 | W777C, D781A, D622G, Q627S | 40 | 14.1 |
| Motif2-108 | W777C, D781A, D622N, Q627N | 40 | 7.9 |
| Motif2-120 | W777C, D781A, D622N, I623L, Q627S | 40 | 9.9 |
| Motif2-121 | W777C, D781A, Q627N | 40 | 13.5 |

Example 16: Secondary Screening of Heparin Resistant Mutants

To downselect from the group of identified heparin-resistant mutants, a secondary screen assessed performance in RT-qPCR by measuring heparin resistance and MS2 RNA detection sensitivity (Table 4). Two heparin-resistant mutants from each structural domain library were expressed in *E. coli* and purified by strong cation exchange and heparin spin-column chromatography as is known in the art. In addition, we constructed and purified three hybrid mutants (Hyb-1, Hyb-2, and Hyb-3) that contained mutations combined from different structural domains or subsets of the previously identified mutations. The quantity of enzyme to be used per RT-qPCR reaction was determined as the smallest quantity that showed no increase in the Cq value and the heparin resistance was defined as the highest quantity that increased the Cq value by <3 compared with reactions without heparin. The results of the hybrid mutant analysis of Hyb-2 and Hyb-3 showed that whereas the D622N and Q627N mutations enhanced the heparin resistance of the Q-69 mutant, the mutations on their own conferred no heparin resistance and so were excluded from further analysis. In addition, some mutants such as Q-69 appeared to show compromised detection sensitivity and therefore were also excluded. However, based on the results of the RT-qPCR analyses, three mutants showed both significant heparin resistance and high MS2 detection sensitivity and were chosen for further analysis (Table 5).

at 55° C. For both assays, fluorescence was measured at 15 second intervals and the initial slopes of fluorescence curves were calculated and compared for each polymerase. Despite the increased heparin resistance of the M501, M502, and M503 mutants and the high activity in RT-qPCR as shown in Table 4, neither the polymerase specific activity (FIG. 11, Panel A) nor the reverse transcriptase activity (FIG. 11, Panel B) of the mutants were significantly altered compared with the parental M160-nuc polymerase. In contrast, the increased binding affinity to primed-template DNA (FIG. 10,

TABLE 4

Secondary screen of M160-nuc heparin resistant mutants for RNA detection sensitivity in addition to heparin resistance.

| Mutant | Amino acid changes | Quantity enzyme tested in RT-qPCR | Heparin resistance | MS2 RNA detection sensitivity |
|---|---|---|---|---|
| Unmodified M160-nuc | None | 50 ng | <2.5 ng/μl | 20 copies |
| Helix P-62 | Q750W, H751Q, Q752K, L753K | 12.5 ng | <2.5 ng/μl | Not tested |
| Helix P-63 | H751Q, Q752K, L753K | 12.5 ng | 10 ng/μl | 20 copies |
| Helix Q-69 | W777C, D781A | 18 ng | 40 ng/μl | 2000 copies |
| Helix Q-88 | W777Y, D781R | 12.5 ng | 10 ng/μl | 200 copies |
| Motif2-108 | W777C, D781A, D622N, Q627N | 5 ng | >80 ng/μl | 200 copies |
| Motif2-121 | W777C, D781A, Q627N | 12.5 ng | >80 ng/μl | 200 copies |
| Hyb-1 | Q627N, H751Q, Q752K, L753K | 12.5 ng | 10 ng/μl | 20 copies |
| Hyb-2 | D622N, Q627N | 25 ng | <2.5 ng/μl | Not tested |
| Hyb-3 | Q627N | 25 ng | <2.5 ng/μl | Not tested |

TABLE 5

Inhibitor resistant mutant sequences

| Enzyme | Mutations | Nucleic acid sequence | Amino acid sequence |
|---|---|---|---|
| M501 | H751Q, Q752K, L753K | SEQ ID NO: 50 | SEQ ID NO: 51 |
| M502 | W777C, D781A, D622N, Q627N | SEQ ID NO: 52 | SEQ ID NO: 53 |
| M503 | Q627N, H751Q, Q752K, L753K | SEQ ID NO: 54 | SEQ ID NO: 55 |

Example 17: Polymerase and Reverse Transcriptase Activity of Heparin Resistant Mutants For further characterization of the biochemical properties of the M501, M502, and M503 mutants, the genes were overexpressed in E. coli and the polymerases were purified by iterative rounds of affinity and ion exchange column chromatography. To measure DNA polymerase activity, the relative rates of nucleotide incorporation were determined using a primed M13 template. Reactions (20 μl) containing 20 mM Tris, pH 8.8, 10 mM $(NH_4)_2SO_4$, 10 mM KCl, 2 mM $MgSO_4$, 0.1% Triton X-100, 200 uM dNTPs, 1×SYBR Green I (Thermo Fisher), 7.5 μg/ml M13mp18 DNA, 0.25 mM each of a mixture of three primers 24-33 nt in size, and 0-10 ng of enzyme were incubated at 72° C. To measure reverse transcriptase activity, reactions (20 μl) containing 50 mM Tris, pH 8.3, 75 mM NaCl, 5 mM $MgCl_2$, 1 mM DTT, 0.01% Tween-20, 2% trehalose, 0.4× EvaGreen dye (Biotium), 0.8 mM dTTP, 0.01 ug/μl Poly(A), 0.1 μM olgo(dT)$_{20}$ primer, and 0-20 ng polymerase were incubated Panel B and Panel C), suggests improved discrimination between template and heparin binding. For the M502 mutant, the measured affinity to primed template was at the sensitivity limit of the binding assay (Kd<6.1 nM), at least a 12-fold improvement compared with the parental M160-nuc polymerase (Kd=78.9).

Increased ionic strength due to the presence of elevated salt in nucleic acid samples has the potential to affect the binding between polymerase and DNA template. Elevated salt tolerance is correlated in DNA polymerases with processivity, which affects performance in PCR. To test whether the altered template binding effects produced by the mutations in the M501, M502, and M503 mutants also had the effect of improving salt tolerance, DNA polymerase activity assays were performed in the presence of between 2.5 and 100 mM KCl and reverse transcriptase activity assays were performed in the presence of between 10 and 200 mM NaCl (FIG. 12). Activity was measured by calculating the initial slopes of the fluorescent curves and the salt tolerance was determined as the quantity that reduced the maximum activity to 50% activity. For both DNA polymerase and reverse transcriptase activities, all three mutants additionally showed improved salt tolerance compared with the parental M160-nuc polymerase.

Example 18: Resistance to Additional PCR Inhibitors

Although the M501, M502, and M503 mutants were isolated from a biochemical screen designed to improve heparin resistance, they were further tested to determine possible resistance to additional PCR inhibitors (FIGS. 13-17). RT-qPCR reactions were performed using viral MS2

RNA as template and a dual-quenched FAM-labeled hydrolysis probe for amplification detection. Reactions (20 µl) contained 50 mM Tris, pH 8.75, 75 mM KCl, 3 mM MgCl$_2$, 0.3 mM dNTPs, 0.2 M trehalose, 0.025% Tween-20, 0.75 M betaine, $10^6$ copies of MS2 phage RNA, 0.3 µM forward and reverse primer (25 nucleotides each in size), 0.2 µM probe, and polymerase (100 ng of M160-nuc polymerase, 50 ng of M501, 25 ng of M502, or 50 ng of M503). The amplicon was 243 bp in size and corresponded to position 472 to 714 of the MS2 genome (GenBank Acc. No. V00642.1; SEQ ID NO:23). The probe was 22 nt in size, corresponded to position 650-671 and contained 5'-FAM/internal ZEN/3'-Iowa Black modifications. Each polymerase was tested with the following inhibitor concentrations: 0 to 50 ng/µl heparin, 0 to 4 µM hematin, 0 to 8 ng/µl humic acid, 0 to 800 ng/µl hemoglobin, or 0 to 80 ng/µl xylan. Reactions were thermal cycled in a QuantStudio system (Thermo Fisher) as follows: 94° C. 30 sec (1 cycle), 94° C. 5 sec, 72° C. 30 sec (40 cycles). Whereas all three mutants displayed improved resistance to heparin as expected (FIG. 13, Panel A), M503 also displayed slightly improved hematin resistance (FIG. 14, Panel A), hemoglobin resistance (FIG. 16, Panel A), and xylan resistance (FIG. 17, Panel A).

It has been previously shown that addition of serum albumin protein to PCR reactions improves tolerance to several inhibitors including FeCl$_3$, hemin, fulvic acids, humic acids, tannic acids, and fecal extracts (Kreader, 1996). However, the addition of 1 mg/ml human serum albumin to RT-qPCR reactions catalyzed by M160-nuc polymerase resulted in amplification inhibition, even in the absence of inhibitors (not shown). In contrast, the addition of 1 mg/ml human serum albumin to RT-qPCR reactions catalyzed by M501 and M503 provided additional tolerance to hematin (FIG. 14, Panel B), humic acid (FIG. 15, Panel B), hemoglobin (FIG. 16, Panel B), and xylan (FIG. 17, Panel B).

Example 19: RNA Detection Sensitivity in One-Step RT-qPCR Reactions

To test sensitivity of M501, M502 and M503 in detection of viral MS2 RNA, RT-qPCR reactions were performed using either a dual-quenched FAM-labeled hydrolysis probe for amplification detection (FIG. 18, Panel A) or using EvaGreen-based detection chemistry (FIG. 18, Panel B). Reactions (20 µl) contained 50 mM Tris, pH 8.75, 75 mM KCl, 3 mM MgCl$_2$, 0.3 mM dNTPs, 0.2 M trehalose, 0.025% tween 20, 0.75M betaine, the indicated number of copies of MS2 phage RNA, 0.3 µM forward and reverse primer (25 nucleotides each in size), and polymerase (100 ng of M160-nuc, 25 ng of M501, 12.5 ng of M502, or 25 ng of M503). The amplicon was 243 bp in size and corresponded to position 472 to 714 of the MS2 genome (GenBank Acc. No. V00642.1; SEQ ID NO:23).

Dye-based reactions contained 0.225× Eva Green (Biotium) and probe-based reactions contained 0.2 µM of a 5'-FAM/internal ZEN/3'-Iowa Black quenched 22 nt oligonucleotide (MS2 position 650-671). Reactions were thermal cycled in a QuantStudio system (Thermo Fisher) as follows: 94° C. 30 s (1 cycle), 94° C. 5 sec, 72° C. 30 sec (40 cycles). In both cases, the resulting Cq values were assessed. The results indicate compatibility of the M501, M502 and M503 mutants with both probe- and dye-based detection chemistries and that the presence of the mutations did not reduce detection sensitivity. The slightly lower Cq values for M501, M502 and M503 compared to M160-nuc indicate improved reverse transcription under these reaction conditions.

The M501, M502 and M503 mutants were tested for detection of mRNA transcripts in reactions designed to amplify a 145 bp region of the LDHA mRNA from total human RNA using a FAM probe-based RT-qPCR assay (FIG. 18, Panel C). Reactions (20 µl) contained 50 mM Tris, pH 8.75, 75 mM KCl, 3 mM MgCl$_2$, 0.3 mM dNTPs, 0.2 M trehalose, 0.025% Tween-20, 0.75 M betaine, total human RNA (Agilent), 0.3 µM forward and reverse primer (40 nt and 26 nt, respectively), 0.2 uM probe, and polymerase (100 ng of M160-nuc, 25 ng of M501, 12.5 ng of M502, or 25 ng of M503). The amplicon corresponded to position 1428 to 1572 of the LDHA transcript (GenBank Acc. No. NM_005566.3; SEQ ID NO:24). The probe was 34 nt in size, corresponded to position 1509-1542 and contained 5'-FAM/internal ZEN/3'-Iowa Black modifications.

Reactions were thermal cycled in a QuantStudio system (Thermo Fisher) as follows: 94° C. 30 sec (1 cycle), 94° C. 5 sec, 72° C. 30 sec (45 cycles). The LDHA copy number was determined in the total human RNA by digital PCR quantification. We found that in reactions catalyzed by the M502 mutant, only as few as 10,000 copies of the LDHA mRNA were detected, compared with as few as 10 copies for M160-nuc. This indicates a negative effect of the M502 mutations in amplification reactions using this complex template, likely associated with reduced template specificity. However, in reactions catalyzed by the M501 and M503 mutants, as few as 10 copies were detected, indicating a high degree of sensitivity and specificity in the presence of a complex mixture of target and non-target background RNA.

Example 20: Improved Hydrolysis Probe-Based Fluorescent Signal Generation Using Polymerase Mixtures Containing Taq DNA Polymerase Although the hybrid and mutant polymerases described in this invention comprising fusions with the 5'→3' nuclease domain of Taq polymerase are able to efficiently utilize hydrolysis probe-based detection chemistry in qPCR reactions, it is possible that the nuclease and polymerase domains are not in an optimal configuration for maximum fluorescent signal generation for all probe sequences and templates. Taq polymerase and its derivatives are commonly used in qPCR mixtures for probe-based detection, so its inclusion in the enzyme mixture may be advantageous for signal generation. To test whether fluorescent probe-based signal could be improved in one-step RT-qPCR detection of LDHA, mRNA from total human RNA, 20 µl amplification reactions were compared to M503 polymerase alone with mixtures of M503 and Taq polymerase (FIG. 19). The addition of either 2 U or 4 U of Taq polymerase to the M503 mutant did increase the maximum normalized relative fluorescence units (RFU) for all quantities of template tested, up to a 2.8-fold increase in reactions with the fewest copies of template (FIG. 19, Panel A). In addition, the increase in fluorescent signal in reactions containing Taq polymerase in the enzyme mixture allowed for earlier detection and lower Cq values (FIG. 19, Panel B).

Example 21: Inhibitor Resistance and Amplification Speed Using Enzyme Mixtures Containing Taq DNA Polymerase To test the upper limits of inhibitor resistance of the M503 mutant in amplification reactions containing both HSA and Taq polymerase, the following concentration ranges of inhibitory components were tested: 0 to 50 ng/µl heparin, 0 to 100 µM hematin, 0 to 80 ng/µl humic acid, 0 to 5 µg/µl hemoglobin, and 0 to 1 μg/μl xylan. Reactions (20 μl) contained 50 mM Tris, pH 8.75, 75 mM KCl, 3 mM MgCl$_2$, 0.3 mM dNTPs, 0.2 M trehalose, 0.025% Tween-20, 0.75 M betaine, $10^6$ copies of MS2 phage RNA, 0.3 μM forward and reverse primer (25 nucleotides each in size), 0.2 μM probe, and polymerase (100 ng of M160-nuc polymerase or a mixture of 50 ng M503 and 2 U Taq polymerase). Reactions containing M503 also contained 1 mg/ml HSA. The amplicon was 243 bp in size and corresponded to position 472 to 714 of the MS2 genome (GenBank Acc. No. V00642.1; SEQ ID NO:23). The probe was 22 nt in size, corresponding to position 650-671, and contained 5'-FAM/internal ZEN/3'-Iowa Black modifications. Reactions were thermal cycled in a QuantStudio system (Thermo Fisher) as follows: 94° C. 30 sec (1 cycle), 94° C. 5 sec, 72° C. 30 sec (40 cycles). For these reactions, the resistance was defined as the highest inhibitor quantity that increased the Cq value by <3 compared with reactions without inhibitor. The formulation containing HSA and the mixture of M503 and Taq polymerase showed resistance to high levels of all inhibitors tested, especially compared with the unmodified M160-nuc polymerase alone in a formulation lacking HSA (Table 6).

a different fluorophore (FIG. 21). The template pool consisted of a mixture of DNA plasmids containing either ACTB (SEQ ID NO:56), GAPDH (SEQ ID NO:57), IL1 B (SEQ ID NO:58), or TUBA (SEQ ID NO:59) gene sequences and were present in reactions at a quantity of $10^8$ to $10^1$ copies as indicated. Reactions (20 μl) containing 50 mM Tris, pH 8.75, 75 mM KCl, 3 mM MgCl$_2$, 0.3 mM dNTPs, 0.2 M trehalose, 0.025% Tween-20, 0.75 M betaine, 1 mg/ml HSA, 50 ng M503, 2 U Taq polymerase, 0.2 μM forward and reverse primer and 0.3 uM probe (Table 7) were thermal cycled as follows: 94° C. 3 minutes (1 cycle), 94° C. 10 sec, 58° C. 1.5 minutes (45 cycles). In reactions containing equal quantities of each of the four target DNA sequences (FIG. 21, Panel A), each amplicon was detected successfully using different spectral emission filters from a starting template quantity as low as 10 copies. In addition, the GAPDH gene sequence was detected successfully from starting quantity as few as 10 copies, even in the presence of $10^8$ copies of the other three target sequences (FIG. 21, Panel B). Together, these indicate high detection sensitivity and dynamic range, and compatibility with multiple fluorophores in probe-based detection chemistry using this formulation.

TABLE 6

Inhibitor resistance of an M503 and Taq polymerase mixture in the presence of human serum albumin compared with the M160-nuc polymerase without human serum albumin in one-step RT-qPCR reactions.

| Polymerase | Heparin resistance | Hematin resistance | Humic acid resistance | Hemogloban resistance | Xylan resistance |
| --- | --- | --- | --- | --- | --- |
| M160-nuc no HSA | <0.78 ng/μl | <1.6 μM | <1.25 ng/μl | 0.1 μg/μl | <0.016 μg/ul |
| M503 + Taq with 1 mg/ml HSA | 12.5 ng/μl | >100 μM | 20 ng/μl | 2.5 μg/μl | >1 μg/ul |

High polymerase extension speed is desirable in PCR-based nucleic acid detection reactions because it allows for reduced cycle times, thereby reducing the overall time-to-result. PCR extension speed was measured in end-point reactions in which the combined anneal and extension time was varied to determine the minimum time required to efficiently amplify a 243-nucleotide region of the MS2 viral genome (FIG. 20). Reactions (20 μl), contained 50 mM Tris, pH 8.75, 75 mM KCl, 3 mM MgCl$_2$, 0.3 mM dNTPs, 0.2 M trehalose, 0.025% Tween-20, 0.75 M betaine, $10^7$ copies of MS2 phage RNA, 0.3 μM forward and reverse primer, 1 mg/ml HSA (except for reactions using M160-nuc), and polymerase (100 ng of M160-nuc polymerase, 50 ng M503, or a mixture of 50 ng M503 and 2 U Taq polymerase). After preparing each composition, reactions were thermal cycled as follows: 94° C. 30 sec (1 cycle), 94° C. 5 sec, 72° C. for the indicated time (30 cycles), then products were analyzed by 1% agarose gel electrophoresis, stained with ethidium bromide, and visualized using ultraviolet light (FIG. 20). For each of the three polymerase compositions tested (M160-nuc, M503 and M503/Taq), efficient amplification of the 243 bp product was seen with an extension time as short as 5 seconds.

Example 22: Amplification of Four DNA Sequences with M503 in Multiplex qPCR Reactions The capacity of the mixture of M503 and Taq polymerase to catalyze the simultaneous detection of four target genes was tested in multiplex qPCR reactions using probe-based chemistry in which each of the four probes is labeled with

TABLE 7

Oligonucleotide sequences used in multiplex qPCR assays.

| Oligo name | Nucleic acid sequence | 5'-Label | 3'-Quencher |
| --- | --- | --- | --- |
| GAPDH Fwd | SEQ ID NO: 60 | | |
| GAPDH Rev | SEQ ID NO: 61 | | |
| GAPDH Probe | SEQ ID NO: 62 | 6-FAM | BHQ1 |
| ACTB Fwd | SEQ ID NO: 63 | | |
| ACTB Rev | SEQ ID NO: 64 | | |
| ACTB Probe | SEQ ID NO: 65 | CAL Orange 560 | BHQ1 |
| IL1-B Fwd | SEQ ID NO: 66 | | |
| IL1-B Rev | SEQ ID NO: 67 | | |
| IL1-B Probe | SEQ ID NO: 68 | CAL Red 610 | BHQ2 |
| TUBA Fwd | SEQ ID NO: 69 | | |
| TUBA Rev | SEQ ID NO: 70 | | |
| TUBA Probe | SEQ ID NO: 71 | Quasar 670 | BHQ2 |

Example 23: Activating 3'→5' Nuclease Activity Enables Reverse Transcription Proofreading on an RNA Template Enzyme constructs that combine the inhibitor tolerant properties of the mutants M502 and M503 with the proofreading properties of the exonuclease derivative mutants (Table 2), i.e. mutants M601, M602, M603, and M604, were constructed by introducing the G46D and A339E mutations into the M502 and M503 parent sequences (Table 8), expressing the recombinant proteins in E. coli, and purifying the mutant polymerases.

TABLE 8

Inhibitor resistant and proofreading mutant sequences.

| Enzyme | Parent | Amino acid changes | Nucleic acid sequence | Amino acid sequence | 3'→5' nuclease | 5'→3' nuclease |
|---|---|---|---|---|---|---|
| M601 | M502 | A339E | SEQ ID NO: 73 | SEQ ID NO: 74 | + | + |
| M602 | M502 | G46D, A339E | SEQ ID NO: 75 | SEQ ID NO: 76 | + | − |
| M603 | M503 | A339E | SEQ ID NO: 77 | SEQ ID NO: 78 | + | + |
| M604 | M503 | G46D, A339E | SEQ ID NO: 79 | SEQ ID NO: 80 | + | − |

Proofreading reverse transcriptase activity was demonstrated using a modified version of the DPE-PCR assay (Zweitig et al., 2012). Substrates were constructed by annealing a template RNA strand (SEQ ID NO:81) to a DNA primer strand containing either a 3'-terminal nucleotide match (SEQ ID NO:82), a 3'-terminal dC mismatch (SEQ ID NO:83), a 3'-terminal dA mismatch (SEQ ID NO:84), or a 3'-terminal dT mismatch (SEQ ID NO:85) opposite the RNA cytosine base. Extension reactions (50 µl) containing 20 mM Tris, pH 8.8, 10 mM NaCl, 10 mM $(NH_4)_2SO_4$, 2 mM $MgSO_4$, 0.1% Triton X-100, 0.2 mM dNTPs, 0.001 µM annealed substrate, and a quantity of polymerase normalized for reverse transcriptase activity were incubated at 65° C. for 10 minutes and then the polymerases were heat inactivated by incubating at 95° C. for 3 minutes. The extent of reverse transcription extension was then measured in quantitative PCR reactions (20 µl) containing 1× Phoenix Hot Start buffer (QIAGEN), 0.2 mM dNTPs, 333 nM forward primer (SEQ ID NO:86), 333 nM reverse primer (SEQ ID NO:87), 166 nM probe (SEQ ID NO:88), 2 U RNase H (QIAGEN), 0.4 U Phoenix Hot Start Taq polymerase (QIAGEN), and 2 µl extension reaction product. Reactions were incubated at 37° C. for 10 minutes, 50° C. for 10 minutes, then 95° C. for 3 minutes; followed by 40 cycles of 95° C. for 5 s and 65° C. for 20 s with fluorescence data collection during the anneal/extension step. Compared with a fully matched primed RNA template, reactions with the 3'→5' exo-M502 and M503 polymerases displayed higher Cq values using the terminal mismatched templates (FIG. 22), indicating inefficient reverse transcription extension of primers terminating in mismatched bases. In contrast, the 3'→5' exo+M601, M603, and M604 polymerases showed equivalent reverse transcription extension efficiency from both the matched and all terminal mismatched templates, indicating an efficient ability to excise and correct the mismatched terminal base, i.e. proofread.

The invention claimed is:

1. A polypeptide comprising a first amino acid sequence and a second amino acid sequence,
   wherein the first amino acid sequence comprises an amino acid sequence of SEQ ID NO:16 or an amino acid sequence at least 90% identical to SEQ ID NO:16, and
   wherein the second amino acid sequence is selected from the group consisting of SEQ ID NO:17 and SEQ ID NO:72, or an amino acid sequence at least 90% identical to SEQ ID NO:17 or SEQ ID NO:72,
   wherein the polypeptide has polymerase activity.

2. The polypeptide according to claim 1, further comprising a third amino acid sequence that corresponds to the sequence of positions 12-22 of the sequence of SEQ ID NO:15, or a sequence at least 90%, identical thereto.

3. The polypeptide according to claim 2, wherein the N-terminus is an amino acid sequence of "MN($X_1$)PK-PILKPQ($X_2$)KALVEPVLC($X_3$)SI($X_4$)EIPA" (SEQ ID NO:21); or variants thereof, wherein $X_1$=A or T; $X_2$=P or S; $X_3$=N or D; and $X_4$=N or D.

4. The polypeptide according to claim 1, wherein the polypeptide comprises an amino acid sequence of SEQ ID NO:2, SEQ ID NO:4, SEQ ID NO:6, SEQ ID NO:8, SEQ ID NO:10, or SEQ ID NO:12, or an amino acid sequence at least 90% identical thereto.

5. The polypeptide according to claim 1, wherein the polypeptide comprises an amino acid sequence of SEQ ID NO:14, SEQ ID NO:45, SEQ ID NO:47, SEQ ID NO:49, SEQ ID NO:51, SEQ ID NO:53, SEQ ID NO:55, SEQ ID NO:74, SEQ ID NO:76, SEQ ID NO:78, SEQ ID NO:80 or an amino acid sequence at least 90% identical thereto.

6. The polypeptide of claim 4, wherein the polypeptide comprises the amino acid sequence of SEQ ID NO:4.

7. The polypeptide according to claim 6, wherein the polypeptide exhibits reverse transcriptase activity and/or 5'→3' exonuclease activity.

8. A composition comprising the polypeptide according to claim 1.

9. A vector encoding the polypeptide according to claim 1.

10. A transformed host cell comprising the vector according to claim 9.

11. A method for amplifying template nucleic acids comprising contacting the template nucleic acids with the polypeptide according to claim 6, preferably wherein the method is reverse transcription (RT) PCR.

12. The method according to claim 11, wherein the method comprises:
   a) generating cDNA using the polypeptide; and
   b) amplifying the generated cDNA using the polypeptide.

13. The method according to claim 12, wherein the same polypeptide is applied for steps a) and b).

14. The method according to claim 12, wherein reverse transcription of step a) and the amplification of step b) are performed at isothermal conditions.

15. A kit comprising
   the polypeptide of claim 1; and
   a buffer.

* * * * *